US006017719A

United States Patent [19]

Tseng-Law et al.

[11] Patent Number: 6,017,719

[45] Date of Patent: Jan. 25, 2000

[54] POSITIVE AND POSITIVE/NEGATIVE CELL SELECTION MEDIATED BY PEPTIDE RELEASE

[75] Inventors: Janet Tseng-Law, Whitter; Joan A. Kobori, Pasadena; Fahad A. Al-Abdaly, Torrance; Roy Guillermo, Carson; Sam L. Helgerson, Pasadena; Robert J. Deans, Claremont, all of Calif.

[73] Assignee: Nexell Therapeutics, Inc., Irvine, Calif.

[21] Appl. No.: 08/482,528

[22] Filed: Jun. 7, 1995

Related U.S. Application Data

[63] Continuation-in-part of application No. 08/259,427, Jun. 14, 1994, abandoned.

[51] Int. Cl.[7] .......................... G01N 33/53; G01N 33/553

[52] U.S. Cl. .......................... 435/7.21; 435/7.1; 435/7.2; 435/7.24; 435/7.25; 436/518; 436/526

[58] Field of Search .......................... 435/7.1, 7.2, 7.21, 435/7.24, 7.25; 436/518, 524, 526, 528, 531, 806

[56] References Cited

U.S. PATENT DOCUMENTS

| | | | |
|---|---|---|---|
| 4,709,037 | 11/1987 | Sigler | 546/271 |
| 4,798,795 | 1/1989 | Sigler | 435/177 |
| 4,965,204 | 10/1990 | Civin | 435/240 |
| 5,035,994 | 7/1991 | Civin | 435/2 |
| 5,081,030 | 1/1992 | Civin | 435/240 |
| 5,130,144 | 7/1992 | Civin | 424/577 |
| 5,215,927 | 6/1993 | Berenson et al. | 436/541 |
| 5,225,353 | 7/1993 | Berenson et al. | 436/541 |
| 5,316,943 | 5/1994 | Kidman et al. | 435/280 |
| 5,358,934 | 10/1994 | Borovsky et al. | 514/17 |
| 5,525,503 | 6/1996 | Rudd et al. | 435/240.2 |
| 5,536,475 | 7/1996 | Moubayed et al. | 422/101 |
| 5,610,031 | 3/1997 | Burgeson et al. | 435/69.1 |

FOREIGN PATENT DOCUMENTS

| | | |
|---|---|---|
| 0344006A2 | 5/1989 | European Pat. Off. . |
| 0395355A1 | 4/1990 | European Pat. Off. . |
| 503939 | 3/1992 | European Pat. Off. . |
| 3629194A1 | 3/1987 | Germany . |
| 91/01368 | 2/1991 | WIPO . |
| WO92/09628 | 6/1992 | WIPO . |
| WO92/15683 | 9/1992 | WIPO . |
| WO93/14781 | 8/1993 | WIPO . |
| WO93/16715 | 9/1993 | WIPO . |
| WO94/02016 | 2/1994 | WIPO . |
| WO94/03487 | 2/1994 | WIPO . |
| WO95/07466 | 3/1995 | WIPO . |
| WO95/09230 | 4/1995 | WIPO . |

OTHER PUBLICATIONS

MacVector™ User's Manual, International Biotechnologies, Inc., pp. B56–B69.

Zagury, JF, et al., *Proc. Natl. Acad. Sci. U.S.A.*, 90:7573–7577, 1993.

Pellequer, J.L., et al., Methods in Enzymology, 203:176–201, 1991.

Williams, W.V., et al., *Proc. Natl. Acad. Sci. U.S.A.*, 86:5537–5548, 1989.

Jameson, B.A., et al., *Comput. Applic. in the Biosciences*, 1988, 4:181–186.

Barbas et al., "High–affinity self–reactive human antibodies by design and selection: Targeting the integrin ligand binding site," *Proc. Natl. Acad. Sci. USA* 90:10003–10007 (1993).

Burgess et al., "Possible dissociation of the heparin–binding and mitogenic activities of heparin–binding (acidic fibroblast) growth factor–1 from its receptor–binding activities by site–directed mutagenesis of a single lysine residue," *J. Cell Biol.* 111:2129–2138 (1990).

Birnbaum and Mosbach, "Peptide screening," *Biotechnology* 3:49–54 (1992).

Lazar et al., "Transforming growth factor $\alpha$: mutation of aspartic acid 47 and leucine 48 results in different biological activities," *Mol. Cell. Biol.* 8:1247–1252 (1988).

Tao and Morrison, "Studies of aglycosylated chimeric mouse–human IgG: role of carbohydrate in the structure and effector functions mediated by the human IgG constant region," *J. Immunol.* 143:2595–2601 (1989).

Sivestri et al., Leukemia and Lymphoma, vol. 8, pp. 389–396 (1992) "Comparison of Two Methods for Concentrating CD34+ Cells from Patients with Acute, Non–Lymphocytic Leukemia".

Strauss et al., The American Journal of Pediatric Hematology/Oncology, vol. 13, No. 2, pp. 217–221, (1991) "Selection of Normal Human Hematopoietic Stem Cells for Bone Marrow Transplantation Using Immunomagnetic Microspeheres and CD34 Antibody".

Eds. Savage, MD, et al., "Biotinylation Reagents", *Avidin–Biotin Chemistry: A Handbook,* pp. 25–87.

Hardwick, A., et al., "Development of a Large–Scale Immunomagnetic . . . ", *Advances in Bone Marrow Purging and Processing,* vol. 377, Eds. Worthington–White, DA, et al., Wiley–Liss, Inc., New York, pp. 583–589.

Hardwick, A., et al., "Design of Large–Scale Separation Systems . . . ", *J. Hematotherapy* 1:379–386, 1992.

Berardi, A.C., et al., "Functional Isolation and Characterization . . . ", *Science* 267:104–108, 1995.

(List continued on next page.)

*Primary Examiner*—Lora M. Green
*Attorney, Agent, or Firm*—Campbell & Flores LLP

[57] ABSTRACT

The invention provides a nonenzymic method for the release of cells which have been selected from a heterogeneous cell suspension by antibody-mediated binding to beads or other solid support. The method entails forming within the cell suspension a complex comprising the solid support linked to a primary monoclonal antibody, which in turn is bound to a cell surface antigen on the target cells. The complex is separated from the cell suspension, and then contacted with a specific peptide which binds to the primary antibody, displacing the antibody from the cell surface antigen, thereby releasing the target cell from the complex. The invention also provides methods for positive/negative cell selection wherein target cells having a first antigen are selected from a heterogeneous cell suspension containing undesired cells having a second antigen.

16 Claims, 5 Drawing Sheets

OTHER PUBLICATIONS

Alberts, B., et al., Eds., "The Functional Properties of Antibodies", *Molecular Biology of the Cell,* Garland Publishing, New York and London, 1983, pp. 969–970.

Bowie, J.U., et al., "Deciphering the Message in Protein Sequences . . . ", *Science,* 247:1306–1310, 1990.

Nakanishi, H., et al., "Peptidomimetics of the immunoglobulin . . . ", *Gene,* 137:51–56.

Wells, J.A., et al., "Rapid evolution of peptide . . . ", *Current Opinion in Biotechnology,* 3:355–362.

Scott, J.A., "Discovering peptide ligands . . . ", *Trends in Biochemical Sciences,* 17:241–245.

Smith, G.P., "Filamentous Fusion Phase . . . ", *Science,* 228: 1315–1316, 1985.

Simmons, D.L., et al., "Molecular Cloning of a cDNA . . . ", *J. Immunol,* 148:267–271.

He, X–Y., et al., "Isolation and Molecular Characterization . . . ", *Blood,* 79:2296–2302.

Civin, CI, et al., "Positive Stem Cell Selection . . . ", Bone Marrow Purging and Processing, Eds. S. Gross, et al., Alan R. Liss, Inc., New York, 1990, pp. 387–402.

Pelton, J.T., et al., "Conformationally restricted analogs . . . ", *Proc. Natl. Acad. Sci. U.S.A.,* 82:236–239.

Dyson, H., et al., "The Physical Basis for Induction . . . ", 1988, *Annual Review of Biophysics & Biophysical Chemistry,* 17:305–324.

POSITIVE AND POSITIVE/NEGATIVE CELL SELECTION MEDIATED BY PEPTIDE RELEASE

This is a Continuation-in-part of application Ser. No. 08/259,427 filed Jun. 14, 1994, abandoned.

TECHNICAL FIELD

The invention relates to peptides used to mediate cell release from antibody binding, methods of isolating such peptides, and methods for the specific release of target cells captured by antibody selection from a heterogeneous cell suspension. The general field is also known as cell selection.

BACKGROUND

The selection of one or more specific cell phenotypes from a heterogeneous cell composition, e.g. blood or bone marrow, has particular utility for cellular and gene therapies. For example, it has been demonstrated that the selection of cells expressing the CD34 antigen has utility in several therapies, such as a part of an adjunctive treatment for cancer (Civin, U.S Pat. Nos.: 5,035,994; 4,965,204; 5,081,030; 5,130,144). The selection of specific target cells for genetic manipulation is also of particular interest.

There are numerous cell selection techniques. For example, quiescent CD34+ cells may be selected by treating a hematopoietic cell culture with a chemical such as 5-fluorouracil which selectively kills dividing cells (Berardi, A. C. et al., *Science* 267:104–108, 1995). One particularly useful approach utilizes the selective binding of antibodies. Antibodies naturally bind to a specific antigen expressed by only certain cells. By matching an antibody to a specific cellular antigen, such cells may be physically removed or identified in a heterogeneous cell population. For discussions of antibody selection see Areman, E. et al., Eds. *Bone Marrow and Stem Cell Processing*, F.A. Davis Company, Philadelphia, 1992, and Gee, A. P., et al, Eds. *Advances in Bone Marrow Purging and Processing*, Wiley-Liss, New York, 1993.

Cellular selection techniques generally fall with two broad categories, negative cell selection and positive cell selection. As the terms imply, negative selection involves the removal of selected cell phenotypes from a population, while positive selection involves the selection or isolation of a specific cell phenotype from a larger heterogeneous cell population.

Negative cell selection techniques have found use in the removal of potentially harmful cells from a patient's or a donor's blood or bone marrow. For instance, a treatment for metastatic cancer may involve removal of a sample of the patient's bone marrow prior to ablative chemotherapy or radiation, with the intent to replace the patient's bone marrow cells after the ablative therapy in order to replenish hematopoietic cells. To minimize the risk of returning metastatic tumor cells to the patient, negative cell selection or purging is applied to the patient's bone marrow sample prior to reinfusion. One method of performing this negative cell selection involves the use of anti-tumor antibodies linked to a solid phase, such as magnetic beads, for binding the tumor cells and removing from blood, see (Hardwick, A., et al., *J Hematotherapy* 1:379–386, 1992). Negative selection of cells using lysis or enzymatic elimination of certain cells has also been employed (Areman, et al., supra).

As stated, positive selection involves targeting and separating a specific cell phenotype from a heterogeneous cell population. For example, cells expressing the CD34 antigen have been selected for use in bone marrow transplantation (Gee, et al., supra). While selection techniques employing toxic agents, e.g., (lytic agents), have been employed to eliminate certain cell types, the selectivity of such approaches are limited to removal or elimination of certain cells, not the affirmative selection of a specific cell type.

The use of antibodies for binding to specific cells has found widespread utility in positive selection techniques (Gee, et al., supra). One approach involves tagging or binding to the antibody a fluorescent dye and passing the antibody bound to the cell through a sorter. The cells to which the antibodies bind are identified and segregated by fluorescence-activated cell sorting (FACS). Another technique involves the binding of the antibody to a solid phase support or particle. Passing a cell composition past the antibody bearing support allows the antibodies to bind and hold the desired cells, thus removing the desired cells from the composition. Incubating a cell composition with antibody bearing particle, i.e., paramagnetic particles, allows for the separation of the particle bound cells from the remainder of the population, i.e., through magnetic separation (Gee et al., supra, pp.293–302).

The captured cells must be released from any solid support after the selection process, but in such a manner so as to maintain viability of the captured cells. Further, some researchers maintain that continued binding of an antibody or antibody fragment to the cell effects the usefulness of the cell (Berardi, et al. supra).

A particular concern with any positive cell selection technique employing an antibody based mechanism, is the retention of viability of the desired cells while effecting their release from the antibody and solid phase separation material. Release of the cells through variation of the surrounding pH and temperature is difficult since the pH must be maintained at around 7.0–7.4, and the temperature cannot be raised much higher than 37° C.

Certain cell types may tolerate low levels of reducing agents such as dithiothreitol and/or chelating agents such as EDTA, while other target cells may not remain viable even under very mild reducing or chelating conditions.

The strong affinity of avidin for biotin has been employed to effect the binding of cells to antibody bearing solid supports.

In avidin/biotin based techniques, typically an antibody which is specific for the target cell is biotinylated according to one of several standard methods (*Avidin-Biotin Chemistry: A Handbook*, Eds. Savage, MD, et al., fierce Chemical Co, 1992). For negative selection, the target cell is bound by the biotinylated antibody, which in turn is bound to an avidin-coated solid phase, usually in column form. The non-bound cells are then recovered, and the negatively selected cells bound to avidin are discarded.

For positive cell selection, however, the very strong affinity of avidin for biotin is disadvantageous since the target cells are firmly held within the cell/antibody-biotin/avidin complex. Since the avidin/biotin interaction is so strong, the disruption of other bonds was proposed for the release of desired target antigens. Certain biotinylating agents have chemically cleavable covalent bonds within their spacer arms or form cleavable covalent bonds with target proteins (Sigler, G. F. U.S. Pat. Nos.: 4,798,795 and 4,709,037; Wilchek, M., et al, German Pat. App. DE 3629194 A; *Avidin-Biotin Chemistry: A Handbook*, supra, p.41). The bonds are cleaved under reducing conditions employing dithiothreitol, mercaptoethanol, or sodium borohydride, but these conditions are generally too damaging to cells to be considered for selection of cells which must remain functional.

Other techniques involve the competitive displacement of biotin from the avidin support, leaving the biotinylated antibody bound to the cell. Alternatively, a biotin-analog is covalently bound to a primary antibody which binds to the cell of interest. The cell/antibody/biotin-analog complex is bound by a secondary anti-biotin antibody, bound to a solid support, for separation from the heterogeneous cell mixture. Then the cell/antibody/biotin-analog complex is released from the secondary antibody by competition with biotin. This method necessarily leaves the antibody bound to the cell (Al-Abdaly, F. et al., PCT/US95/03711).

Several techniques for positive cell selection rely on mechanical means for disruption of antibody/epitope interactions for release of selected cells. Tissue culture flasks may be coated with a primary antibody which binds the target cells; after the unbound cells are washed away, the target cells are released by striking the sides of the flask (Lebkowski, JS, et al., *Transplantation* 53:1101–1019, 1992). Another method for positive cell selection employs a "sandwich" technique which involves avidin bound to a biotinylated secondary antibody which binds a primary antibody, which in turn binds the target cell to form a complex. After separation of the complex from the heterogeneous cell suspension, the target cell is removed from the avidin by agitation to disrupt the interaction between the secondary and primary antibodies (Berenson, R. J., et al., U.S. Pat. Nos.: 5,215,927 and 5,225,353). Mechanical release is disadvantageous for the obvious reason that cells may sustain damage during the release process, and it has been reported that low numbers of viable cells are recovered after mechanical release (Egeland, T., et al., *Scand J Immunol* 27: 439–444, 1988). There is also the possibility that antibody fragments might adhere to the cells.

Another method for cell release involves proteolysis by enzymes such as papain and chymopapain. The target cells may be bound to magnetic beads via a primary antibody which is in turn bound to magnetic beads. After the cell/antibody/bead complex is removed from the heterogeneous cell suspension, the cells are released from the beads by proteolysis of the cell surface antigen or the antibody, or both (Hardwick, A., et al., *J Hematotherapy* 1:379–386, 1992; Civin, CE, et al., In *Bone Marrow purging and Processing Progress in Clinical And Biological Research*, Vol. 333, Eds. S. Gross, et al., Alan R. Liss, Inc, New York, pp 387–402; Civin, CI, EP 0 395 355 Al; Hardwick, A., et al., In *Advances in Bone Marrow Purging and Processing—Progress in Clinical and Biological Research*, Vol. 377, Eds. Worthington-White, DA, et al., Wiley-Liss, Inc., New York, pp 583–589). Proteolysis by papain or chymopapain is advantageous over mechanical disruption because these enzymes are not generally harmful to cells. However, enzymes digest cell surface proteins which could be important for the proliferation, differentiation, and homing of hematopoietic stem cells, for instance. Moreover, the digestion of cell surface proteins makes subsequent negative selection difficult or impossible.

Another technique involves the competitive displacement of the antibody from the cell antigen using additional antibody or antibody fragments. However, while this approach effects the release of a cell from a solid support, at least a portion of an antibody remains bound to the resulting cell, which may be detrimental (Berardi, et al., supra).

There remains a need for a positive cell selection method which produces a high yield of functional target cells, and which relies on relatively inexpensive, benign reagents in a physiologically compatible solution. Moreover, there remains a need for a positive cell selection method which leaves cell surface proteins intact. It would also be advantageous to have a method which leaves the positively selected cells free from antibodies or other ligands bound to the cell surface.

SUMMARY OF THE INVENTION

The invention provides a non-enzymatic method for the positive selection of target cells from a heterogeneous cell suspension. The method entails forming within the cell suspension a complex comprising a cell separation means such as a paramagnetic bead linked to a primary antibody, which in turn is bound to a cell surface antigen on the target cells (see FIG. 1). The complex is separated from the cell suspension, and then contacted with a specific peptide which binds to the primary antibody and thereby releases the target cell from the complex.

In one preferred method of the invention, a paramagnetic bead is linked to the primary antibody by a protein means such as a secondary antibody. This embodiment of the invention entails forming within the heterogeneous cell suspension a complex comprising the target cell bound to a primary antibody, which in turn is bound by a secondary antibody linked to the paramagnetic bead (see FIG. 2). The complex is separated from the cell suspension, and then contacted with a specific peptide which binds to the primary antibody and thereby releases the target cell from the complex. The paramagnetic bead, linked to secondary and primary antibodies, is then separated from the target cell by conventional magnetic means.

The invention also provides methods for double positive cell selection, wherein a target cell bearing two desired antigens is selected from a heterogeneous cell suspension (see FIGS. 3A and 3B).

The invention also provides methods for positive/positive cell selection wherein two different target cells, each bearing a different desired antigen, are selected from a heterogeneous cell suspension.

The invention also provides methods for positive/negative cell selection wherein a target cell having a first antigen is selected from a heterogeneous cell suspension containing also undesired cells having the first antigen as well as a second antigen (see FIG. 4). Positive/negative selection methods may also be applied to a cell suspension in which undesired cells are inadvertently trapped in the cell suspension containing the desired cells (FIG. 4). An exemplary method for positive/negative cell selection entails forming within the heterogeneous cell suspension a complex comprising a target cell having a first antigen bound to a first primary antibody, which in turn is bound by a secondary antibody coupled to a paramagnetic bead; the paramagnetic bead of the complex is also linked to a second primary antibody which is bound to a second antigen on an undesired cell. The complex is separated from the cell suspension, and then contacted with a specific peptide which binds to the first primary antibody, thereby displacing the primary antibody from the first antigen and releasing the target cell. The complexes of the paramagnetic beads attached to the primary and secondary antibodies and to the undesired cells are then separated by conventional magnetic means from the released target cell.

The method provides a peptide which binds to a monoclonal antibody bound to a cell surface antigen on a target cell, displaces the antibody from the cell surface antigen, and thereby releases the target cell from the antibody.

The invention also provides methods and specific peptide compositions for positive selection and specific release of target human hematopoietic stem/progenitor cells bound by the monoclonal anti-CD34 antibodies produced by the hybridomas designated ATCC HB 11646 and ATCC HB 11885, as well as the commercially available antibody 561 (Dynal, Oslo, Norway).

The invention also provides methods and specific peptide compositions for positive selection and specific release of target human breast cancer cells bound by the monoclonal anti-breast cancer antibody 9187 produced by the hybridoma designated ATCC HB 11884.

The invention also provides a method for identifying a specific peptide useful for the release of a target cell from the binding of a specific monoclonal antibody. The method comprises first selecting a candidate releasing peptide by at least one of the following means:

a) peptide library phage display followed by biopanning with the antibody of interest;

b) determination of potential antigenic peaks of the antigen;

c) complementarity-determining-region (CDR) peptide analysis of the antibody of interest;

d) random peptide library display on pins and binding with the antibody of interest;

e) theoretical molecular modeling of the three dimensional structure of said monoclonal antibody.

The candidate peptide is then tested for its ability to displace the antigen as measured by FACS release and by release of cells bound to magnetic beads, or by biospecific interaction analysis (BIAcore™, Pharmacia).

An exemplary method for identifying a peptide useful for releasing a cell bound by a specific monoclonal antibody comprises coating a solid support with a biotinylated or non-biotinylated form of the antibody, contacting the antibody with a plurality of peptides of a random peptide library, selecting at least one peptide which specifically binds to the antibody, contacting the antibody bound to the target cell with the selected peptide, and determining the ability of the selected peptide to detach the antibody from the target cell, thereby releasing the target cell.

DETAILED DESCRIPTION OF THE INVENTION

Figure 1:
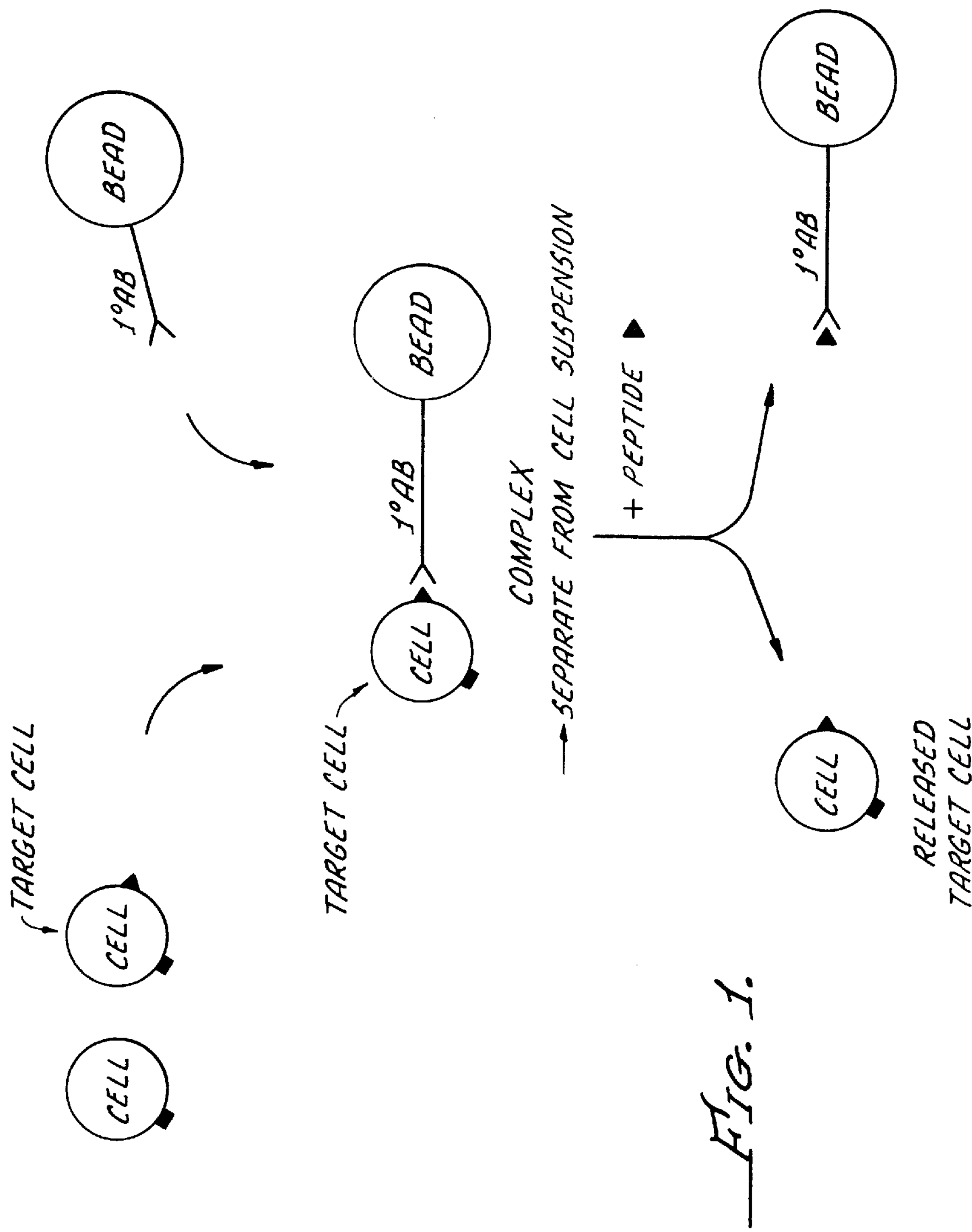
FIG. 1 depicts a method for positive cell selection whereby a target cell is bound to a primary antibody and a cell separation means, separated from the cell suspension, and then contacted with a specific peptide which binds to the primary antibody and thereby releases the target cell.

The invention provides methods and peptide compositions for the positive and positive/negative selection of target cells from a heterogeneous cell suspension. The methods are based on the identification of specific peptides which effect the displacement and release of a specific target cell from a specific monoclonal antibody. The peptide-mediated release is enzyme-free, and thus leaves the cell surface proteins intact. Moreover, peptide-mediated release leaves the target cell free of bound antibody or antibody fragments.

The general method of the invention entails forming within a heterogeneous cell suspension a complex comprising the target cell, a monoclonal primary antibody bound to a cell surface protein on the target cell, and a cell separation means linked to the primary antibody and thus to the target cell. The complex is then separated from the cell suspension, and contacted with a specific peptide which binds to the primary antibody, thus displacing and releasing the target cell from the primary antibody and the cell separation means. The cell separation means linked to the antibody is then separated from the released target cell by conventional means.

Herein the term "contacting" refers to bringing into close proximity the peptide and the antigen/antibody complex such that weak intermolecular forces may be disrupted.

Herein the term "binding" or "binds" refers to the binding of antibody to antigen by a combination of relatively weak non-covalent forces, including hydrophobic and hydrogen bonds, van der Waals force, and ionic interaction. The affinity of antibody-antigen binding is in the range of $5\times10^4$ to $10^{12}$ liters per mole, more usually $10^6$–$10^9$ l/M (Alberts, B., et al., Eds., *Molecular Biology of the Cell*, Garland Publishing, New York and London, 1983, p.969–970).

Herein the term "displace" refers to the peptide of the invention causing the antibody to become unbound from its cognate antigen by interruption of the weak non-covalent binding forces described above.

Herein the term "release" refers to the cell being unbound from the antibody/solid support, thereby leaving the cell free to flow with the elution fraction from a separation system.

It is possible that the peptide of the invention acts as an "epitope-mimicking" peptide, thus competing for the antigen-binding site on the antibody, and thereby displacing the antibody from its cognate antigen. The fact that the mechanism of action of the peptide of the invention is unknown does not detract from the importance and power of the invention.

Herein, the peptide of the invention preferably contains fewer than 30 amino acid residues, more preferably 4 to 20 amino acid residues, most preferably 4 to 10 amino acid residues.

In addition to the specific peptides listed and claimed below, the present invention also contemplates analogues of peptides formed by conservative amino acid substitutions, substitutions of non-natural amino acids, cyclization of peptides, and peptidomimetics modeled on identified releasing peptides.

The principle behind conservative amino acid substitution is that certain amino acid pairs have compatible side chains such that, when one is substituted for the other, there will be only minimal changes in the tertiary structure and the binding affinity of the antibody for peptide. Rules for conservative substitution are explained in Bowie, J. U., et al., *Science* 247:1306–1310, 1990.

Substitutions of non-natural amino acids: Analogues of synthetic peptides can be made by substituting individual residues with non-natural or unusual amino acids.

Sequences of bioactive peptides are originally derived from proteins which are made up of the naturally occurring twenty L-amino acid residues. However, the process of chemical synthesis used to construct synthetic peptides allows for the substitution of alternate residues including D-amino acids, infrequently occurring natural amino acids, or non-natural synthetic amino acid analogues (Bodansky, M, 1984, *Principles of Peptide Synthesis*, Springer-Verlag, Berlin). These alternate residues can be used (a) to replace chemically reactive residues and improve the stability of the synthetic peptide, (b) to provide analytic labels useful in the detection of the synthetic peptide, and (c) to modulate the bioactivity of the synthetic peptide by increasing or decreasing the binding affinity of the antibody for the peptide.

Cyclization of peptides: Analogues of synthetic linear peptides can be made by chemically converting the structures to cyclic forms. Cyclization of linear peptides can modulate bioactivity by increasing or decreasing the potency of binding to the target protein (Pelton, J. T., et al., *Proc. Natl. Acad. Sci. U.S.A.,* 82:236–239) . Linear peptides are very flexible and tend to adopt many different conformations in solution. Cyclization acts to constrain the number of available conformations, and thus, favor the more active or inactive structures of the peptide. The immunogenicity of synthetic peptides has been correlated with the experimentally observed conformational preferences in solution (Dyson, H., et al., 1988, *Annual Review of Biophysics and Biophysical Chemistry,* 17:305–324). Differences in immunogenicity may be indicative of differences in binding affinity of specific antibodies for cyclic peptides.

Cyclization of linear peptides is accomplished either by forming a peptide bond between the free N-terminal and C-terminal ends (homodetic cyclopeptides) or by forming a new covalent bond between amino acid backbone and/or side chain groups located near the N- or C-terminal ends (heterodetic cyclopeptides) (Bodanszky, N., 1984, supra). The latter cyclizations use alternate chemical strategies to form covalent bonds, e.g. disulfides, lactones, ethers, or thioethers. Linear peptides of more than five residues can be cyclized relatively easily. The propensity of the peptide to form a beta-turn conformation in the central four residues facilitates the formation of both homo- and heterodetic cyclopeptides. The presence of proline or glycine residues at the N- or C-terminal ends also facilitates the formation of cyclopeptides, especially from linear peptides shorter than six residues in length. Examples of cyclized releasing peptides are shown in Examples below.

Peptidomimetics: Peptidomimetics technology is the design of molecular mimics of peptides. The ability to successfully design such molecules depends upon the understanding of the properties of the linear peptide sequence and the conformation in which it is presented to the antibody. The synthesis of mimetics can provide compounds exhibiting greater biological activity, improved solubility, and stability (Nakanishi, H., et al., 1993, Peptidomimetics of the immunoglobulin supergene family—a review. *Gene* 137:51–56).

Herein, the term "cell separation means" refers to well-known means such as paramagnetic beads, columns, hollow fibers, glass beads, polysaccharide beads, and polystyrene tissue culture flasks. Hereinafter, the term "paramagnetic bead" or "bead" will be used to illustrate a cell separation means. However, this invention is not limited to the use of paramagnetic beads as the separation means. Paramagnetic beads are separated from cell suspensions by the use of magnets (Hardwick, R. A., et al., *J Hematotherapy* 1:379–386, 1992).

Herein the term "linked to a primary antibody" refers to any means of connecting the primary antibody to the cell separation means. Examples of linking means include:

(1) direct linkage of the cell separation means to the primary antibody by covalent bonds or adsorption;

(2) indirect linkage of the cell separation means to the primary antibody by an intervening protein which is directly linked to the cell separation means, and which also binds the primary antibody;

(3) direct or indirect linkage of the cell separation means to the primary antibody by biotin/avidin binding, wherein an antibody is biotinylated and the cell separation means comprises avidin.

One preferred method of the invention entails the use of paramagnetic beads linked to a protein means for binding the primary antibody. The protein means for binding the primary antibody can be *Staphyloccocus aureus* Protein A, Streptococcus Protein G, or an immunoglobulin which binds to the monoclonal primary antibody. The latter is known as a "secondary antibody". The secondary antibody can be a polyclonal antibody or a monoclonal antibody. A polyclonal antibody is typically raised in an animal such as a rabbit, sheep, goat, horse, pig, or bovine species. A monoclonal antibody is typically raised in a small rodent such as mouse or rat according to the basic method of Köhler and Milstein. Hereinafter, the term "secondary antibody" will be used to illustrate the protein means for binding the primary antibody.

The invention can be applied to positive selection of any type of target cell. To use the invention, it is first necessary to provide a monoclonal antibody which binds to a specific cell surface antigen on the target cell. Given a monoclonal antibody specific for the target cell, the experimental examples below can be followed to identify a specific peptide sequence which will bind to the monoclonal antibody and displace the target cell, thereby releasing the target cell from the antibody.

It is generally believed that a given monoclonal antibody binds to a small portion of its cognate antigen, known as its epitope, which consists of as few as 3–6 amino acid residues (Pellequer, J. L., et al., *Methods in Enzymology* 208:176, 1991). The amino acid residues may be in sequence, or they may be discontinuous within the antigen sequence. When the amino acid residues of the antigen sequence are discontinuous, it is thought that they are presented in close proximity for recognition by the cognate antibody through three-dimensional folding of the antigen.

To practice the invention, it is necessary to identify a specific small peptize which will displace the monoclonal antibody from its epitope on its cognate antigen. This specific peptide may be an "epitope-mimicking" peptide, which acts by direct competition at the binding site, or it may be a peptide which displaces the antibody by any other mechanism.

In order to identify small peptides which are bound by the monoclonal antibody, several initial selection techniques may be employed which select candidate releasing peptides. In the phage-display technique, large libraries of random amino acid sequences are screened in biopanning or antibody binding assays (see Example 1 below) . Examples of random peptide libraries are phage-displayed linear 6 mer and 15 mer libraries, constrained (cyclized) $XCX_6CX$ (described in Example 14 below), and a conotoxin $XCCX_3CX_5C$ library. In the "PIN" technique, random peptide libraries are displayed on isolated pins which then are screened for their ability to bind the antibody, as read out on ELISA-type assays. Random peptide libraries based on phage display or pin-peptide display are reviewed in Wells, J. A., et al., *Current Opinion in Biotechnology* 3:355–362, 1992, and in Scott, J. A., *Trends in Biochemical Sciences*, 17:241–245, 1992.

Random peptide libraries may also be screened using antibody bound to beads (see Example 13 below).

Candidate releasing peptides can also be identified by computer-assisted analysis of potential antigenic peaks in the protein antigen (see Example 11 below).

Candidate releasing peptides can also be identified by analyzing complementarity-determining regions (CDR's) in the antibody of interest. Translation of available cDNA sequences of the variable light and variable heavy chains of a particular antibody permit the delineation of the CDRs by comparison to the database of protein sequences compiled in the book *Sequences of Proteins of Immunological Interest*, Fifth Edition, Volume 1, Editors: E. A. Kabat, et al., 1991 (see table on page xvi). Studies have shown that in some cases CDR peptides can mimic the activity of an antibody molecule (Williams, W. V., et al. *Proc. Natl. Acad. Sci. U.S.A.* 86:5537, 1989). CDR peptides may bind their cognate antibody, thus effecting displacement of the antibody from the antigen. To increase the efficiency of the above procedures in identifying candidate releasing peptides, biospecific interaction analysis using surface plasmon resonance detection through the use of the Pharmacia BIAcore™ system may be utilized. This technology provides the ability to determine binding constants and dissociation constants of antibody-antigen interactions. Analysis of multiple antibodies and the number of biopanning steps (at set antibody concentrations) required to identify a tight-binding consensus peptide sequence will provide a database on which to compare kinetic binding parameters with the ability to identify tight binding peptides and their activity as competitive agents. If a particular antibody/antigen interaction is determined to be extremely tight, then the researcher may choose to work with a different antibody. The use of the BIAcore™ system requires purified antibody and a source of soluble antigen. Phage display-selected clones can be used as a source of peptide antigen and directly analyzed for antibody binding. In the present studies, CD34 antigen was obtained from detergent-solubilized CD34 protein from KG1a cells. BIAcore™ technology was also applied to anti-CD4 antibodies; in this case, the source of antigen was commercially available recombinant soluble CD4 protein (Agmed, Bedford, Mass.).

The candidate releasing peptides identified by the above described means are then screened for displacement of the antibody from the cell surface antigen, typically in assays using cells bearing the antigen.

It is thought that the specific peptide effects the displacement of the target cells by either (1) mimicking the epitope on the cell surface antigen, thereby competing against the epitope for antibody binding, or (2) binding to a site on the antibody and causing a conformational change, thus altering the antibody such that it can no longer bind to its epitope on the cell surface antigen. Evidence was obtained using labeled peptide and labeled antibody that at least one of the identified peptides of the invention binds to its cognate antibody (data not shown). The methods of the invention can identify a specific peptide that acts to release the target cell by any mechanism. Herein, the term "peptide which binds to a monoclonal antibody bound to a cell surface antigen on a target cell, displacing the antibody from the cell surface antigen, and releasing the target cell from the antibody" refers to a peptide which acts to release the target cell by any molecular mechanism.

Candidate releasing peptides can be identified by any one or several of the following means:

a) phage display of a random peptide library followed by biopanning with the antibody of interest;

b) computer-assisted analysis of potential antigenic peaks of the protein antigen of interest;

c) analysis of complementarity-determining regions (CDRs) of the antibody of interest;

d) random peptide library pin display followed by biopanning with the antibody of interest;

e) theoretical molecular modeling of three-dimensional antibody structure.

Once a candidate peptide has been identified, its ability to displace the antigen is tested by incubating the peptide with cells bound by the antibody. Release of cells from antibody is typically determined by FACScan or release from magnetic beads.

One type of random peptide library which can be used in the practice of the invention is the hexapeptide phage display library described by Scott and Smith (Science 249:386–390, 1990). Prior to the present invention, it was believed that a monoclonal antibody would have to be biotinylated in order to bind tightly to an avidin coated plate to yield a sufficient signal to identify a peptide which binds to the antibody. However, it was also known that many monoclonal antibodies cannot be biotinylated without diminishing or destroying their binding functions. Fortunately, it was discovered that a biopanning technique using a non-biotinylated monoclonal antibody (see Example 1 below) can yield a sufficient positive signal for the identification of candidate peptides useful for detaching the antibody from its cognate antigen on the surface of the target cell.

The following describes exemplary methods for identifying a specific peptide useful for the release of a target cell bound by a specific monoclonal antibody. The methods involve first coating the monoclonal antibody onto a plastic plate so that the antibody attaches to the plate. In the case of the non-biotinylated monoclonal antibody, the antibody binds to the plastic by non-specific interactions, thought to be electrostatic interactions. Alternatively, the monoclonal antibody may be biotinylated and then attached to an avidin-coated plate by exploiting the tight binding of avidin to biotin. Yet another scheme makes use of Protein A or Protein G coated plates; it is well known that Protein A and Protein G, from Staphyococcus and Streptococcus organisms, bind relatively tightly to certain immunoglobulin isotypes such as IgG and IgM. As an alternative to plates, beads can be used as the solid support for the monoclonal antibody; antibody is coated onto or bound to beads using the same methods as for coating on plates. Once the monoclonal antibody has been coated onto the plate or beads, the attached antibody is contacted with a plurality of phage displaying a random peptide library, and then the non-bound phage are rinsed away. The bound phage are then eluted, grown, and amplified. This process is known as "biopanning". Several rounds of biopanning are preferred to select for the peptides which bind the antibody most effectively. Ultimately, the phage DNA encoding the selected peptides is subjected to DNA sequence analysis to determine the candidate peptides for release of target cells.

Then the candidate peptides are synthesized by conventional means. To increase solubility of the peptides, they may be synthesized with additional flanking sequences of hydrophilic amino acid residues, typically residues of amino acids which are polar or charged. The candidate peptides are then tested for their ability to displace the antibody from its cognate antigen on the surface of the target cell. It is understood that the mere fact that a peptide is bound by the antibody does not ensure that the peptide would displace the antigen. A candidate peptide might be bound less tightly by the antibody than the antigen is bound, thus the peptide might not compete successfully for binding and would not displace the antibody from its cognate antigen. Another way of expressing this problem is that the antibody might have greater affinity for its cognate antigen than it has for the candidate peptide. It is also very likely that a candidate peptide could bind an antibody without interfering with or binding to its antigen binding site (epitope). Fortunately, it was discovered that this method of the invention can successfully identify peptides which not only bind to the antibody, but also displace the antibody from its cognate antigen, thereby releasing the target cell from the antibody.

Once the appropriate peptide has been identified and synthesized, the positive selection and positive/negative selection methods of the invention can be practiced.

As depicted in FIG. 1, within the cell suspension a complex is formed comprising the target cell bound to a primary antibody, which in turn is linked to a cell separation means, preferably a paramagnetic bead. The complex is separated from the cell suspension by conventional means, preferably a magnet. The primary antibody within the separated complex is then contacted with a specific peptide which binds to the primary antibody and displaces the antibody from the target cell, thereby releasing the target cell from the complex. The paramagnetic bead linked to antibody is then separated from the released target cell, yielding a purified target cell with its cell surface proteins intact, and without antibody or antibody fragments bound to its surface.

Figure 2:
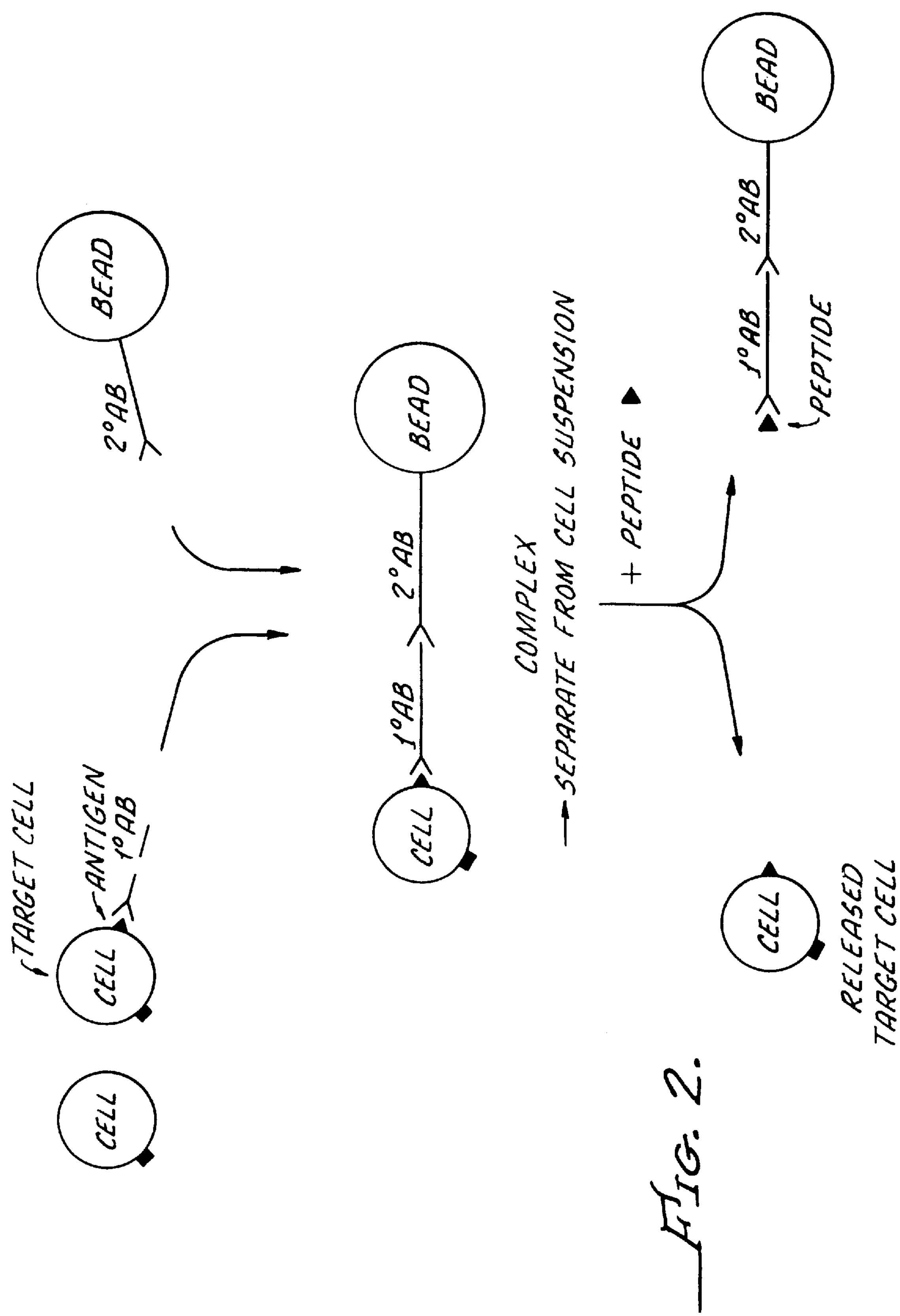
FIG. 2 depicts a preferred method for positive selection wherein the primary antibody is linked to the cell separation means by a secondary antibody.

A preferred embodiment of the invention is depicted in FIG. 2. In this embodiment, the primary antibody is not directly coupled to the bead, but rather is linked to the bead by a secondary antibody, which in turn is coupled to the bead to form the complex. As in FIG. 1, the complex is separated from the cell suspension and contacted with the specific peptide, thereby releasing the target cell.

Figure 3A:
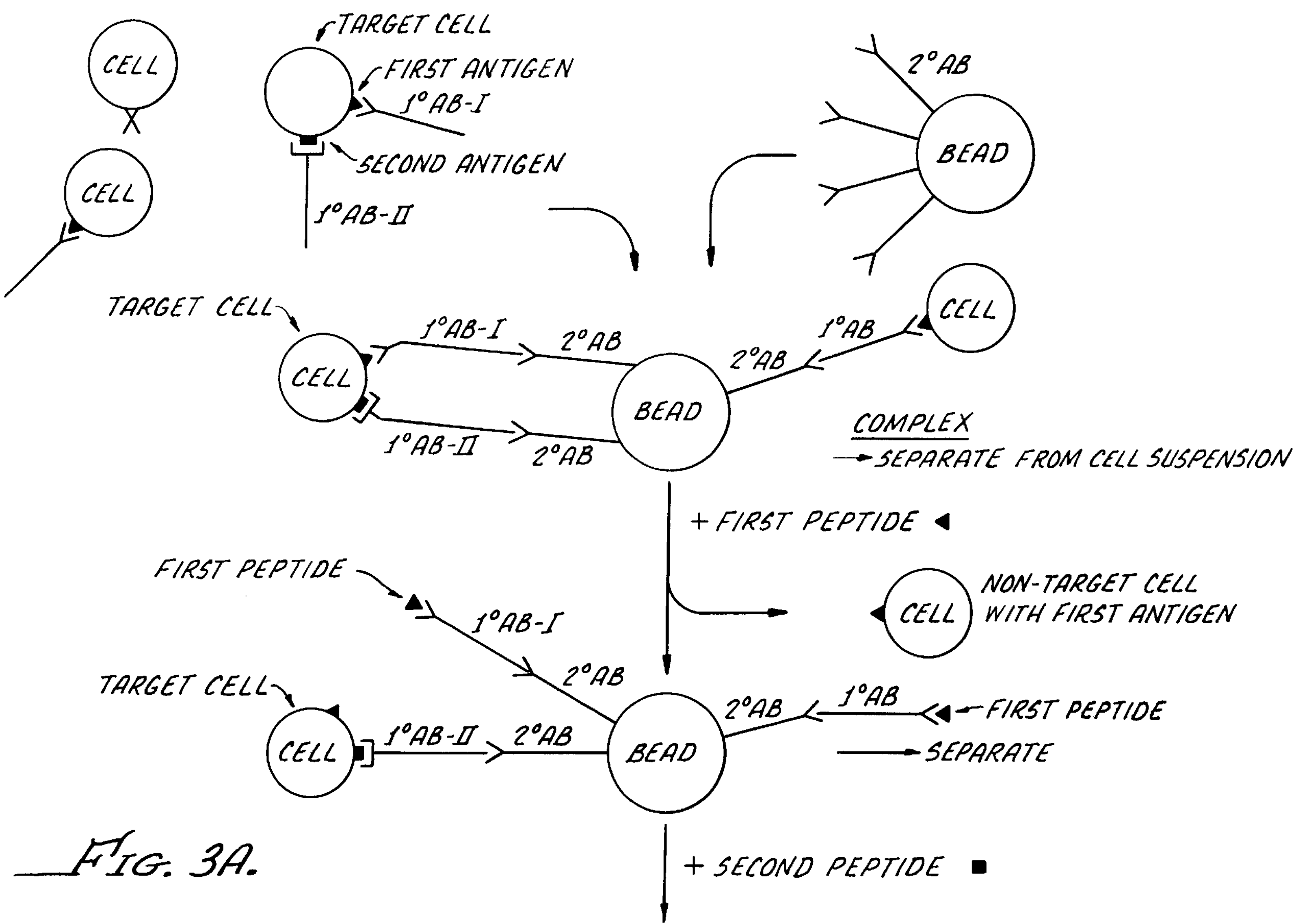
FIGS. 3A and 3B depict a method for double positive cell selection and release whereby a target cell with two desired antigens is separated from a heterogeneous cell suspension and then released by incubation with two specific peptides.
Figure 3B:
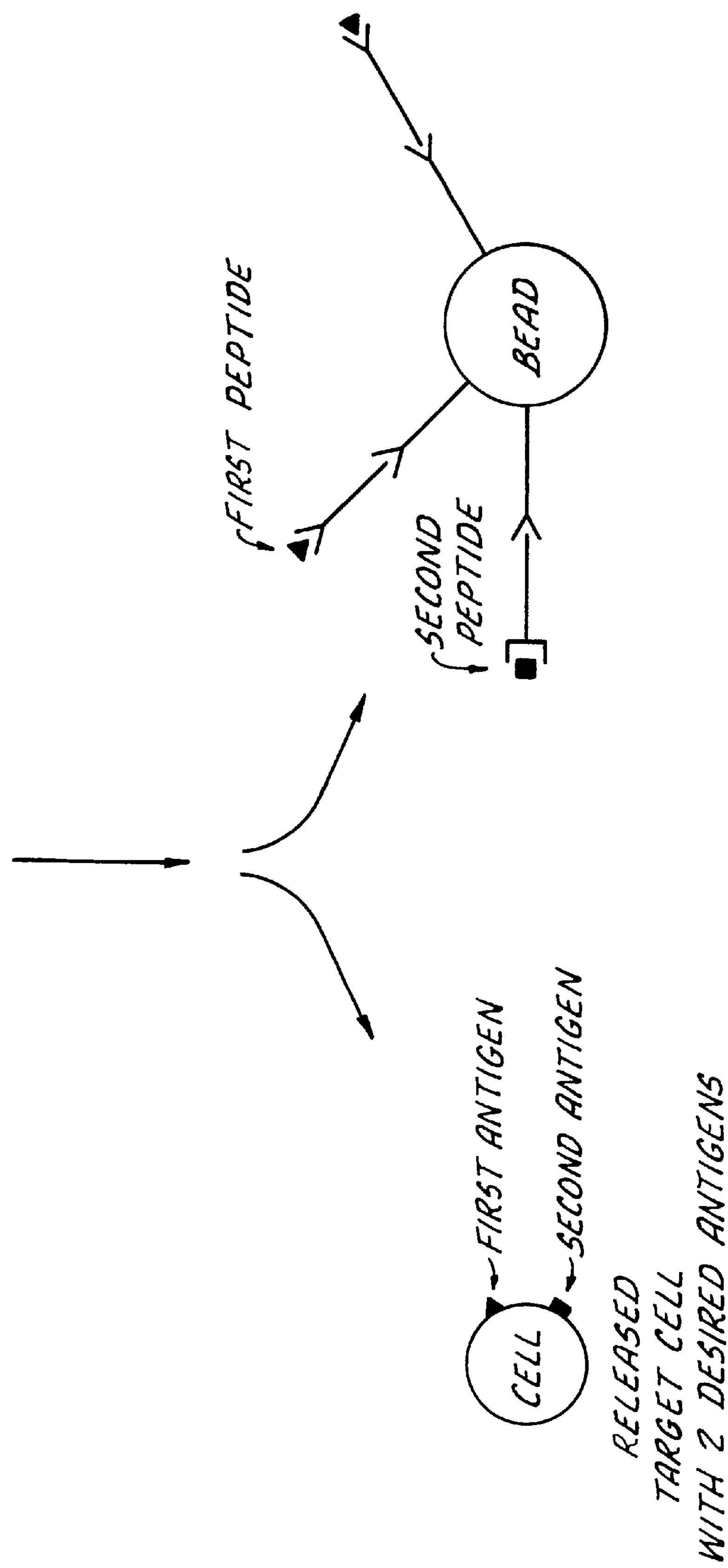

Another embodiment of the invention is depicted in FIGS. 3A and 3B (Double Positive Cell Selection), whereby a target cell bearing two different antigens is positively selected from a heterogeneous cell suspension containing non-target cells bearing only one of the antigens. The cell suspension is incubated with first and second primary antibodies, each of which binds to only one of the two different antigens on the target cell. A complex is formed by adding to the cell suspension a paramagnetic bead coupled to a secondary antibody which binds to both primary antibodies. The complex is separated from the cell suspension and then contacted with a specific peptide which binds to the first primary antibody, thereby releasing the cell which bears the first antigen but not the second antigen. This cell is separated from the remaining cell-antibody-bead complex. The remaining target-cell-antibody-bead complex is then contacted with a second specific peptide which binds to the second primary antibody, thus displacing the target cell from the second primary antibody and releasing the target cell from the bead. This process provides for the sequential positive selection of two different cell types from a heterogeneous cell population.

Figure 4:
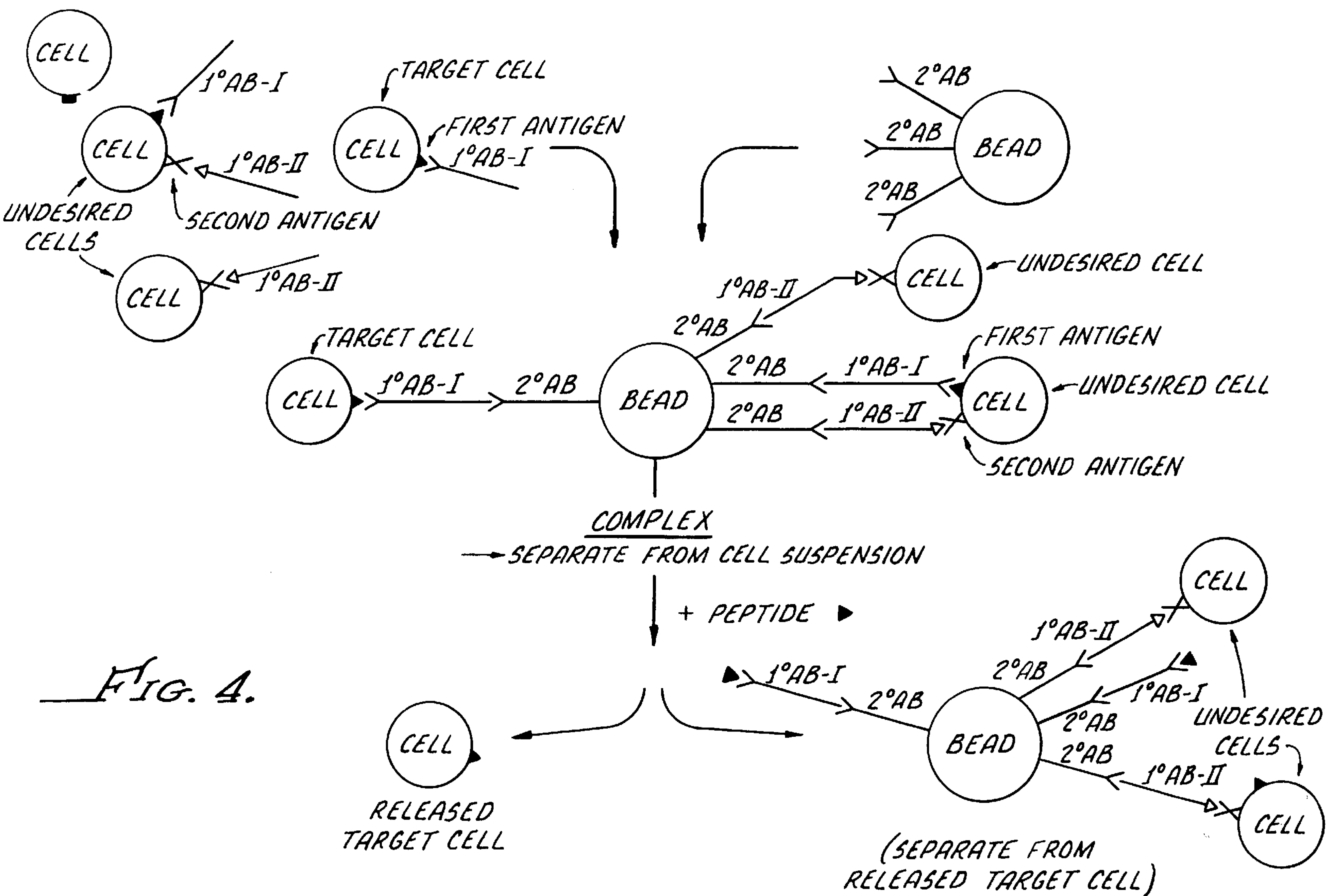
FIG. 4 depicts a method for positive/negative cell selection whereby a target cell bearing a desired first antigen is selected from a heterogeneous cell suspension containing undesired cells bearing a second, undesired antigen. By this method, target cells may also be separated from undesired cells which bear both the desired first antigen and a second, undesired antigen.

Another embodiment of the invention is depicted in FIG. 4 whereby a target cell bearing a first antigen is positively selected from a heterogeneous cell suspension which also contains undesired cells bearing the first antigen as well as a second antigen (Positive/Negative Selection). The positive/negative selection method of the invention is also useful for removing contaminating, undesired cells which do not bear the first antigen, but only a second antigen. Positive/negative selection is especially desirable when, for instance, autologous CD34+ cells are to be selected from blood or bone marrow of a cancer patient. The selected CD34+ cells are destined for re-infusion to the patient to reconstitute his bone marrow after high-dose chemotherapy or radiation. Positive selection of CD34+ cells alone is thought to reduce the tumor burden in the selected cell sample by several logs. However, it would be most desirable to negatively select against cancer cells as an added precaution against the possibility that reinfused cancer cells might contribute to relapse. Positive/negative cell selection can be conducted either simulataneously (concomitantly) or sequentially.

Simultaneous positive/negative cell selection:

Within the cell suspension a complex is formed which comprises the target cell bound to a first primary antibody, which is linked to a bead, which in turn is linked to a second primary antibody bound to an undesired cell. For example, the first primary antibody can be an anti-CD34 antibody, whereas the second primary antibody can be an anti-B cell antibody, or a mixture of several antibodies against undesired cell types. Anti-B cell antibodies are especially useful in purging of positively selected CD34+ cell populations from patients with B-cell lymphomas. The complex is separated from the cell suspension, and then contacted with a specific peptide which binds to the first primary antibody, thereby displacing the first primary antibody from its cognate antigen on the target cell surface and releasing the target cell from the complex. The undesired cell, however, remains bound to the bead via the second primary antibody. Thus, the undesired cell can be separated from the released target cell, yielding a purified population of target cells separated from undesired cells.

Sequential positive/negative cell selection:

In this method, the positive selection step is conducted first as described above, using only the antibody against the desired antigen (for instance CD34) and release by a specific peptide. The positively selected cells retain antigens on their surfaces due to the non-enzymatic peptide-mediated release, making a subsequent selection step possible. The positively selected cells are then incubated with the second primary antibody or mix of antibodies directed against undesired antigens such as B-cell antigens. The cells bound by the second primary antibody(s) are captured by conventional means, and the unbound cells are collected for reinfusion to the patient.

Positive/negative selection is especially important for the further purification of positively selected CD34+ cells. Typically, the positively selected CD34+ population will be over 90% pure, which represents a 3 log depletion of B cells, for instance (see Example 19 below). Addition of a negative selection step further depletes undesired cells up to a 4 log depletion or greater. The negative selection step is known as "purging". Negative selection can be optimized so that the resulting cell composition is substantially free of undesired cells. The term "substantially free" of undesired cells means that no undesired cells are detected using standard sampling and analysis by, for instance, immunocytochemistry, morphology, or FACScan™.

The negative selection technique can be used also for depletion of T lymphocytes from allografts, thus greatly reducing the risk of graft-versus-host disease (GVHD).

The extent of depletion of undesired cells is dependent on, among other factors, the antibody/bead/cell/peptide ratios utilized. These ratios can be optimized to yield the desired log depletion of, for instance, B cells or T lymphocytes. In some applications, it may be desirable to retain a few tumor lymphocytes in the purified CD34+ population for reinfusion to the patient in order to elicit tumor-versus-leukemia reaction whereby the reinfused tumor cells mobilize the patient's immune system against residual tumor cells (wingard, J. L. 1995, IBC 2nd Annual Conference on Hematopoietic Stem Cells, San Diego, Calif.). However, a 3–4 log reduction in tumor cells reinfused to the patient is expected to reduce incidence of relapse.

Experimental Examples 1–7 below describe the identification and use of specific peptides for the release of human hematopoietic stem cells bound by the anti-CD34 mouse monoclonal antibody produced by the hybridoma designated ATCC HB 11646, known herein as antibody 9069. The hybridoma ATCC HB 11646 has been deposited under the provisions of the Budapest treaty with the American Type Culture Collection, Rockville, Md., USA. The following will illustrate the methods of the invention by describing the use of these peptides to positively select human hematopoietic stem cells from a heterogeneous cell suspension such as bone marrow or peripheral blood.

A heterogeneous cell suspension of human bone marrow, peripheral blood, or cord blood contains a very small number of stem cells (typically 0.2 to 2.0%). The stem cells are target cells which are to be positively selected for further use such as in vitro culture or reinfusion to a patient.

Human hematopoietic stem/progenitor cells are so named because they have the capacity to proliferate many times over, and to differentiate into all hematopoietic cells types. Hereinafter, the term "stem cells" refers to human hematopoietic stem/progenitor cells. Stem cells bear a characteristic cell surface antigen known as CD34. Several monoclonal antibodies have been produced which specifically bind to CD34. It is assumed that each monoclonal antibody binds to a different epitope on the CD34 antigen, since it is statistically very unlikely that several different monoclonal antibodies would be produced against the identical epitope. Thus, a peptide identified as effective for displacing a given anti-CD34 monoclonal antibody is likely to displace only this specific antibody, and not other monoclonal anti-CD34 antibodies.

As depicted in FIG. 2, within the suspension of blood or bone marrow, a complex is formed comprising human stem cells which are bound by the mouse monoclonal antibody 9069 (1° AB), which is in turn bound by a sheep-anti-mouse antibody (2° AB), which is coupled to a paramagnetic bead. The complex is separated from the cell suspension by magnetic means. Then the 9069 antibody (°1 antibody) is contacted with a specific peptide which binds to the 9069 antibody and displaces it from the CD34 antigen on the stem cell, thereby releasing the stem cell. The paramagnetic bead linked to the sheep anti-mouse antibody and the 9069 antibody is then separated from the released stem cell using a magnetic means. This provides a highly purified suspension of stem cells with their surface proteins intact, including the CD34 antigen protein. Moreover, the stem cell does not have residual antibody or antibody fragments bound to its surface.

The invention also provides a method for positive/positive cell selection whereby two desired target cells can be positively selected from blood or bone marrow. For instance, it may be desirable to positively select both stem cells and T-lymphocytes. T-lymphocytes bear the cell surface antigen known as CD3. Specific subsets of T-lymphocytes bear cell surface antigens known as CD4 and CD8. A monoclonal antibody against the desired class of T-lymphocyte can be provided and used to screen peptide libraries as described in Example 1 below. A specific peptide which displaces the anti-T-lympocyte antibody is selected and used in conjunction with a peptide that displaces the anti-CD34 antibody. Thus, both the anti-CD34 antibody and the anti-T-lymphocyte antibody are incubated with the cell suspension, and the two types of target cells are bound by their specific primary antibodies. The primary antibody-bound cells are bound to secondary antibodies coupled to beads, they are separated from the cell suspension, and then displaced from the beads by contact with the two specific peptides. Thus, a substantially pure suspension of stem cells and T-lymphocytes is obtained. As depicted in FIGS. 3A and 3B, the invention provides a method for double positive cell selection whereby, for instance, a subset of CD34+ cells bearing other cell surface markers may be positively selected.

As depicted in FIG. 4, the invention also provides a method for positive/negative cell selection whereby target CD34+ cells may be positively selected from a suspension of blood or bone marrow which also contains undesired CD34+ cells which bear a second antigen such as a tumor marker. For a number of different types of cancer, it would be desirable to perform autologous stem cell transplant following high-dose chemotherapy or radiation to replenish the hematopoietic cells of the bone marrow which are destroyed by such treatments. However, the use of autologous stem cell transplant would involve harvesting a portion of the patient's bone marrow or peripheral blood prior to treatment, and there is a risk that the bone marrow might harbor tumor cells which would then proliferate when they were reinfused to the patient. The addition of a negative purging step allows removal of any autologous tumor cells non-specifically captured in the positive selected fraction. The types of cancer for which autologous bone marrow transplant would be indicated include neuroblastoma, breast carcinoma, small cell lung carcinoma, and colon carcinoma. The positive selection of CD34+ cells reduces the risk of transfer of cancer cells because it is believed that very few or no CD34+ cells are metastatic tumor cells. However, a higher degree of confidence can be attained through the use of positive/negative cell selection.

There are several cell surface antigens identified as indicative of the tumorous nature of a cell, and antibodies are available which bind to these tumor antigens. For instance, to select against neuroblastoma cells, antibodies against the following antigens can be used: $G_{D2}$, NCAM, 459, HSAN, UJ13A, and UJ167.11 (In: *Bone Marrow Processing and Purging*, Ed. Adrian P. Gee, CRC Press, Boca Raton, Florida, 1991.) To select against breast carcinoma cells, a panel of antibodies which bind to a wide range of breast antigens can be used. Likewise, to select against small cell lung carcinoma cells, a panel of antibodies directed against neural, epithelial, and neuroendocrine antigens can be used. The carcinoembryonic antigen (CEA) is present on a wide variety of breast and colon cancer cells, and antibodies against CEA are useful in selecting against these tumor cell types.

As depicted in FIG. 4, within a suspension of bone marrow or blood from a cancer patient is formed a complex comprising the target CD34+ stem cell, the 9069 anti-CD34 antibody (°1 AB-I), the sheep anti-mouse antibody (2° AB), a bead, the second primary antibody or panel of antibodies directed against tumor antigen(s) (1° AB-II), and the undesired cell, which may or may not also bear the CD34+ antigen. The complex is separated from the suspension and contacted with a specific peptide which binds to the 9069 antibody, displacing the 9069 antibody from the CD34 antigen, and thus releasing the target stem cell from the complex. The bead bound to the antibodies and the undesired cell is then separated from the released stem cell, yielding a purified suspension of CD34+ stem cells which has been purged of cells bearing the tumor antigens.

Any of the above described selection methods may be used to positively select human hematopoietic CD34+ cells by binding the stem cells with the 9069 antibody produced by ATCC HB 11646, and then releasing the stem cells by contacting the 9069 antibody with a peptide selected from the list below. Herein, peptide sequences are shown in the one-letter amino acid symbols recommended by the IUPAC-IUB Biochemical Nomenclature Committee (see PatentIn User Manual of the U.S. Patent and Trademark Office, November 1990, page 101).

I. Q G $X_1$ F (SEQ ID NO:1)

and

II. $X_2$ Q G $X_1$ F $X_3$ (SEQ ID NO:2)

wherein $X_1$=W, Y, S, F or T; $X_2$=Q, N, T, or S; and $X_3$=P, W, or S;

and

| | | |
|---|---|---|
| III. | Q G X F | (SEQ ID NO: 3) |
| IV. | $J_1$ Q G X F $J_2$ | (SEQ ID NO: 4) |
| V. | X Q G X F X | (SEQ ID NO: 5) |
| VI. | $J_1$ X Q G X F X $J_2$ | (SEQ ID NO: 6) |
| VII. | $J_1$ Q Q G W F P $J_2$ | (SEQ ID NO: 7) |
| VIII. | $J_1$ T Q G S F W $J_2$ | (SEQ ID NO: 8) |
| IX. | $J_1$ Q Q G W F P K D $J_2$ | (SEQ ID NO: 9) |
| X. | $J_1$ Q Q G W F P D K $J_2$ | (SEQ ID NO: 10) |
| XI. | $J_1$ A D G A X Q G X F X G A K D $J_2$ | (SEQ ID NO: 11) |
| XII. | $J_1$ A D G A Q Q G W F P G A K D $J_2$ | (SEQ ID NO: 12) |
| XIII. | $J_1$ A D G A T Q G S F W G A K D $J_2$ | (SEQ ID NO: 13) |
| XIV. | $J_1$ N S S V Q S $J_2$ | (SEQ ID NO: 14) |
| XV. | $J_1$ A D G A L I S Q V S G A K D $J_2$ | (SEQ ID NO: 15) |
| XVI. | $J_1$ L I S Q V S $J_2$ | (SEQ ID NO: 16) |
| XVII. | $J_1$ N S S V X X $J_2$ | (SEQ ID NO: 17) |
| XVIII. | $J_1$ N S S V G L $J_2$ | (SEQ ID NO: 18) |
| XIX. | $J_1$ T G Q A S T $J_2$ | (SEQ ID NO: 19) |
| XX. | $J_1$ A D G A P F W G Q Q G A K D $J_2$ | (SEQ ID NO: 20) |
| XXI. | $J_1$ A D G A T Q G T F S G A K D $J_2$ | (SEQ ID NO: 21) |
| XXII. | $J_1$ P E L P T Q G T F S N V S K E $J_2$ | (SEQ ID NO: 22) |
| XXIII. | $J_1$ A D G A T Q G I C L G A K D $J_2$ | (SEQ ID NO: 23) |
| XXIV. | $J_1$ E V K L T Q G I C L E Q N K T $J_2$ | (SEQ ID NO: 24) |
| and | | |
| XXV. | $J_1$ A D G A N Q G Y G P G A K D $J_2$ | (SEQ ID NO: 25) |

wherein $J_1$ and $J_2$ are selected from the group consisting of 0–6 amino acid residues. Suitably, $J^1$ and $J_2$ contain hydrophilic, polar, or charged amino acid residues to aid the solubility of the peptide in aqueous solution. Examples of hydrophilic, polar, or charged amino acids are: G, S, T, C, Y, N, Q, D, E, H, K and R.

Any of the above listed peptides can have an amino terminal amino acid residue which is acetylated. Also, any of the above listed peptides can have a carboxy terminal amino acid residue which is amidated.

The invention also provides peptides which can release cells bound by the anti-CD34 antibody designated 9079, which is produced by the hybridoma deposited under the Budapest treaty with the ATCC, designated ATCC HB-11885, effective May 9, 1995. The following peptides are 9079-releasing peptides:

PGSPLG-KD (SEQ ID NO:26)

YSRLGF-KD (SEQ ID NO:27)

QYTQPK-D (SEQ ID NO:28)

NLQGEF-KD (SEQ ID NO:29)

RSFYYR-D (SEQ ID NO:30)
IQEFGV-KD (SEQ ID NO:31)
SFRVGY-KD (SEQ ID NO:32)
KD-VYSLWP-KD (SEQ ID NO:33)

The invention also provides peptides which can release cells bound by the anti-CD34 antibody designated 561, commercially available from Dynal, Oslo, Norway. The following peptides are linear 561-releasing peptides:

| Designation | Sequence | |
|---|---|---|
| 561A | R H R H R H | |
| 561B | K R H K R H | (SEQ ID NO: 35) |
| 561C | R T K T R F | (SEQ ID NO: 36) |
| 561D | T R V P P R | (SEQ ID NO: 37) |
| 561E | R H R P R H | (SEQ ID NO: 38) |
| 561CDR1H | D-N Y W M Q-K | (SEQ ID NO: 39) |
| 561CDR2H | A I Y P G D G D T R Y T Q K F K V | (SEQ ID NO: 40) |
| 561CDR3H | N D G Y F D A M D Y | (SEQ ID NO: 41) |
| 561CDR1L | D-S A S S S V T F M H-K | (SEQ ID NO: 42) |
| 561CDR2L | D T S K L A S | (SEQ ID NO: 43) |
| 561CDR3L | D-Q Q W N S N P L T-K | (SEQ ID NO: 44) |
| 561CDR1H.2 | D-N Y W M Q -K D | (SEQ ID NO: 45) |
| 561CDR1L.2 | K D - S A S S S V T F M H -K D | (SEQ ID NO: 46) |
| 561CDR3H.2 | A R N D G Y F D A M D | (SEQ ID NO: 47) |
| 561CDR2L.2 | H D T S K L A S Q V - D | (SEQ ID NO: 48) |
| 561L | T C T N C H - K D | (SEQ ID NO: 49) |
| 561M | A C K W C R | (SEQ ID NO: 50) |
| 561P | Q K T D A Y - K D | (SEQ ID NO: 51) |
| 561Q | K D - P A N V S L - K D | (SEQ ID NO: 52) |
| 34L | K D - P A N V S T - K D - C | (SEQ ID NO: 53) |
| | T C K W C R | (SEQ ID NO: 54) |
| | R V S W C R | (SEQ ID NO: 55) |
| | T C T N C H | (SEQ ID NO: 56) |
| | T C T K V H | (SEQ ID NO: 57) |
| | F F R D V Y | (SEQ ID NO: 58) |
| | F L H E C Y | (SEQ ID NO: 59) |
| | Y I K G L F | (SEQ ID NO: 60) |
| | Y I G T D H | (SEQ ID NO: 61) |
| | V I M E E A | (SEQ ID NO: 62) |
| | K L I A T A | (SEQ ID NO: 63) |
| | T A A H T W | (SEQ ID NO: 64) |
| | C S L H H Y | (SEQ ID NO: 65) |
| | V L L S D N | (SEQ ID NO: 66) |
| | M V W V N N | (SEQ ID NO: 67) |
| | S W N Y T H | (SEQ ID NO: 68) |

-continued

| Designation Sequence | |
|---|---|
| R V S G V G | (SEQ ID NO: 69) |
| R V S G C R | (SEQ ID NO: 70) |
| R Y G G S F | (SEQ ID NO: 71) |
| L R K V N G | (SEQ ID NO: 72) |
| W S V Q R D | (SEQ ID NO: 73) |
| F S I G A G | (SEQ ID NO: 74) |
| S P F V T M | (SEQ ID NO: 75) |
| S W N Y T H | (SEQ ID NO: 76) |
| R V S G V G | (SEQ ID NO: 77) |
| R V S G C R | (SEQ ID NO: 78) |
| R Y G G S F | (SEQ ID NO: 79) |
| L R K V N G | (SEQ ID NO: 80) |
| W S V Q R D | (SEQ ID NO: 81) |
| F S I G A G | (SEQ ID NO: 82) |
| S P F V T M | (SEQ ID NO: 83) |
| A C E W C R | (SEQ ID NO: 84) |
| A W W S N T | (SEQ ID NO: 85) |
| W C R R I T | (SEQ ID NO: 86) |
| Q K T D A Y | (SEQ ID NO: 87) |
| Q K A E A Y | (SEQ ID NO: 88) |
| Q K A D A Y | (SEQ ID NO: 89) |
| Q E T D A Y | (SEQ ID NO: 90) |
| Q E A D A Y | (SEQ ID NO: 91) |
| Q Q A D A Y | (SEQ ID NO: 92) |
| Q Q T D A Y | (SEQ ID NO: 93) |
| P A N V S L | (SEQ ID NO: 94) |
| P A D V S L | (SEQ ID NO: 95) |
| P P N V S L | (SEQ ID NO: 96) |
| T P N V S L | (SEQ ID NO: 97) |

The following are cyclic 561-releasing peptides:

| | |
|---|---|
| Q C I D E F L R C I - K D | (SEQ ID NO: 98) |
| D - Q C I D E F L R C I - K D | (SEQ ID NO: 99) |
| D - Q C I D E F L R C I - D | (SEQ ID NO: 100) |
| Q C I D E F L R C I | (SEQ ID NO: 101) |
| D C I D T F L R C V | (SEQ ID NO: 102) |
| S C I D D F L R C A | (SEQ ID NO: 103) |
| Q C I D A F R R C I | (SEQ ID NO: 104) |

-continued

| | |
|---|---|
| N C I D T F V A C A | (SEQ ID NO: 105) |
| N C I D K F L A C V | (SEQ ID NO: 106) |
| Q C I D E L L R C I | (SEQ ID NO: 107) |
| N C I D V F L T C V | (SEQ ID NO: 108) |
| D C I E R F L T C V | (SEQ ID NO: 109) |
| N C I E I F I S C V | (SEQ ID NO: 110) |
| S C I E T F L Q C V | (SEQ ID NO: 111) |
| G C I E R F F Q C V | (SEQ ID NO: 112) |

-continued

```
N C I E S F L R C V          (SEQ ID NO: 113)

S C I N R F L T C V          (SEQ ID NO: 114)

S C T N R F L T C V          (SEQ ID NO: 115)

S C P V A I A S C T          (SEQ ID NO: 116)

N C V D Q F I H C V          (SEQ ID NO: 117)

N C V E A F L I C A          (SEQ ID NO: 118)

N C V D K F L A C A          (SEQ ID NO: 119)

Q C I A E F L R C I          (SEQ ID NO: 120)

D C V E Q F L T C V          (SEQ ID NO: 121)

L C R L L K Q L C N          (SEQ ID NO: 122)

I C T D R Y P P C T          (SEQ ID NO: 123)
```

The invention also provides peptides which can release cells bound by the anti-human breast cancer antibody designated 9187, which is produced by the hybridoma deposited under the Budapest treaty with the ATCC, designated ATCC HB-11884, effective May 9, 1995. It is useful to positively select breast cancer cells from a patient's blood or bone marrow for several different techniques including culture of cancer cells to determine chemotherapeutic susceptibility, and to provide a cancer cell population for production of a patient-specific vaccine or therapeutic monoclonal antibody. Peptides which release cells bound by antibody 9187 are:

```
R W R W R H      (SEQ ID NO: 124)

A R R P R R      (SEQ ID NO: 125)

R H H L Y R      (SEQ ID NO: 126)

W Y R S H R      (SEQ ID NO: 127)

T R V P R R      (SEQ ID NO: 128)

T P R N P R      (SEQ ID NO: 129)

L R R T F W      (SEQ ID NO: 130)

L V R I Q F      (SEQ ID NO: 131)

L V R V W F      (SEQ ID NO: 132)

L T R T V F      (SEQ ID NO: 133)

R T K T R F      (SEQ ID NO: 134)
```

The compositions and methods of the invention may also be applied to epitope/antibody assays for cell quantitation. For instance, it would be valuable to have a quick, simple, and standardized assay to determine the number of CD34+ cells in a positively selected cell composition. Currently, the number of specific cells in a composition is determined by flow cytometry, which requires expensive equipment and a skilled operator.

The identification of peptide epitopes for antibodies which recognize cell surface determinants also allows construction of diagnostic cell-based assays. A peptide capable of releasing a specific cell of interest from a specific monoclonal antibody is provided. The peptide can be bound to a solid support such as a synthetic bead or immobilized to another type of solid phase, to construct an "artificial cell target" for antibody binding.

A standard binding curve is then established, in which decreasing amounts of the peptide/bead complex are contacted with a constant concentration of the specific monoclonal antibody. This yields a range of signal for antibody binding to bead. The signal might be generated in several ways. Conjugating the antibody, or using a secondary antibody conjugate, allows collection of a magnetic bead/peptide/antibody complex, and quantitation of the captured antibody. Alternatively, the capture of a fluorescent bead/peptide/antibody complex through the antibody molecule allows detection of captured fluorescent bead, and similar quantitation of binding.

Establishment of a standard binding curve would then allow quantitation of CD34+ cells, for instance, in a clinical sample by an indirect competition assay. This is analogous to an RIA (RadioImmunoAssay) . In this case, the addition of test material, containing an unknown concentration of CD34+ cells, would compete with antibody/bead complex formation. The degree of inhibition would then be proportional to the number of CD34+ cells in the test material. In the case of cell selection technology, a diagnostic assay of this sort which would provide an estimation of starting target cell concentration, would allow optimization of cell capture reagents and improved system performance.

Similar indirect binding assays can be performed for antibody binding on peptide epitope immobilized to a solid phase. Test material containing unknown CD34+ target cell numbers can inhibit antibody binding to a solid phase and a concentration determined following establishment of a control standard curve. The value of a solid phase assay is its adaptibility to a rapid read out system. For example, diagnostic systems which deliver electronic signal proportional to antibody binding have been developed, and this might allow an in-line quantitation of target cell concentration tied to cell selection hardware. Again, a diagnostic assay of this sort would provide an estimation of starting target cell concentration, allowing optimization of cell capture reagents and improved system performance.

The following experimental examples are offered by way of illustration and are not intended to limit the scope of the invention.

EXAMPLE 1

Selection of Peptide epitope displayed phase with hiqh affinity binding to anti-CD34 monoclonal antibody.

Monoclonal anti-CD34 antibodies (mouse) designated "9069" were produced by standard methods from hybridomas obtained from Baxter-Hyland (Lansdorp clone 9.C.5, Terry Fox Laboratories and Becton-Dickinson). The hybridoma which produces antibody 9069 is deposited under the terms of the Budapest treaty with the American Type Culture Collection, Rockville, Md., USA.

Specific hexamer peptide sequences were selected for their binding capacity to the anti-CD34 antibody, 9069. An epitope phage display library was obtained from and screened following the procedure of George Smith at the University of Missouri with specific modifications. The production and amplification of the epitope phage display library is described by George P. Smith in *Science,* 228:1315–1316, 1985, and described in further detail in *Cloning in fUSE Vectors*, editions of Feb. 10, 1992.

Prior to the present invention, it was generally believed that it was necessary to use a ligand in biotinylated form in order to bind the ligand firmly to avidin in a culture plate so that the phage particles would bind specifically to the ligand. However, it was known that biotinylation of the ligand of interest in this case, antibody 9069, would adversely affect its binding capacity. Fortunately, a method using a non-biotinylated form of 9069 was found to bind specific peptides with sufficient specificity to allow identification of the appropriate peptides.

Onto the bottom of a 35 mm polystyrene petri dish (Falcon) was pipetted 1 ml of 9069 antibody solution consisting of 900 μl water and 100 μl of filter-sterilized 1 M $NaHCO_3$ (unadjusted pH 8.6) containing 10 μg or 1 μg of antibody 9069. The plate was incubated overnight at 4° C. The plate was then washed with TBS/TWEEN (50 mM Tris pH 7.5/150 mM NaCl) and incubated with a blocking solution containing bovine serum albumin (BSA) for 2 hours at 4° C. The plate was again washed, and the phage was added. Typically, the input phage was 100 μl of the amplified eluate. The plate containing bound 9069 antibody and phage was incubated for 4hr at 4° C., and then washed 12× with TBS/TWEEN. The bound phage was eluted by adding 400 μl elution buffer (0.1 N HCl, pH adjusted to 2.2 with glycine, plus 1 mg/ml BSA) and gently rocking the plate for about 10 minutes. The eluate was then pipetted into a 500 μl microfuge tube containing 75 μl 1 M Tris.HCl, pH 9.1, to yield a final pH of 7–8.5. The eluate was then concentrated using a 30 kD Amicon™ filter. The concentrated eluate was used to infect K91 Kan starved cells for 30 minutes at room temperature. The production of gpIII was induced by addition of 0.2 μg/ml Tet-NZY for 60 minutes at 37° C. The phage were then grown and amplified overnight at 37° C. The phage were harvested and subjected to two rounds of polyethylene glycol (PEG) precipitation. Serial dilutions were made and both input and output phage were titered. Three more rounds of biopanning and titering were conducted. After the fourth round of biopanning and titering, 100 clones were selected and grown overnight at 37° C. The supernatant was collected and subjected to two rounds of PEG precipitation, followed by one round of acetic acid precipitation.

Four biopanning steps resulted in the selection of specific antibody binding clones of which 200 were purified. Clones representing different biopanning steps were subjected to DNA sequence analysis to determine the protein coding potential of the random hexamer sequence fused to the pIII protein. Table 1 summarizes the biopanning step.

TABLE 1

Enrichment and Analysis of Phage Display Selected Clones

| Selection | Biopanning Rounds micrograms Ab | | | | No. of Clones | No. of Clones |
|---|---|---|---|---|---|---|
| Scheme | 1st | 2nd | 3rd | 4th | Purified | Analyzed* |
| A | 10 | 10 | 10 | 10 | 30 | 16 |
| B | 10 | 10 | 10 | 1 | 30 | 16 |

TABLE 1-continued

Enrichment and Analysis of Phage Display Selected Clones

| Selection | Biopanning Rounds micrograms Ab | | | | No. of Clones | No. of Clones |
|---|---|---|---|---|---|---|
| Scheme | 1st | 2nd | 3rd | 4th | Purified | Analyzed* |
| C | 10 | 10 | 1 | 1 | 130 | 39 |
| D | 20 | 20 | — | — | 10 | 10 |

*DNA sequence analysis

EXAMPLE 2

Screening of high affinity phase clones by DNA sequence analysis to determine the hexapeptide motif.

DNA templates were prepared. DNA sequence analysis was performed using an Applied Biosystems Inc. (Foster City, Calif.) 373 Automated DNA Analysis System. Cycle sequencing utilizing Taq polymerase was performed following the procedures of Applied Biosystems. Oligonucleotide primers were purchased from Operon Technologies Inc. (Alameda, Calif.).

Selected phage clones were analyzed by DNA sequence determination of the random hexamer region of the pIII gene. Specific oligonucleotide primers were designed based on the published nucleotide sequence of the bacteriophage fl (Hill, D. F., et al., *J Virology* 44:32–46, 1982). The 5' primer was from nucleotides 1533–1556 and the 3' primer the complement of nucleotides 1714–1737.

Five different hexamer sequences were expressed among the phage clones subjected to DNA sequence analysis. The sequences and the number of clones analyzed expressing each hexamer type is listed in Table 2.

TABLE 2

Table 2. Hexamer Sequences Expressed in Selected Phage Display Clones

| Hexamer Type | Hexamer Sequence | # of Clones Identified |
|---|---|---|
| I | Q Q G W F P (SEQ ID NO: 7) | 27 |
| II | T Q G S F W (SEQ ID NO: 8) | 5 |
| III | L I S Q V S (SEQ ID NO: 16) | 1 |
| IV | N S S V G L (SEQ ID NO: 18) | 1 |
| V | T G Q A S T (SEQ ID NO: 19) | 1 |

EXAMPLE 3

Demonstration of phage supernatant for ability to bind to anti-CD34 monoclonal antibody.

KG1a is a human cell line (ATCC #CCL 246.1) that expresses CD34 antigen on its cell membrane and is used as a model system for initial testing or optimization of conditions for positive selection of CD34+ cells.

Anti-CD34 antibody, 9069 (0.0125 microgram), was preincubated with phage supernatants (0, 50, or 300 microliters) prepared as in Example 1. Subsequent incubation with KG1a cells (106) was for 30 minutes at room temperature (about 22° C.). Irrelevant phage clones selected with a different anti-CD34 antibody were used as negative specificity controls. Detection of cell-bound anti-CD34 antibody was determined by addition of 10 micrograms of FITC-goat anti-mouse IgG (FITC-GAM) followed by FACScan analysis. This experiment is schematically depicted below:

KG1a Cell Assay to Test Binding of Phage Display Selected Phage Clones or Peptides to Anti-CD34 Antibody, 9069.

| 9069 AB | +KG1a cells | allow remaining 9069 AB to bind |
|---|---|---|
| + | -------premix----------------- | |
| phage clone (or peptide) | | +FITC GAM FACScan to detect cell-bound 9069 AB |

Results: Addition of selected phage clone supernatants to the anti-CD34 antibody resulted in a loss of detectable cell surface antibody binding. These results were indicated by a shift in total fluorescense from the antibody alone position of KG1a cells (the farthest right) towards the left, indicating a decrease in bound antibody. Table 3 provides a summary of two experiments testing the binding of phage display selected clones to the 9069, anti-CD34 antibody. Approximately 50–86% of total antibody binding was observed after the addition of phage supernatants expressing peptide epitopes.

TABLE 3

Table 3. Binding of 9069 Antibody to KG1a Cells in the Presence of Phage Display Selected Phage Supernatants

| | | | % Binding* | |
|---|---|---|---|---|
| Name of Clone Tested | Hexamer Type | Hexamer Sequence | Expt. 1 | Expt. 2 |
| — | — | | =100 | N.D. |
| 9069-1 | I | Q Q G W F P (SEQ ID NO: 7) | 22 | 30 |
| 9069-3 | I | Q Q G W F P (SEQ ID NO: 7) | 16 | 43 |
| 9069-16 | II | T Q F S F W (SEQ ID NO: 8) | 16 | 30 |
| 9069-141 | V | L I S Q V S (SEQ ID NO: 16) | N.D. | N.D. |
| 9079-9 | irrelevant | N.D. | N.D. | 100 |

Subsequent testing utilized specific peptides representing the hexamer sequences with limited flanking sequences as indicated in Table 4.

TABLE 4

Table 4. Binding of 9069 Antibody to KG1a Cells in the Presence of Phage Display Selected Peptides

| Hexamer Type | Peptide Name | Actual Peptide Sequence Tested* | % of Binding** |
|---|---|---|---|
| -- | | | 0 |
| I | 9069A | A D G A-Q Q G W F P-G A K D (SEQ ID NO: 12) | 5–12% |
| II | 9069B | A D G A-T Q G S F W-G A K D (SEQ ID NO: 13) | 2–20% |
| III | 9069C | A D G A-L I S Q V S-Q A K D (SEQ ID NO: 15) | N.D. |
| backward I | 9069D | A D G A-P F W G Q Q-G A K D (SEQ ID NO: 20) | 72% |

**Phage display peptide sequences flanking the hexamer (ADGA-[ ]-GA) were retained. Charged residues (KD) were added for solubility requirements.

The peptides were able to bind to the anti-CD34 antibody, 9069, and thus decrease the amount of KG1a cells bound with antibody.

EXAMPLE 4

Evaluation of phage display selected peptides as competitive reagents in a FACS-based KG1a cell assay.

These experiments were performed following a similar procedure to the binding experiments except that the anti-CD34 antibody, 9069, was incubated with KG1a cells first, followed by addition of peptide. The experimental outline is schematically shown below:

KG1a Cell Assay to Test for Release by Peptides of 9069 Antibody Bound to Cells.

| KG1a cells -------- | cell bound 9069 AB | +peptide | competition with bound 9069 +FITC GAM |
|---|---|---|---|
| | | detect remaining cell-bound 9069 AB | |

Anti-CD34 antibody, 9069 (0.i microgram) was incubated with KG1a cells ($10^6$) for 30 minutes at room temperature (about 22° C.). Molar excesses of $10^5$ to $10^6$ times the amount of peptide to antibody were tested for the ability to displace the prebound antibody. Peptides were incubated with the antibody-cell complexes for 30 minutes at room temperature (approximately 22° C.). Remaining bound antibody was detected using the FITC-goat anti-mouse IgG reagent described in Example 3.

Results: Table 5 lists the peptide sequences tested and the percent of inhibition of antibody binding detected. These data represent the ability of peptides to displace the prebound antibody from the KG1a cells.

TABLE 5

Table 5. Competitive Binding Analysis of Peptides

| Hexamer Type | Peptide Sequence Tested | % Inhibition of Binding |
|---|---|---|
| — | | 0 |
| I | A D G A-Q Q G W F P-G A K D (SEQ ID NO: 12) | 88–95 |
| II | A D G A-T Q G S F W-G A K D (SEQ ID NO: 13) | 72–75 |
| III | A D G A-L I S Q V S-G A K D (SEQ ID NO: 15) | 32 |
| N.D. | irrelevant | 0 |

The FACS data indicated that increasing concentrations of peptide 9069A, representing hexamer type I (see Table 4 for exact sequence), resulted in the competitive displacement of the anti-CD34 antibody, 9069. Similar results were obtained using hexamer type II (Table 4).

EXAMPLE 5

Peptide release of magnetic bead isolated CD34+ human stem cells.

Human peripheral blood samples were washed followed by isolation of mononuclear cells (MNC) on a Hypaque-Ficoll® gradient. Anti-CD34 antibody, 9069 (0.5 microgram) was added to $1\times10^6$ MNCS, followed by incubation for 30 minutes at 4° C. Three washes with RPMI, 1% HSA to remove unbound antibody were followed by the addition of sheep-anti-mouse IgG1 Fc (SAM) Dynal beads. Beads were added at a ratio of 0.5 beads per cell and incubated for 30 minutes at 4° C. Bead/cell complexes were divided and each aliquot received either none or varying concentrations of peptide. Detection of peptide-mediated release of the anti-CD34 antibody was determined by monitoring the bound and unbound bead/antibody complexes on cells. Table 6 summarizes the results.

TABLE 6

PEPTIDE MEDIATED CD34+ CELL RELEASE FROM ANTIBODY CAPTURE

| Incubation Time | Peptide Concentration (ug/ml) | | | |
|---|---|---|---|---|
| (hours) | 0 | 500 | 1500 | 3000 |
| 0 | 0% | 0% | 0% | 0% |
| 1.3 | 4% | 7% | 53% | 73% |
| 2.3 | 20% | 77% | 68% | 81% |
| 3.3 | 7% | 55% | 80% | 78% |
| 17 | 80% | 91% | 87% | 89% |

Incubation of $7.4\times10^5$ cells with anti-CD34 antibody/bead complex; % cells released measured by (released cell number)/(input bound cell number ) × 100.

As a function of concentration of 9069A peptide representing hexamer type I and time of incubation, increasing amounts of antibody was released from the cells. Concentrations of 3 mg/ml peptide resulted in approximately 70% release of the cells from the antibody in one hour.

Further experimentation was carried out essentially as described in WO 95/07466, the methods of which are herein incorporated by reference. Briefly, experiments using human mobilized peripheral blood and bone marrow were conducted essentially as described in Example 6, page 23, except that in place of desthiobiotin-conjugated antibodies, non-conjugated 9069 antibody was used, non-conjugated sheep-anti-mouse secondary antibody was used, and in place of biotin, the peptides designated in the tables were used to release the cells.

TABLE 7

Stem Cell Selection Using 9069 Peptide A

| Releasing Agent | % CD34 CELLS Negative Fraction | % CD34 CELLS Positive Fraction | % Capture | % Yield |
|---|---|---|---|---|
| Chymopapain | 2.5 | 94 | 62 | 65.9 |
| 9069 Peptide A | | | | |
| 3 mg | 2.1 | 89.6 | 67.4 | 68.2 |
| 6 mg | 2 | 89.4 | 69.6 | 67.6 |
| 0 mg | 2.3 | 65.7 | 63.9 | 13.5 |

Starting % CD34 cells in mobilized peripheral blood (Resp. Tech.) is 5.86. 1e8 Cells/Arm

TABLE 8

Stem Cell Selection Using 9069 Peptide A

| Releasing Agent | % CD34 CELLS Negative Fraction | % CD34 CELLS Positive Fraction | % Capture | % Yield |
|---|---|---|---|---|
| Chymopapain | 0.16 | 90.1 | 86.9 | 73.4 |
| 9069 Peptide A | | | | |
| 0.25 mg | 0.11 | 79.9 | 90.5 | 28 |
| 0.50 mg | 0.3 | 77.71 | 73.1 | 49.5 |
| 3.0 mg | 0.12 | 83.21 | 89.7 | 72 |

% CD34 cells in mobilized peripheral blood (starting material) is 1.05

TABLE 9

Stem Cell Selection Using 9069 Peptide A and Peptide A Short

| Releasing Agent | % CD34 CELLS Negative Fraction | % CD34 CELLS Positive Fraction | % Capture | % Yield |
|---|---|---|---|---|
| Chymopapain | 0.34 | 92.1 | 91.8 | 79.9 |
| Peptide A 2.5 mg | 0.2 | 92.1 | 94.6 | 104 |
| Shorty A 2.5 mg | 0.23 | 91.6 | 94.4 | 92.9 |

% CD34 cells in bone marrow sample (starting material) is 3.66.

In Tables 9 and 10, the peptide designated "Peptide A Short" or "Shorty A" is the peptide designated "9069N" in Table 11 below.

TABLE 10

| | % CD34 CELLS | | | |
|---|---|---|---|---|
| Releasing Agent | Negative Fraction | Positive Fraction | % Capture | % Yield |
| Chymopapain | 0.12 | 79.73 | 86.7 | 68 |
| Pep. 9069A short | | | | |
| ROTATOR | | | | |
| 0.5 mg/15 min | 0.45 | 58.64 | 47.7 | 48.3 |
| 1.0 mg/15 min | 0.12 | 61.57 | 87.2 | 44.9 |
| 2.0 mo/15 min | 0.18 | 69 | 80.9 | 51.2 |
| 0.5 mg/30 min | 0.19 | 59.7 | 77.6 | 65 |
| NUTATOR | | | | |
| 0.5 mg/15 min | 0.15 | 76.53 | 80.4 | 49.9 |
| 1.0 mg/15 min | 0.13 | 63.19 | 86.9 | 77.6 |
| 2.0 mg/15 min | 0.11 | 71.5 | 88.2 | 69.4 |
| 0.5 mg/30 min | 0.09 | 63.54 | 90.5 | 67.3 |

% CD34 cells in mobilized peripheral blood (starting material) is 0.68

CD34+ cells were also isolated from human mobilized peripheral blood using the automated cell separation apparatus described in U.S. Pat. No. 5,536,475 and the method essentially as described in WO 95/24969 Both U.S. Pat. No. 5,536,475 and WO 95/24969 are herein expressly incorporated by reference. Chymopapain was used as the control releasing agent, and 25 mg of the peptide 9069N (Table 11) was used as the test releasing agent.

Results: The purity of the positively selected CD34+ cells was greater than 90% for both the chymopapain and peptide released cells. In a first experiment, the peptide release method yielded $14\times10^6$ cells, while the chymopapain release method yielded $20\times10^6$ cells. In a second experiment, the peptide release method yielded $19\times10^6$ cells, while the chymopapain release method yielded $22\times10^6$ cells. The positively selected CD34+ cells from the first experiment were grown in culture with cytokines for 12 days. The peptide-released cells showed a 100-fold expansion in cell number, while the chymopapain-released cells showed a 68-fold expansion. These results indicated that the peptide-release method could yield results comparable to the chymopapain-release method, and that the positively selected cells retained their potential to proliferate.

EXAMPLE 6

Analysis of modified peptides as competitive reagents to anti-CD34 monoclonal antibody binding to KG1a cells.

Additional experiments performed as detailed in Example 4 demonstrate that certain properties of the peptide sequences selected by phage display may be important in their ability to bind to the anti-CD34 antibody and to effectively displace the antibody prebound to the CD34 antigen expressed on the cell surface of KG1a cells.

Comparison of the selected peptide sequences to the published DNA sequence of the human CD34 antigen (Simmons, D. L., et al., *J Immunol* 148:267–271, 1992; He, X-Y., et al., *Blood* 79:2296–2302, 1992) revealed two potential epitope locations for hexamer type I and II. The shared TQG amino acid sequence was found at two locations in the translated CD34 sequence. Hexamer peptide sequences with either phage display flanking sequences or natural flanking sequences were tested for their ability to competitively bind and therefore release prebound anti-CD34 antibody, 9069, from KG1a cells.

Table 11 summarizes the peptide hexamer motifs examined, the exact peptide sequences tested, a brief description of their relevant features and their beta-turn potential (Previlige, P., Jr., and Fasman, G. D. Chou-Fasman Prediction of Secondary Structure of Proteins: The Chou-Fasman-Previlige Algorithm in *Prediction of Protein Structure and the Prinicples of Protein Conformation,* 1989, ed. G. D. Fasman, Plenum Press, New York).

TABLE 11

Modified Peptides as Competitive Binding Reagents to Anti-CD34 mAb 9069

| Hexamer Type | Peptide Name | Peptide Tested | Peptide Features* | Pt × 10a-4** | Competition % |
|---|---|---|---|---|---|
| none | | | | | 0 |
| | | (SEQ ID NO:21) | CD34 aa# 14–19 with: | | |
| VI | 9069E' | ADGA—TQGTFS—GAKD | 1. phage display flank | 1.2 | 91 |
| VI | 9069L | PELP—TQGTFS—NVSKE | 2. natural flank | 1.2 | 91 |
| | | (SEQ ID NO:22) | CD34 aa# 155–160 with | | |
| | | (SEQ ID NO:23) | | | |
| VII | 9069K | ADGA—TQGICL—GAKD | 1. phage display flank | 0.9 | 76 |
| VII | 9069M | EVKL—TQGICL—EQNKT | 2. natural flank | 0.9 | 77 |
| | | (SEQ ID NO:24) | | | |
| | | (SEQ ID NO:135) | | | |
| VIII (I/II) | 9069G' | ADGA—EQGFFP—GAKD | weak loop; xQGxFx | 0.68 | 4 |
| IX (I/II) | 9069H' | ADGA—NQGYFP—GAKD | strong loop; xQGxFx | 3.75 | 75 |
| | | (SEQ ID NO:25) | | | |
| | | (SEQ ID NO:9) | | | |
| I | 9069N | Ac—QQGWFP—KD | shortest type I | 2.3 | 97 |
| II | 90690 | Ac—TQGSFW—KD | shortest tpe II | 1.7 | 51 |
| | | (SEQ ID NO:8) | | | |

*additional charged residues for solubility are also shown.
**Maximal beta-turn potential calculated for tetrapeptides within the hexamer region.

Interestingly, biopanning of the phage display library could have identified hexamer sequences exactly matching the natural sequence. However, as a peptide may not maintain the folded structure as the same amino acid sequence found in a protein, the beta-turn potential or the ability to assume a loop-like structure is greater for the phage display selected peptides than the natural CD34 hexamer sequences. To determine if beta turn potential was an important feature of the competitive peptides, hexamer types VIII and IX were designed. Based upon comparison to the natural CD34 sequence TQGTFS (SEQ ID NO:136) and to the conservation of QG_F in two of the phage display selected hexamers, two new peptides maintaining the QG_F residues but either decreasing or increasing the beta-turn potential were tested.

Also, "minimal" octamer peptides lacking the phage display flanking sequences and only adding charged residues for solubility were tested.

Results: Peptides containing hexamer sequences derived from the actual CD34 sequence effectively competed off prebound anti-CD34 antibody from KG1a cells. Regardless of the type of flanking sequences (natural CD34 or phage display) the hexamer sequence representing motif VI was more efficient as a competitive reagent. This sequence also most closely matches the phage display selected hexamer sequences represented by motifs I and II.

Peptides representing hexamer motifs VIII and IX (see Table 11) were analyzed. Only the peptide with a hexamer sequence predicted to have good beta turn potential was capable of competing with prebound anti-CD34 antibody. This data supports the idea that a loop structure may be important in the recognition of CD34 by the 9069 antibody.

Comparison of short versions of hexamer motifs I and II lacking the phage display flanking sequences (with an acetylated amino end and KD added for solubility), indicated that the phage display sequences are not required for recognition of the hexamer by the antibody. In addition, hexamer motif I appears to be a better competitor than hexamer motif II.

EXAMPLE 7

Identification of a two-peptide motif representing a discontinuous epitope of CD34.

Analysis of the published CD34 cDNA sequence (Simmons, supra; He, supra) revealed the identification of two discontiunous regions homologous to the phage display selected hexamer sequences. The first region at amino acids 14–19 of the mature, signal peptide processed CD34 protein (epitope 1) is homologous to hexamer motif type I and II. The second region at amino acid 76–81 (epitope 2) is homologous to hexamer motif type IV and to the inverse of hexamer motif type III (see Table 12).

TABLE 12

Comparison of Phage Display Hexamer Motifs to Homologous CD34 Antigen Sequences

| Hexamer Motif | Phage Display Hexamer Motifs | Homologous CD34 Sequences | CD34 aa # |
|---|---|---|---|
| | (SEQ ID NO:7) | (SEQ ID NO:136 | |
| I | Q Q G W F P | T Q G T F S | 14–19 |
| | (SEQ ID NO:8) | (SEQ ID NO:136 | |
| II | T Q G S F W | T Q G T F S | 14–19 |
| | (SEQ ID NO:16) | (SEQ ID NO:14) | |
| III | L I S Q V S | N S S V Q S | 81–78 |
| | (SEQ ID NO:18) | (SEQ ID NO:14) | |
| IV | N S S V G L | N S S V Q S | 76–81 |
| | (SEQ ID NO:19) | (SEQ ID NO:136) | |
| V | T G Q A S T | T Q G T F S | 17–15 |

Since the atomic distances separating the side chains of amino acids SVQS is the same for SQVS, this selected peptide sequence was able to bind to the antibody. Of the five different hexamer sequences selected from the phage display library, only hexamer motif type V was weakly associated with either of the two identified epitope regions of CD34. Interestingly, the TGQ sequence of hexamer motif V is an inverse of amino acids 15–17 of epitope 1.

Peptides representing both epitope 1 and 2 could potentially have a synergistic effect in detaching and releasing CD34+ cells from antibody 9069.

EXAMPLE 8

Tryptophan to Phenylalanine Substitution in the 9069N Stem Cell Release Peptide Results in a Functional Release Peptide Phage display analysis identified a dominant hexapeptide sequence recognized by the anti-CD34 monoclonal antibody, 9069. The shortest peptide tested for competitive activity against 9069 antibody bound to KG1a cells had the following sequence: Ac-QQGWFP-KD (SEQ ID NO:9). Tryptophan is known to be unstable and therefore a modified peptide, 9069Q2, was designed in which the trytophan was replaced by a phenylalanine: Ac-QQGFFP-KD (SEQ ID NO:137). This latter sequence was shown to function as a competitive release reagent in the KG1a cell-based FACS assay.

Linear hexapeptide sequences that bind to the anti-CD34 monoclonal antibody, 9069, were identified through screening of a phage display library. The two most common hexapeptide sequences were homologous to a hexapeptide sequence at amino acids 14–19 in the mature CD34 antigen. Octapeptides containing the hexapeptide plus two charged residues to aid solubility were shown to function in a competitive cell-based FACS assay, to displace antibody from CD34+ cells. These peptides were shown to displace prebound 9069 antibody from KG1a cells. Subsequent testing of the 9069N peptide in Isolex® 50 experiments indicated the peptide functioned well for specific stem cell release.

The utilization of a peptide sequence containing a tryptophan residue poses specific degradation and stability issues in formulation. Since the homologous sequence in CD34 antigen did not contain a tryptophan, a variant peptide was designed in which the tryptophan was replaced with a phenylalanine residue. This latter residue would be much more stable to UV light exposure. If the modified peptide could function as a stem cell release agent then further product development studies on the alternate more stable peptide could be initiated.

This study documents the design and functional testing of the variant 9069 peptide, 9069Q2, in the cell-based KG1a FACS assay. The 9069Q2 peptide serves to displace prebound KG1a cells from the 9069 antibody.

Analysis of the variant peptide, 9069Q2, was done in parallel with the 9069N peptide. This analysis provides quality control information on reagents including the antibody, 9069, and the cells, KG1a. FACScan assays included a negative control of KG1a cells alone and positive control samples of KG1a cells with the 9069 antibody bound and detected with a secondary antibody, goat-anti-mouse IgG-FITC.

As previously shown, the 9069N peptide was able to displace prebound 9069 antibody from KG1a cells.

The 9069Q2 peptide was able to displace prebound 9069 antibody from KG1a cells.

The 9069N peptide defined through phage display contains a potentially unstable tryptophan residue. Replacement of this amino acid with phenylalanine did not abolish the ability of the peptide 9069Q2 to effectively compete off 9069 antibody bound to KG1a cells. Previous analyses of the hexapeptides revealed the likely requirement for good beta turn potential. (Prevelige, P. Jr., and Fasman, G. D. Chous-Fasman Prediction of Secondary Structure of Proteins: The Chou-Fasman-Prevelige Algorithm in Prediction of Protein Structure and the Principles of Protein Conformation, 1989, ed. G. D. Fasman, Plenum Press, New York.) Amino acid substitutions resulting in "poor" or "strong" beta-turn potential indicated that functional activity corresponded to the peptide with the most loop potential.

Additional modified peptide sequences maintaining the motif XQGXFX (SEQ ID NO:2) and including amino acid residues previously shown to be present in peptides with release activity were designed (Table 13 below). These candidate peptides could be made for future testing and comparison to the 9069N and 9069Q2 peptides.

TABLE 13

Comparison of 9069 Hexapeptides Defined by Phage Display With the CD34 Antigen and Substituted Variant Peptides

| Hexapeptide | Peptide Derivation | Beta-Turn potential* | Tested Peptide | Release Activity |
|---|---|---|---|---|
| (SEQ ID NO:138) T Q G T F S | CD34 antigen | 1.26 | 9069E' | yes |
| (SEQ ID NO:7) Q Q G W F P | phage display | 2.3 | 9069N | yes |
| (SEQ ID NO:8) T Q G S F W | phage display | 1.7 | 9069O | yes |
| (SEQ ID NO:139) E Q G F F P | variant | 0.68 | 9069G' | no |
| (SEQ ID NO:140) N Q G Y F P | variant | 3.75 | 9069H' | yes |
| (SEQ ID NO:2) Q Q G F F P | variant | 0.9 | 9069Q2 | yes |
| (SEQ ID NO:2) Q Q G T F P | variant | 1.09 | candidates for future testing | future testing |
| (SEQ ID NO:2) Q Q G S F P | | 1.46 | | |
| (SEQ ID NO:2) Q Q G Y F P | | 1.72 | | |
| (SEQ ID NO:2) Q Q G T F S | | 1.09 | | |
| (SEQ ID NO:2) Q Q G Y F S | | 1.72 | | |
| (SEQ ID NO:2) T Q G T F P | | 1.26 | | |
| (SEQ ID NO:2) T Q G S F P | | 1.7 | | |

*Beta turn potential X 10e-4; maximum beta-turn potential calculated for tetrapeptides within the hexamer region.

Tested peptides contain additional flanking sequences either derived from the phage display vector and/or charged residues to aid solubility.

EXAMPLE 9

9079 Antibody Selection of Hexapeptide Sequences Through Phage Display Technology The 9079 anti-CD34 antibody was used to select linear hexapeptide sequences from a phage display library. Multiple unrelated hexapeptide sequences with no direct homology to the CD34 antigen were identified from third and fourth biopanning phage clones. A fifth biopanning revealed a predominant hexapeptide sequence.

The current human stem cell isolation system developed by the Immunotherapy Division utilizes the anti-CD34 antibody, 9069. Replacement of the chymopapain treatment to release captured stem cells is desirable. Potential problems of immunogenicity of residual amounts of remaining chymopapain, lot variation with chymopapain and the inability to perform additional negative selections due to stripping of cell surface antigens with the chymopapain treatment were among the reasons for investigating alternative release reagents.

The original protocols for phage display biopanning of the linear hexapeptide library obtained from Dr. George Smith at the University of Missouri designated the use of biotinylated antibody. Three biopanning steps with the 9079 antibody were performed. The third eluate was stored at 4° C. for one year, then subjected to amplification prior to the fourth biopanning. A fifth biopanning was performed from an unamplified fourth biopanning. Phage clones fom the third, fourth and fifth biopannings were subjected to DNA sequence analysis. Multiple hexapeptide sequences were identified in each biopanning. Only in the fifth biopanning did a predominant sequence emerge. None of the selected hexapeptides show direct homology to the CD34 antigen.

Eight hexapeptide sequences were chosen for synthesis. A KG1a cell-based FACS assay was used to examine their ability to displace prebound 9079 antibody.

Materials:

The linear hexapeptide library was obtained from Dr. George Smith at the University of Missouri. The random hexapeptide sequence was inserted into the pIII gene of the vector FUSES. The 9079 antibody was obtained from Ginny Ofstein in the Bone Marrow Therapies R & D Group, Immunotherapy Division, Santa Ana.

Other materials:

NHS-LC-Biotin, Pierce # 21335.

Streptavidin, Gibco #5532.

K91kan cells, obtained from Dr. George Smith, University of Missouri.

Terrific broth™, Gibco BRL # 152-02711M.

NZY broth™, Gibco #M36350B.

Tetracycline hydrochloride, Sigma # T-3383.

Polyethylene glycol 8000, Sigma P-2139.

Sodium chloride, Mallinckrodt # 7581.

Kanamycin monosulfate, Sigma #K-1377.

JTL2 oligonucleotide primer, purchased from Operon, Technologies, Inc.

JTL2: 5' GCC CTC ATA GTT AGC GTA ACG ATC 3'

This primer allows DNA sequence determination of the anti-sense strand of the FUSE5/X6 library clones. ABI Prism Cycle Sequencing Kit, ABI # 401434.

Methods

The hexapeptide library was amplified in 2 L of Terrific broth™ (500ml per 2L flask) as described above. Briefly, K91kan cells were grown to an OD550~2.0 at 225 rpm, 37° C. After 15 minutes at 50 rpm for pili regeneration, the cells were infected with the library at a moi~1 (multiplicity of infection of 1 phage particle per cell). Infection was allowed to proceed overnight.

The amplified library was concentrated with PEG/NaCl from ~2L to 1 ml.

The 9079 antibody was biotinylated following the procedure of G. Smith.

Three steps of petri plate (35 mm) biopanning were performed following the procedures of George Smith. The amount of biotinylated 9079 antibody used per step was: 10 ug-1st biopanning, 10 ug-2nd biopanning, lug-3rd biopanning ("10-10-1"). Each successive step of biopanning was preceded by an amplification of the eluted phage. 5×1010 TU of the library were used in the first biopanning.

Tetracycline/kanamycin resistant colonies from the third biopanning were grown and supernatants containing the bacteriophage were PEG precipitated.

DNA was prepared from the PEG concentrated phage for DNA sequence analysis. DNA sequence was determined following "cycle" sequencing reactions using the Applied Biosystems PRISM fluorescent dideoxy terminators and oligonucleotide primer JTL2.

A fourth biopanning was performed after amplication of the third eluate. Three different concentrations of non-biotinylated 9079 antibody were used: 0.02 ug, 0.1 ug and 1 ug.

Eluted clones were grown and DNA prepared as above.

DNA sequence analysis was performed using JTL2 primer as above.

A fifth biopanning using 1 ug of non-biotinylated 9079 antibody was performed with the 4th biopanning eluate in the absence of amplification.

DNA sequence analysis was performed using JTL2 primer on 14 clones from the fifth biopanning.

The above steps were repeated.

Results

A total of five steps of biopanning were performed with the 9079 antibody and the hexapeptide library. DNA sequence analysis of the third and fourth biopannings revealed many different hexapeptide sequences with no apparent homology to the CD34 antigen. The 0.02 ug and 0.1 ug 9079 antibody 4th biopannings revealed many uninserted clones. The fifth biopanning was performed with the eluate at 1 ug of 9079 antibody during the fourth biopanning. Only 14 clones were subjected to DNA sequence analysis and none contained uninserted vector.

A predominant hexapeptide sequence emerged from the fifth biopanning. Eight peptide sequences representing 3rd, 4th and 5th biopanning clones were selected for functional analysis as potential stem cell release reagents.

Phage display analysis of the 9079 antibody with a linear hexapeptide library revealed multiple hexapeptide sequences with no apparent direct homology to the CD34 antigen. This result is similar to the results observed with the 561 antibody when biopanned on petri plates (see below). The 9079 antibody is capable of blocking recognition of the CD34 antigen by the 561 antibody (Dynal). The possibility exisits that both the 561 and 9079 antibodies recognize the region of CD34 containing six cysteine residues and the only arginine residues (amino acids 146–219). Recognition of flexible loops stabilized by charged amino acids may result in the selection of many different hexapeptide sequences. The identification of uninserted clones in the analysis of fourth biopanning clones may be a result of the one year long storage of the unamplified 3rd eluate. Uninserted clones are know to grow more efficiently than the hexapeptide-containing clones and may also have better viability during long-term storage. At very low 9079 antibody concentrations (0.02 ug and 0.1 ug) during the 4th biopanning, many non-specific, uninserted clones were eluted. At higher antibody concentration (1 ug) very few uninserted clones were identified. The fifth biopanning was performed in the absence of amplification of the fourth (1 ug) biopanning to avoid enhancement of selecting uninserted clones. Of the fourteen clones analyzed from the 5th biopanning, no uninserted clones were identified.

Both the use of biotinylated and non-biotinylated antibody can be used for phage display biopanning. The biotinylated 9079 was used for the first three biopanning steps. Based on the successful results of biopanning with non-biotinylated 9069 antibody, the subsequent biopannings with the 9079 antibody were accomplished with non-biotinylated antibody.

Epitope peptide phage display biopanning with the 9079 antibody revealed multiple hexapeptide sequences until a fifth biopanning step was performed. Whether these sequences actually represent all or portions of discontinuous epitopes of the CD34 antigen is not known. The identification of multiple sequences suggest that mimetopes that mimic the actual epitope sequence may have been selected.

Eight peptides representing hexapeptides selected from the third (1) , fourth (6) and fifth (1) biopannings were synthesized and tested for their ability to serve as release reagents in the KG1a cell-based FACS assay.

TABLE 14

Biopanning Steps With 9079 Antibody.

| BIOPANNING STEP | SCHEME* | ANTIBODY USED |
|---|---|---|
| 1st | 10 | Biotinylated 9079 |
| 2nd | 10-10 | biotinylated 9079 |
| 3rd | 10-10-1 | biotinylated 9079 |
| 4th | 10-10-1-0.02 | 9079 |
| 4th | 10-10-1-0.1 | 9079 |
| 4th | 10-10-1-1 | 9079 |
| 5th | 10-10-1-1-1 | 9079 |

*Amount of antibody (ug) used per biopanning step. Each successive biopanning is performed with the eluated phage from the prior biopanning. The fourth biopanning was performed at three different concentrations of antibody.

TABLE 15

Third Biopanning Hexapeptide Sequences Identified by Phage Display with the 9079 Antibody

| | | | |
|---|---|---|---|
| R I G A F R | (SEQ ID NO:141) | | |
| S F R V G Y | (SEQ ID NO:142) | D G L P A R | (SEQ ID NO:143) |
| W S S N R F | (SEQ ID NO:144) | | |
| R E R T S S | (SEQ ID NO:145) | S W R H V Q | (SEQ ID NO:146) |
| G L P R S W | (SEQ ID NO:147) | N Q R W L L | (SEQ ID NO:148) |
| I F Q R N M | (SEQ ID NO:149) | R M D G T F | (SEQ ID NO:150) |
| L P Y L M R | (SEQ ID NO:151) | M N Y V S L | (SEQ ID NO:152) |
| T M T F H G | (SEQ ID NO:153) | M T Y S S G | (SEQ ID NO:154) |
| H T P M V T | (SEQ ID NO:155) | G H H A T G | (SEQ ID NO:156) |
| H D G L Y I | (SEQ ID NO:157) | Q H P F T V | (SEQ ID NO:158) |
| Q V G E Q H | (SEQ ID NO:159) | | |
| Q T S L L H | (SEQ ID NO:160) | S L L Y V D | (SEQ ID NO:161) |
| L G G W L A | (SEQ ID NO:162) | P V F L G V | (SEQ ID NO:163) |
| W N L S D K | (SEQ ID NO:164) | | |

DNA sequence analysis (10 ug-10 ug-1 ug) of the third biopanning revealed at least 29 different sequences.

None of these sequences had direct homologies to the CD34 antigen sequence. A relatively high occurence of arginine was seen in about half of the clones.

The underlined sequence represented by three clones was selected for peptide synthesis and functional analysis.

TABLE 16

Fourth Biopanning Hexapeptide Sequences Identified by Phage Display with the 9079 Antibody.

| | | | | |
|---|---|---|---|---|
| 10-10-1-0.02ug: | Most clones analyzed were uninserted (20/23). Two hexapeptide sequences were identified | | | |
| | I Q E F G V (1) | (SEQ ID NO:165) | T T D Q F S | (SEQ ID NO:166) |
| 10-10-1-0-0.1ug: | 30/40 clones were uninserted. Five preliminary sequences were identified. Additional sequence and repeat sequence of new templates was needed. | | | |
| | X S X V F R | (SEQ ID NO:167) | | |
| | R A A G L X | (SEQ ID NO:168) | | |
| | M L P X X G | (SEQ ID NO:169) | | |
| | R S F Y Y R (2) | (SEQ ID NO:170) | | |
| | Y V A X T H | (SEQ ID NO:171) | | |
| 10-10-1-1ug: | 6/40 clones are confirmed to have no insert. More than 20 sequences preliminarily | | | |
| identified. | | | | |
| | A Y E A Q A | (SEQ ID NO:172) | Q R F A S V | (SEQ ID NO:173) |
| | N L Q G E L | (SEQ ID NO:174) | S F N H P V | (SEQ ID NO:175) |
| | N L Q G E F (2) | (SEQ ID NO:176) | P G S P L G (2) | (SEQ ID NO:177) |
| | Y S R L G F (2) | (SEQ ID NO:178) | Q V L R E S (2) | (SEQ ID NO:179) |
| | S D L T L R | (SEQ ID NO:180) | M R Y P T R | (SEQ ID NO:181) |
| | H I G I S L | (SEQ ID NO:182) | R X S E F X | (SEQ ID NO:183) |
| | V V R S L Y | (SEQ ID NO:184) | G Y T Q P K | (SEQ ID NO:185) |
| | Y M W V T E | (SEQ ID NO:186) | G Y T Q P I | (SEQ ID NO:187) |

Underlined peptide sequences were ordered and tested. Number following peptide sequence indicates number of clones with identical or 5/6 match.

TABLE 17

Fifth Biopanning Hexapeptide Sequnces Identified by Phage Display with the 9079 Anitbody.

| Sequence | | Number of Clones |
|---|---|---|
| I R A R G N | (SEQ ID NO:188) | 1 |
| V Y S L W P | (SEQ ID NO:189) | 6 |

The 5th biopanning (10-10-1-1-1) indicates a predominant sequence has emerged. This biopanning was performed without amplification of the 4th eluate to avoid overgrowth during amplification of uninserted phage vector which was seen in the analysis of the 4th biopanning clones.

EXAMPLE 10

Analysis of Peptides as Release Reagents for the 9079 Antibody Using a Cell-Based FACS Assay Eight hexapeptides selected from the 3rd, 4th and 5th biopannings of the 9079 antibody were synthesized with additional charged residues as deemed necessary to ensure solubility.

These peptides were tested for functional activity as potential stem cell release reagents using the KG1a cell-based FACS assay. In preliminary experiments six peptides showed at least 50% release of 9079 antibody prebound to cells.

The 9079 antibody was chosen for further study because of it's high binding affinity, it's retention of functional activity upon chemical biotinylation, and the chymopapain-resistant nature of it's recognition of CD34 antigen. Phage display biopanning with the anti-CD34 antibody, 9079, identified multiple hexapeptide sequences (see above). A predominant sequence was identified in the fifth biopanning.

Eight hexapeptides representing clones isolated in the third, fourth and fifth biopannings were synthesized and tested in the KG1a cell-based FACS assay. Six of the peptides showed at least 50% release of 9079 antibody prebound to KG1a cells in a FACS assay.

The peptides (see Table 18) were synthesized by Research Genetics and tested without purification. The 9069 and 9079 antibodies were obtained from the Baxter Immunotherapy Research group in Santa Ana. The 9079 antibody has been deposited with the American Type Culture Collection (ATCC) under the provisions of the Budapest Treaty for patent purposes: deposit number ATCC-HB-11885, date of deposit May 9, 1995. The 9069 antibody was used as a positive control and released with the 9069N peptide (Ac-QQGWFP-KD) (SEQ ID NO:9). This control served to test for the KG1a cells and the goat-anti-mouse FITC secondary detection antibody. Hexapeptide sequences identified for the 561 antibody also were tested for their ability to displace prebound 9079 antibody.

Peptides (see Table 18) were purchased from Research Genetics Inc., Hunstville, Ala.

9079A-G peptides were solubilized in Dulbecco's phosphate buffered saline (DPBS) plus 1% HSA.

The 9079A-G peptides were tested in the FACScan assay using 10^6 KG1a cells bound with 0.05 ug of the 9079 antibody.

The 561A-E peptides (see Example 13 below) were tested in the FACScan assay using 10^6 KG1a cells bound with 0.05 ug of the 9079 antibody.

The 9079H peptide was tested in the FACScan assay using 10^6 KG1a cells bound with 0.05 ug of the 9079 antibody.

Results

Peptides 9079A, B, C, D, F, and H were solubilized. 9079E peptide was insoluble and therefore not tested.

The 9079A, B, C, D, F, G and H peptides all showed at least 50% release of prebound 9079.

None of the 561A-E peptides could release prebound 9079 antibody.

Functional analysis of potential peptide release reagents for the anti-CD34 antibody 9079 was performed in a KG1a cell-based FACS assay. These data indicate that only the peptides defined by phage display biopanning with the 9079 antibody can serve to displace cell-bound 9079. The 561 antibody is believed to share a common epitope region of the CD34 antigen with the 9079 antibody. However, the phage display defined peptides for the 561 antibody do not have any displacement activity on the 9079 antibody.

The lack of direct homology of the 9079 peptides to the CD34 antigen protein sequence suggest that these peptides may mimic the natural epitope. The presence of arginine residues in three of the peptides suggest a similarity to the peptides recognized by the 561 antibody. A localized region of the CD34 antigen (amino acids 150–219) contains the only five arginine residues. However, the other peptides contain hydrophobic residues suggesting the possibility that both charged and hydrophobic residues are important for peptides to bind tightly to the 9079 antibody.

TABLE 18

Peptides Tested for Release Activity with the 9079 Anti-CD34 Antibody.

| Peptide Tested | Sequence* |
|---|---|
| 561A | RHRHRH(SEQ ID NO:34) |
| 561B | KRHKHR(SEQ ID NO:35) |
| 561C | RTKTRF(SEQ ID NO:36) |
| 561D | TRVPRR(SEQ ID NO:37) |
| 561E | RHRPRH(SEQ ID NO:38) |
| 9079A | PGSPLG—KD(SEQ ID NO:26) |
| 9079B | YSRLGF—KD(SEQ ID NO:27) |
| 9079C | QYTQPK—D(SEQ ID NO:28) |
| 9079D | NLQGEF—KD(SEQ ID NO:29) |
| 9079E | RSFYYR—D(SEQ ID NO:30) |
| 9079F | IQEFGV—KD(SEQ ID NO:31) |
| 9079G | SFRVGY—KD(SEQ ID NO:32) |
| 9079H | KD—VYSLWP—KD(SEQ ID NO:33) |

*Hyphens separate hexapeptide sequences selected through phage display from the charged residues added to aid solubility.

Peptide 9079E was insoluble and therefore not tested.

Peptide 9079C was incorrectly assigned. However, it tested positively. The correct sequence should have been GYTQPK-D.

TABLE 19

Summary of Peptide Release Activity with the 9079 Antibody.

| Peptide Name | Sequence* | % Release** |
|---|---|---|
| none | | 100 |
| 9079A | PGSPLG-KD (SEQ ID NO: 26) | 74.1 |
| 9079B | YSRLGF-KD (SEQ ID NO: 27) | 55.0 |
| 9079C | QYTQPK-D (SEQ ID NO: 28) | 59.3 |
| 9079D | NLQGEF-KD (SEQ ID NO: 29) | 67.8 |
| 9079E | RSFYYR-D (SEQ ID NO: 30) | not tested |
| 9079F | IQEFGV-KD (SEQ ID NO: 31) | 68.9 |
| 9079G | SFRVGY-KD (SEQ ID NO: 32) | 35.3 |
| 9079H | KD-VYSLWP-KD (SEQ ID NO: 33) | 66.2 |

*Hyphens separate hexapeptide sequences selected through phage display from the charged residues added to aid solubility.
Peptide 9079E was insoluble and therefore not tested.
**% Release = 100 − % Binding $$\% \text{ Binding} = \frac{(\text{mean with peptide}) - (\text{mean cells only})}{(\text{mean without peptide}) - (\text{mean cells only})}$$

EXAMPLE 11

Analysis of Potential Antigenic Peak Peptides Derived from the CD34 Antigen as Release Reagents for the 561 and 9079 Antibodies Eleven potential antigenic regions of the CD34 antigen were determined using Macvector™ 4.1 software. Peptides representing six of these regions were designed and synthesized. The KG1a cell-based FACS assay was used to examine these peptides for their feasibility as release reagents for the 9079 and 561 anti-CD34 monoclonal antibodies. None of the tested peptides showed significant release activity with either the 9079 nor the 561 antibody.

The purpose of this study was to define potential stem cell release reagents for the 9079 and 561 antibodies through computer analysis of the published CD34 antigen protein sequence. In parallel to defining alternative release reagents through phage display technology, we chose to study the CD34 antigen for likely epitope regions. Extensive analysis of the structural requirements for a protein to elicit an immune response has been reported in the literature. The MacVector 4.1 software permits one to examine a protein sequence and define potential antigenic peaks. This analysis is designed to identify possible exposed surface peaks of the protein combining information from hydrophilicity, surface probability and backbone flexibility predictions with the secondary structure predictions of Chou-Fasman and Robson-Garnier (MacVector™User's Manual, International Biotechnologies, Inc., pages B56–B69; Jameson, B. A. et al., 1988 *Comput. Applic. in the Biosciences* 4:181–186).

Analysis of the extracellular domain of the CD34 protein revealed eleven potential antigenic peaks varying from four to eight amino acids in length. Previous comparison of the 9069 anti-CD34 monoclonal antibody-selected phage display epitope sequences with the CD34 antigen revealed overlap with two of the computer-defined potential antigenic peaks. Based on that knowledge and the conclusions drawn from the 9079 and 561 biopanning experiments (see above), six antigenic peaks were selected for further analysis.

The peptides (see Table 19) were synthesized by Research Genetics and tested without purification. The 9079 antibody was obtained from the Baxter Immunotherapy Research Group in Santa Ana, Calif. The 561 antibody was obtained from Dynal, AS.

Peptides (see Table 19) were purchased from Research Genetics, Inc., Huntsville, Ala.

Results

Eleven potential antigenic peaks were defined in the CD34 antigen sequence. Amino acid residues with positive (+) antigenic index values (ranging from +0.009 to +0.441) were considered significant.

Six peptides were designed, synthesized, and tested for activity as release reagents.

Peptides 34A–F did not show any release activity on 9079 antibody prebound to KG1a cells.

Peptides 34A–F did not show any release activity on 561 antibody prebound to KG1a cells.

The identification of multiple hexapeptide sequences upon four plate biopanning steps with the 9079 and 561 antibodies prevented easy selection of which peptides to synthesize for functional testing. The recognition of a correspondence of the 9069 phage display-selected hexapeptides with computer-defined potential antigenic peaks, suggested the possibility that similar analysis with the 9079 and 561 antibodies might aid in the selection of a few hexapeptides to test. In addition to defining true epitope peptides, this analysis would help select which phage display hexapeptides might be more likely to exhibit release activity based on homology to the CD34 antigen.

Functional analysis of peptides representing potential antigenic peaks of the CD34 antigen as release reagents for the 9079 and 561 antibodies was performed in the KG1a cell-based FACS assay. To limit the cost of contracting peptide synthesis, only six antigenic peaks were chosen for analysis. They were selected because of their length (longer than four amino acids), not corrresponding to the 9069 epitope regions, similarity to the selected phage display sequences (for both 9079 and 561) , and/or their location within the arginine-rich and cysteine-rich region of the CD34 antigen.

Functional testing of linear potential antigenic peak peptides defined from the published CD34 antigen sequence did not result in the identification of new peptide release reagents for the 9079 or 561 antibodies. The inability of linear peptides to mimic the structure of the actual epitope may be critical for recognition by these antibodies. The conclusions drawn from the biopanning experiments of the hexapeptide and a cyclic peptide library with the 561 antibody strongly suggest that an epitope of specific non-linear conformation is being recognized. A consensus sequence was identified for the 561 antibody from the cyclic peptide library. This sequence shows homology to one of the potential antigenic peak peptides (34D). Whether or not this peptide sequence reflects a discontinuous epitope is unknown.

In addition, biopanning of the hexapeptide library with the 561 antibody directly attached to magnetic beads identified one (P A N V S L) (SEQ ID NO:94) of three hexapeptides which show good homology (5/6 amino acids, P A N V S T (SEQ ID NO: 190) in CD34) to a defined potential antigenic peak (N V S T) (SEQ ID NO:191) of the CD34 antigen. Since this sequence had only four amino acids, this was not among those peaks for which a peptide was designed and tested. It is believed, however, that a peptide containing this 4-amino-acid sequence is a good candidate for a releasing agent for the 561 antibody.

The accumulated data from the analyses of the 9069, 9079 and 561 anti-CD34 antibodies indicate that determination of the potential antigenic peaks of an antigen protein may save time in defining potential competitive epitope peptides. Correlation of the defined peaks with any known structural data on the antigen and correspondence to phage display-defined peptides will permit the best educated guess on selection of peptide sequences to test for functional activity. If a particular antibody of interest can recognize a linear peptide epitope such as that of the 9069 antibody, then this type of analysis could supersede the initiation of the laborious phage display work. However, if the antibody recognizes a conformational or discontinuous epitope, then this type of analysis can at best support but not define a peptide with functional release activity. Analysis of possible antigenic determinants:

Arginine and cystein residues were identified.

P A N V S T (SEQ ID NO:190) was the CD34 antigen hexapeptide sequence homologous to the P A N V S L (SEQ ID NO:94) hexapeptide identified by biopanning with direct 561 antibody attached to beads.

T Q G T F S (SEQ ID NO:192) was the CD34 antigen hexapeptide homologous to T Q G S F W (SEQ ID NO:8) and Q Q G W F P (SEQ ID NO:7) hexapeptides identified by biopanning with the 9069 antibody.

N S S V Q S (SEQ ID NO:14) was the CD34 antigen hexapeptide homologus to N S S V G L (SEQ ID NO:18) hexapeptide identified by biopanning with the 9069 antibody.

TABLE 20

Peptides Representing Six Potential Antigenic Peaks of the CD34 Antigen.

| ANTIGENIC PEAK | LOCATION* | PEPTIDE | PEPTIDE SEQUENCE** | HOMOLOGY TO PHAGE DISPLAY PEPTIDES |
|---|---|---|---|---|
| (SEQ ID NO:192) NNGTA | aa 4–8 | | | |
| (SEQ ID NO:193) LPTQGT | aa 12–17 | | | 9069, TQGSFW(SEQ ID NO:8) QQGWFP(SEQ ID NO:7) |
| (SEQ ID NO:194 QHGNEAT | aa 46–52 | | | |
| (SEQ ID NO:195) GNTNS | aa 83–87 | | | 9069, NSSVGL(SEQ ID NO:18) |
| (SEQ ID NO:196) NVST | aa 95–98 | | | 561, PANVSL(SEQ ID NO:94) |
| (SEQ ID NO:197) LSPG | aa 107–110 | 34A | (SEQ ID NO:198) KPSLSPG—KD | |
| (SEQ ID NO:199) TKPYTSSS | aa 127–134 | 34B | (SEQ ID NO:200) D—TKPYTSSS—KD | |
| (SEQ ID NO:201) QNKTSS | aa 162–167 | 34C | (SEQ ID NO:202) LEQNKTSS—KD | |

TABLE 20-continued

Peptides Representing Six Potential Antigenic Peaks of the CD34 Antigen.

| ANTIGENIC PEAK | LOCATION* | PEPTIDE | PEPTIDE SEQUENCE** | HOMOLOGY TO PHAGE DISPLAY PEPTIDES |
|---|---|---|---|---|
| (SEQ ID NO:203) | | | (SEQ ID NO:204) | |
| FKKDRG | aa 171–176 | 34D | EFKKDRGEGLAR | 561, CIDEFLRCI(SEQ ID NO:205) |
| (SEQ ID NO:206) | | | (SEQ ID NO:207) | |
| SEVR | aa 105–108 | 34E | D—LAQSEVRPQ—KD | |
| (SEQ ID NO:208) | | | (SEQ ID NO:209) | |
| QSYSQK | aa 253–258 | 34F | KD—HQSYSQKT | |

*Amino acid position in the extracellular domain of the CD34 protein.
**Amino acid residues (K, D) separated by a hyphen (-) were added to aid solubility.

EXAMPLE 12

561 Antibody Selection of Hexapeptide Sequences through Phage Display Technology Four predominant peptide sequences were identified with a major characteristic being their basic nature, each containing at least two arginine residues. No direct homology to the CD34 antigen protein was observed in the predominate sequences. However, there was homology to a region of the CD34 antigen (aa # 149–219) which contains the only 5 arginine residues in the entire CD34 antigen. These data suggest that the 561 antibody recognizes a specific conformational epitope within the CD34 antigen.

The linear hexapeptide library and K91Kan cells were obtained from Dr. George Smith at the University of Missouri. The random hexapeptide sequence was inserted into the pIII gene of the vector FUSE5. The 561 antibody 4.7 mg/ml was obtained from Dynal A.S. Oslo, Norway.

Biopanning procedures were as described in Example 1 above. Other materials were obtained as follows:

Urea, IBI
10× TBE buffer, BRL
Amberlite, Sigma, St. Louis, Mo.
Acrylamide/Bis, BioRad, Richmond, Calif.
TEMED, IBI,
Ammonium persulfate, IBI,
Sodium Bicarbonate (NaHCO3), Sigma,
Dialyzed BSA, Sigma,
Sodium Azide (NaN3), Sigma,
Ethylenediamine Tetraacetic Acid (Na2EDTA), Sigma,
Sodium Hydroxide (NaOH), RICCA Chemical Company,
Hydrochloric Acid (HCl), Mallinckrodt,
Formamide, USB
Kanamycm, Sigma,
Potassium Chloride (KCl), Mallinckrodt,
Sodium Chloride (NaCl), Sigma,
Sodium Acetate (NaOAc), Sigma,
Glacial Acetic Acid, Sigma,
Ammonium Phosphate, Mallinckrodt
Ammonium Hydroxide (NH40H), Sigma,
NZY, GIBCO,
PEG 8000, Sigma,
Bacto Agar, DIFCO, Cat.#0140-01
Prism Ready Reaction Dye Deoxy Terminator Cycle Sequencing Kit, Perkin ELMER,
CENTRI SEP Spin Columns, Princeton Separations, Oligonucleotide Primers—Synthesized by Operon, Inc.

```
JTL1:   5' CAATTAAAGGCTCCTTTTGGAGCC 3'   (SEQ ID NO: 210)

JTL2:   5' GCCCTCATAGTTAGCGTAACGATC 3'   (SEQ ID NO: 211)
```

Primers were identical to the published bacteriophage fl sequence (Hill, D. F., et al., *J. Viroloy* 44:32–46, 1982) at positions 1533–1556 and the complement of positions 1714–1737.

Gene Amp PCR system 9600, Perkin ELMER Cetus, Metrology 8451A DIODE Array Spectrophotometer, Hewlett Packard 373A DNA Sequencer—Applied Biosystems MacVector™ 4.1 DNA Sequence Analysis Software International Biotechnologies, Inc.

Methods:

The hexapeptide library was amplified in 2 L of terrific broth (500 ml per 2 L flask). Briefly, K91Kan cells were grown to an OD550 ~2.0 at 225 rpm, 37° C. After 15 minutes at 50 rpm for pili regeneration, the cells were infected with 10 μl (~$10^{12}$ physical particles) of the primary library. The amplified library was concentrated with PEG/NaCl from ~2 L to 1 ml. The amplified library was titered. Seven rounds of biopanning were performed as described in Example 1 above. The amount of 561 antibody used per step was: 28 μg-1st biopanning, 14 μg-2nd biopanning, 5 or 10 μg-3rd biopanning, 1 μg-4th biopanning, 1 μg-5th biopanning, 2 μg-6th biopanning, 1.5 μg-7th biopanning ("28-14-10-1-1-2-1.5 or 28-14-5-1-1-2-1.5". Each successive step of biopanning was preceded by an amplification of the eluted phage. $5\times10^{10}$ TU of the library were used in the first biopanning. Tetracycline/Kanamycin resistant colonies from the third to seventh rounds of biopanning were grown and supernatants containing the bacteriophage were PEG precipitated. DNA was prepared from the PEG concentrated phage for DNA sequence analysis. DNA sequence was determined following "cycle" sequencing analysis using the Applied Biosystems PRISM fluorescent dideoxy terminators and oligonucleotide primer JTL2.

Results:

Amplification of the cyclic peptide library resulted in a final titer of $2.5\times10^{13}$ TU/ml (TU=transducing units), ~1 ml, stored at 40C.

Results from seven rounds of biopanning are shown in Table 21.

DNA sequence analysis was determined for 220 bacterial clones selected from the third, fouth, fifth, sixth, and seventh rounds of biopanning.

DNA sequence analysis of the third and fourth rounds of biopanning revealed one predominant sequence (Table 21).

Three more predominant hexapeptide sequences emerged from the sixth, and seventh rounds of biopanning (Table 22).

A major characteristic of these hexapeptide sequences is their basic nature, each containing at least two arginine residues. No direct homology of the predominant peptide sequence with the CD34 antigen was identified.

The only five arginine residues in the CD34 antigen are present in the extracellular domain, amino acids 149 to 219.

Five peptide sequences (A to E) representing 3rd, 4th, 5th, 6th and 7th biopanning clones were selected for functional analysis as potential stem cell release reagents.

Phage display analysis of the 561 antibody with a linear hexapeptide library revealed 4 predominant hexapeptide sequences with no apparent direct homology to the CD34 antigen. This result is similar to the results observed with the 9079 antibody when biopanned on petri plates. The 561 antibody is capable of blocking recognition of the CD34 antigen by the 9079 antibody. It is possible that both the 561 and 9079 antibodies recognize the region of CD34 containing six cysteine residues and the only five arginine residues. Recognition of flexible loops stabilized by charged amino acids may result in the selection of hexapeptide sequences recognized by a discontinuous epitope.

Biopanning of a hexapeptide library with the 561 antibody resulted in the identification of four predominant sequences (561 peptide A to D). These hexapeptide sequences contain both highly charged and hydrophobic residues which is also supported by the conclusions drawn from the cyclic peptide biopanning analysis (see Example 12) and linear hexapeptide selection using 561-Dynabead (see Example 13). The repeated selection of peptides containing arginine residues may be indicative of specific recognition of the region within the CD34 antigen (a.a.#149 to 219) containing the only five arginine residues in the extracellular domain of the protein.

Five peptides representing hexapeptides selected from biopannings were synthesized and tested for their ability to serve as release agents in the KG1a or tHL60 cell-based FACS assay. Two of these peptides (561 C and 561 D) are able to release 561 antibody prebound to KG1a cells.

TABLE 21

Summary: 561 Peptide Selection Scheme
Phage Display Biopanning with 561 Antibody

| Selection | Biopanning Rounds micrograms Ab | | | | | | | No. of Clones | No. of Clones |
|---|---|---|---|---|---|---|---|---|---|
| Scheme | 1st | 2nd | 3rd | 4th | 5th | 6th | 7th | Purified | Analyzed |
| A | 28 | 14 | 5 | | | | | 40 | 20 |
| A | 28 | 14 | 5 | 1 | | | | 80 | 20 |
| A | 28 | 14 | 5 | 1 | 1 | | | 40 | 10 |
| A | 28 | 14 | 5 | 1 | 1 | 2 | | 40 | 10 |
| A | 28 | 14 | 5 | 1 | 1 | 2 | 1.5 | 80 | 40 |
| B | 28 | 14 | 10 | | | | | 40 | 20 |
| B | 28 | 14 | 10 | 1 | | | | 80 | 20 |
| B | 28 | 14 | 10 | 1 | 1 | | | 40 | 10 |
| B | 28 | 14 | 10 | 1 | 1 | 2 | | 40 | 10 |
| B | 28 | 14 | 10 | 1 | 1 | 2 | 1.5 | 80 | 60 |

TABLE 22

Hexapeptide Sequences Identified by Phage Display with 561 Antibody

| | Rounds of Biopanning* | | | | | | | | | |
|---|---|---|---|---|---|---|---|---|---|---|
| | 7th | | 6th | | 5th | | 4th | | 3rd | |
| | micrograms of Ab in 3rd biopanning | | | | | | | | | |
| Hexamer Sequences | 5 | 10 | 5 | 10 | 5 | 10 | 5 | 10 | 5 | 10 |
| RHRHRH (561A) | 22 | 46 | 3 | | 3 | | | | | |
| KRHKRH (561B) | 14 | 2 | 1 | 3 | | 2 | 1 | 3 | | |
| RTKTRF (561C) | | 8 | | 5 | 4 | 4 | 1 | 1 | | 1 |
| TRVPRR (561D) | | | | | | 3 | 4 | 4 | | 6 |
| RHRPRH (561E) | | | 1 | | | | | | | |

*Number of clones identified at each indicated biopanning step.

EXAMPLE 13

561 Antibody Selection of Hexapeptide Sequences through Phage Display Technology Using 561-Direct Magnetic Beads.

Four predominant peptide sequences were identified with major characteristics being their highly charged and hydrophobic nature. These data suggest that the structure of the CD34 epitope recognized by 561 is likely to include a loop, possibly containing hydrophobic residues, stabilized by ionic interactions mediated through charged amino acids. One of the predominant hexapeptides PANVSL (SEQ ID NO:94) (561Q) has direct homology to the CD34 antigen (PANVST)(SEQ ID NO:190).

Phage-bearing peptides with high affinity for 561 antibody were selected from those with low affinity peptides using 561 antibodies immobilized on solid-phase petri dishes as described in Example 1 above. However, fine affinity discriminations were difficult, possibly because binding was dictated by both the affinity and the avidity of the phage (Clarkson, T., et al., 1991, *Nature* 352:624–628). An alternative selection method was based on phage peptides binding to 561 directly linked to Dynabeads (561-bead) in solution. The high affinity phage peptides were then enriched by competition for limiting amounts of antibody. It is believed that this scheme forced the many low affinity phage to be out-competed by the binding of rare high affinity variants.

Peptide epitopes in solution were selected using the hexapeptide library with two different lots of 561-beads CEL R21 and CEL R73. Four predominant linear hexapeptide sequences were selected and identified with a major characteristic being their highly charged and hydrophobic nature. Three of these four peptides (561 M, P, and Q) were able to release 561 antibody prebound to KG1a or tHL60 cells. The linear hexapeptide library was obtained from Dr. George Smith at the University of Missouri. The random hexapeptide sequence was inserted into the pIII gene of the vector FUSE5. Dynabeads M-450 CD34 (561) batches CEL R21 and CEL R73 were obtained from Dynal A.S. Oslo, Norway.

Biopanning procedures were conducted as described in Example 1 above. The hexapeptide library was amplified in 2 L of terrific broth (500 ml per 2 L flask). Briefly, K91Kan cells were grown to an OD550~2.0 at 225 rpm, 37° C. After 15 minutes at 50 rpm for pili regeneration, the cells were infected with 10 ul (~$10^2$ physical particles) of the primary library.

The amplified library was concentrated with PEG/NaCl from ~2 L to 1 ml.

The amplified library was titered.

Four rounds of biopanning were performed following the procedures. Three different ratios (100:1 or 10:1 and 1:1) of phage particles to 561-Dynabead molecules were used. Each successive step of biopanning was preceded by an amplification of the eluted phage. $1\times10^{11}$ TU of the library were used in the first biopanning.

Tetracycline/Kanamycin resistant colonies from the third and fourth biopanning were grown and supernatants containing the bacteriophage were PEG precipitated.

DNA was prepared from the PEG concentrated phage for DNA sequence analysis.

DNA sequence was determined following "cycle" sequencing analysis using the Applied Biosystems PRISM fluorescent dyedeoxy terminators and oligonucleotide primer JTL2.

DNA sequence analysis was determined for 160 bacterial clones selected from the fourth round of biopanning using CEL R21 561-Dynabeads, two predominant sequences were identified.

DNA sequence analysis was determined for 160 bacterial clones selected from the third and fouth rounds of biopanning using CEL R21 561-Dynabeads, two additional predominant sequences were identified.

A major characteristic of these hexapeptide sequences is that they contain both highly charged and hydrophobic residues.

No direct homology of the predominant peptide sequence with the CD34 antigen was identified.

A similarity in charge and hydrophobicity was observed between the predominant linear hexapeptide sequences and a region of the CD34 antigen (a.a. # 149 to 219) in the extracellular domain.

Phage display biopanning in solution with CEL R21 561-beads selected two predominant linear hexapeptide sequences 561 L: TCTNCH (SEQ ID NO:56) and 561M: ACKWCR (SEQ ID NO:50). The same biopanning in solution was repeated using a different lot of (CEL R73 ) 561-beads, in addition to peptide M: ACKWCR (SEQ ID NO:50), two additional predominant sequences were identified 561P: QKTDAY (SEQ ID NO:87), 561Q: PANVSL (SEQ ID NO:94). All 4 predominant hexapeptide sequences contain highly charged and hydrophobic residues. (PANVSL) (SEQ ID NO:94) has direct homology to the CD34 antigen (PANVST (SEQ ID NO:190), a.a.# 93–97). These data suggest that the structure of the CD34 epitope recognized by the 561 antibody is likely to include a loop, possibly containing hydrophobic residues, stabilized by ionic interactions mediated through charged amino acids. The complete epitope of the CD34 antigen recognized by the 561 antibody may be a discontiouous region including the PANVST (SEQ ID NO:190) region at amino acids 93–97 and a loop within the arginine-rich region. These four predominant peptides (561 L, M, P and Q) were synthesized and tested for their ability to serve as release reagents in the KG1a or tHL60 cell-based FACS assay. Three of these peptides, 561 M, P and Q, were able to release 561 antibody prebound to KG1a or tHL60 cells.

TABLE 23

Summary of Hexapeptide Sequences Identified by Phage Display with 561 CEL R21 Beads

| SEQUENCE | # OF CLONES |
|---|---|
| ACKWCR(SEQ ID NO:50) (561M) | 61 |
| TCKWCR(SEQ ID NO:54) | 2 |
| RVSWCR(SEQ ID NO:55) | 1 |
| TCTNCH(SEQ ID NO:56) (561L) | 19 |
| TCTKVH(SEQ ID NO:57) | 2 |
| FFRDVY(SEQ ID NO:58) | 1 |
| FLHECY(SEQ ID NO:59) | 1 |
| YIKGLF(SEQ ID NO:60) | 1 |
| YIGTDH(SEQ ID NO:61) | 2 |
| VIMEEA(SEQ ID NO:62) | 2 |
| KLIATA(SEQ ID NO:63) | 1 |
| TAAHTW(SEQ ID NO:64) | 1 |
| CSLHHY(SEQ ID NO:65) | 1 |
| VLLSDN(SEQ ID NO:66) | 1 |
| MVWVNN(SEQ ID NO:67) | 1 (2) |

TABLE 24

Summary of Hexapeptide Sequences Identified by Phage Display with 561 CEL R21 Beads

| SEQUENCE | # OF CLONES |
|---|---|
| SWNYTH(SEQ ID NO:68) | 1 |
| RVSGVG(SEQ ID NO:69) | 1 |
| RVSGCR(SEQ ID NO:70) | 2 |
| RYGGSF(SEQ ID NO:71) | 1 |
| LRKVNG(SEQ ID NO:72) | 1 |
| WSVQRD(SEQ ID NO:73) | 1 |
| FSIGAG(SEQ ID NO:74) | 1 |
| SPFVTM(SEQ ID NO:75) | 1 |

TABLE 25

Summary of Hexapeptide Sequences Identified by Phage Display with 561 CEL R73 Beads

| SEQUENCE | 3RD BIOPANNING # of clones | 4TH BIOPANNING # of clones |
|---|---|---|
| (SEQ ID NO:50) ACKWCR | 16 | 45 |
| (SEQ ID NO:84) ACEWCR | 1 | 1 |
| (SEQ ID NO:85) AWWSNT | 1 | |
| (SEQ ID NO:86) WCRRIT | 1 | |
| (SEQ ID NO:87) QKTDAY | | 22 |
| (SEQ ID NO:88) QKAEAY | | 2 |
| (SEQ ID NO:89) QKADAY | | 3 |
| (SEQ ID NO:90) QETDAY | | 1 |
| (SEQ ID NO:91) QEADAY | | 1 |
| (SEQ ID NO:92) QQADAY | | 2 |
| (SEQ ID NO:93) QQTDAY | | 1 |
| (SEQ ID NO:94) PANVSL | | 18 |
| (SEQ ID NO:95) PADVSL | | 2 |
| (SEQ ID NO:96) PPNVSL | | 1 |
| (SEQ ID NO:97) TPNVSL | | 1 |

EXAMPLE 14

561 Antibody Selection of Cyclic Peptides ($XCX_6CX$) Through Phage Display Technology.

A dominant cyclic peptide sequence was identified from a constrained loop library, $XCX_6CX$. In this library, X could be any amino acid except Trp or Met. Multiple variant sequences represented by one to three phage clones each also were identified. No direct homology to the CD34 antigen was observed with the consensus sequence. However, relatedness to a region of the CD34 antigen corresponding to a potential antigenic peak was identified. These data suggest that the 561 antibody recognizes a specific conformational epitope within the CD34 antigen.

The purpose of this study was to identify a potential stem cell release reagent for the 561 antibody. Previous phage display studies (see Example 12 above) identified five linear hexapeptide sequences that bind the 561 antibody. A major characteristic of these hexapeptide sequences is their basic nature, each containing at least two arginine residues. Two of these peptides (561C and 561D) were able to release 561 antibody prebound to KG1a cells (data not shown).

Examination of the published CD34 antigen protein sequence did not reveal any direct homologies with the linear hexapeptides. Only five arginine residues are present (from amino acids 150 to 219) in the CD34 antigen extracellular domain. This region also is the stretch of CD34 containing the only six cysteine residues (amino acids 146-211). The structure of the CD34 antigen in this region potentially includes three disulfide-linked loops stabilized by multiple charged residues. This analysis suggests that the 561 antibody may preferentially bind a constrained, cyclic peptide more readily than a linear peptide.

Biopanning with the 561 antibody of a constrained library in which cyclic peptide loops are expressed on the surface of fd phage was performed. A predominant cyclic peptide sequence and multiple variants of the motif were identified. Preparation of the cyclized form of the predominant peptide sequence is a prerequisite to functional testing as a stem cell release reagent.

The constrained cyclic peptide library obtained from Dr. Jamie Scott (Simon Fraser University, Vancouver, British Columbia) was constructed in the vector F88.4. This vector carries a tetracycline resistance gene and has two pVIII genes, the wild-type and a synthetic gene containing the cyclic peptide sequence. The pVIII gene encodes the major coat protein of filamentous bacteriophages. In the F88.4 vector normal, wild-type coat protein is made in addition to the coat protein containing an additional cyclic peptide loop.

Biopanning procedures were conducted as described above for selection of linear hexapeptides.

Super Broth: bactotryptone, Difco Lot 9761; yeast extract, Difco Lot 795698, sodium chloride, Aldrich # 7647-14-5, Lot 12327CX.

NZY broth, Gibco #M36350B, Lot 1 1H1026B.

JTL5 oligonucleotide primer, purchased from Operon, Technologies, Inc.

JTL5: 5' TTT GAT GCC AAT AGT AGC ACC AAC GAT AAC 3'This primer allows DNA sequence determination of the anti-sense strand of the F88.4/XCX6CX library clones. 561 antibody, 4.7 mg/ml, obtained from Dynal AS.

Other materials were as described above.

Methods:

The cyclic library was amplified in 4 L of superbroth (500ml per 2L flask). Briefly, K91kan cells were grown to an OD550=1.73 at 225 rpm, 37° C. After 15 minutes at 50 rpm for pili regeneration, the cells were infected with the library at a moi=1 (multiplicity of infection of 1 phage particle per 1 cell).

The amplified library was concentrated with PEG/NaCl from ~4.4 L to approximately 9 mls.

The amplified library was titered.

Four steps of biopanning were performed as described above. The amount of 561 antibody used per step was: 10 μg-1st biopanning, 10 μg-2nd biopanning, 1 μg-3rd biopanning, and 1 μg-4th biopanning ("10-10-1-1"). Each successive step of biopanning was preceded by an amplification of the eluted phage. $5\times10^{10}$ TU of the library were used in the first biopanning.

Tetracycline/kanamycin resistant colonies from the fourth biopanning were grown and supernatants containing the bacteriophage were PEG precipitated.

DNA was prepared from the PEG concentrated phage for DNA sequence analysis.

DNA sequence was determined following "cycle" sequencing reactions using the Applied Biosystems PRISM fluorescent dideoxy terminators and oligonucleotide primer JTL5.

Antigenic potential profile of the CD34 antigen was determined using MacVector™ 4.1 software.

Results

Amplification of the cyclic peptide library was performed resulting in a final titer of $2.5\times10^{13}$ TU/ml (TU=transducing units), ~9ml, stored at 4° C.

Four biopanning steps were performed.

DNA sequence analysis was determined for bacterial clones from the fourth biopanning.

A predominant cyclic peptide sequence (24 clones) was identified upon translation of the DNA sequence (Table 26 below).

Multiple variant cyclic peptide sequences were identified, each represented by 1–3 different clones (Table 26 below).

No direct homology of the predominant cyclic peptide sequence with the CD34 antigen was identified.

A similarity in charge and hydrophobicity was observed between the predominant cyclic peptide sequence and a region of the CD34 antigen which also corresponds to a potential antigenic peak.

Phage display biopanning with the 561 antibody selected a predominant cyclic peptide sequence: Q C I D E F L R C I. Multiple variants related to the primary motif also were identified. This analysis indicates that a looped peptide containing six amino acids in the loop can be bound by the 561 antibody. Its specific amino acid composition and sequence are probably analogous to or mimic the natural epitope of the CD34 antigen.

Multiple variants of the predominant sequence indicate that the general features of the major cyclic peptide are required for binding to the 561 antibody. Highly charged and hydrophobic residues within the looped peptides support the previous conclusions drawn from the linear hexapeptide biopanning analysis (Example 12 above). The repeated selection for peptides containing arginine residues may be indicative of specific recognition of the region within the CD34 antigen containing the only five arginine residues in the extracellular domain of the protein.

The consistent presence of hydrophobic residues such as F, phenylalanine and L, leucine, suggest that a non-ionic interaction is also a part of the epitope recognized by the 561 antibody. Taken together, the data suggest that the 561 antibody can recognize a conformationally restricted peptide sequence. The identification of a consensus sequence upon biopanning of the cyclic peptide library and multiple sequences upon biopanning of the linear hexapeptide library suggest that the 561 antibody recognizes an epitope displayed within the arginine-rich and cysteine-containing region of the CD34 antigen (amino acids 146–219). The structure of the CD34 epitope recognized by the 561 antibody is likely to include a loop, possibly containing hydrophobic residues, stabilized by ionic interactions mediated through charged amino acids. Biopanning the linear hexapeptide library with the 561 antibody directly attached to magnetic beads resulted in the identification of one hexapeptide (P A N V S L) (SEQ ID NO:94) with direct homology to the CD34 antigen (P A N V S T) (SEQ ID NO:190). The complete epitope of the CD34 antigen recognized by the 561 antibody may be a discontinuous region including the P A N V S T (SEQ ID NO:190) region at amino acids 93–98 and a loop within the arginine-rich region.

Functional testing of a cyclic peptide as a stem cell release reagent awaits synthesis of sufficient quantities of the linear form of the predominant cyclic peptide sequence followed by chemical cyclization and HPLC purification of the cyclized peptide. Initial testing will be performed using the KG1a or tHL60 cell-based FACS assay. If the cyclic peptide can compete off prebound 561 antibody, then it will be tested in a small scale bead assay. Final testing would be performed in the Isolex® cell selection system (Baxter Immunotherapy Division, Irvine, Calif.).

The cyclic peptide sequence (X C $X_6$ C X) is encoded from nucleotide positions 70–100 (of the coding region) in a synthetic copy of the p8 gene in the F88.4 vector. Third position nucleotide changes from the wildtype codons prevent genetic recombination with the wild type gene. Both copies of the p8 gene are expressed resulting in a normal major coat protein intermixed with the cyclic peptide containing coat protein packaging the single-stranded DNA of the bacteriophage.

JTL5 oligonucleotide primer is located on the anti-sense strand (bottom) from nucleotide positions 228–199 (5'→3').

TABLE 26

Summary of Phage Display Selected Cyclic Peptide Sequences for the 561 Antibody

| SEQUENCE | NUMBER OF CLONES |
|---|---|
| Q C I D E F L R C I(SEQ ID NO:101) | 24 |
| D C I D T F L R C V(SEQ ID NO:102) | 1 |
| S C I D D F L R C A(SEQ ID NO:103) | 1 |
| Q C I D A F R R C I(SEQ ID NO:104) | 1 |
| N C I D T F V A C A(SEQ ID NO:105) | 1 |
| N C I D K F L A C V(SEQ ID NO:106) | 2 |
| Q C I D E L L R C I(SEQ ID NO:107) | 1 |
| N C I D V F L T C V(SEQ ID NO:108) | 1 |
| D C I E R F L T C V(SEQ ID NO:109) | 1 |
| N C I E I F I S C V(SEQ ID NO:110) | 1 |
| S C I E T F L Q C V(SEQ ID NO:111) | 1 |
| G C I E R F F Q C V(SEQ ID NO:112) | 1 |
| N C I E S F L R C V(SEQ ID NO:113) | 1 |
| S C I N R F L T C V(SEQ ID NO:114) | 1 |
| S C T N R F L T C V(SEQ ID NO:115) | 1 |
| S C P V A I A S C T(SEQ ID NO:116) | 1 |
| N C V D Q F I H C V(SEQ ID NO:117) | 1 |
| N C V E A F L I C A(SEQ ID NO:118) | 2 |
| N C V D K F L A C A(SEQ ID NO:119) | 1 |
| Q C I A E F L R C I(SEQ ID NO:120) | 3 |
| D C V E Q F L T C V(SEQ ID NO:121) | 1 |
| L C R L L K Q L C N(SEQ ID NO:122) | 1 |
| I C T D R Y P P C T(SEQ ID NO:123) | 1 |

Homology of the cyclic peptides to the CD34 antigen are not direct, one amino acid for another amino acid. One alignment has homology to amino acids 168–171 and possibly the arginine at 175; another alignment possibly has homology to amino acids 177–181. The potential disulfide-linked loop from amino acids 168 to 184 of the CD34 antigen may be mimicked by a smaller loop such as the cyclic peptide with homology to the beginning and end of the loop.

```
CD34 aa168-184 C A E F K K D R G E G L A R V L C (SEQ ID NO: 212)

561 CYCLIC PEPTIDE   a: Q C I D E F L R C I       (SEQ ID NO: 101)

                     b: Q C I D E F L R C I       (SEQ ID NO: 101)
```

The underlined region has antigenic potential as determined using MacVector 4.1 software.

EXAMPLE 15

Effect of pH on Peptides as Release Reagents for the 561 Antibody

Five peptides identified through phage display technology with the 561, anti-CD34 antibody, were tested in a FACS cell-based assay using KG1a cells. All five peptides show significant release activity on pre-bound 561 antibody at pH 4 and not at pH 7.

Unlike crude hexapeptides, the HPLC purified 561C and 561D peptides did not show release activity. The effect of pH on the ability of peptides to displace pre-bound 561 antibody was examined.

The peptides (see Table 27 below) were synthesized by Research Genetics and tested without purification. The 9069 antibody was used as a positive control and released with the 9069N peptide (Ac-Q Q G W F P-K D) (SEQ ID NO:9). This control served to test for the KG1a cells and the goat-anti-mouse FITC secondary detection antibody. Hexapeptide sequences identified for the 561 antibody were tested for their ability to displace prebound 561 antibody.

Crude peptides (see Table 27 below) were purchased from Research Genetics Inc., Huntsville, Ala.

Purified 561C and 561D peptides were purchased from American Peptide Company, Sunnyvale, Calif.

Methods:

HPLC-purified peptides 561C and D were tested in the cell-based KG1a FACS assay.

pH of crude and purified 561C and 561D peptides was examined.

Functional release activity of purified 561D peptide at pH 4 and 6 was tested.

Functional release activity of purified 561C and 561D peptides at pH 4, 5, 6, 7, 8, and 9 was tested.

Functional release activity of crude 561A,B,C,D, M, P, Q, CDR2H, CDR2L, CDR3H, CDR3L, 34B, 34C,34D,34E and 34F peptides adjusted to pH 7 and pH unadjusted (~pH3.8–4.3) was tested.

Results:

HPLC-purified 561C and D peptides did not function as release reagents in the FACS cell-based assay.

The crude 561C and 561D peptides dissolved at approximately pH 4.

The HPLC-purifed 561C and D peptides dissolved at approximately pH 6.

The purified 561C and D peptides adjusted to ~pH 4 resulted in functional activity as release reagents.

The purified 561 C and D peptides tested at pH 4–9 only showed significant release activity in the FACS cell-based assay at pH 4 or pH 9.

Crude peptides 561C,D,M, P, Q, CDR2H, and CDR3L peptides pH unadjusted (around pH 3.8–4.3) showed functional release activity in the FACS cell-based assay. At pH 7, none of these peptides showed release activity.

Crude peptides 561A, B,CDR2L, CDR3H, 34B, 34C, 34D, 34E and 34F did not show functional release activity pH unadjusted (about pH 4) or at pH 7.

Effectiveness of phage display-defined hexapeptides as 561 antibody release reagents was analyzed at different pH values. At low pH (~4), the 561 C,D,M, P, Q, CDR2H and CDR3L peptides showed significant release activity in the KG1a cell-based FACS assay. These peptides did not show release activity at pH 6 or pH 7. Release activity also was observed at pH 9 for the 561D peptide. Utility of the active release peptides requires conditions that are not harmful to the stem cells to be isolated. Short-term viability of the cells after incubation for 30 minutes at pH 4 was good, however, long-term effects were not studied.

Examination of the 561 antibody sequence indicates that the complementarity determining regions, CDRs, contain multiple (6) aspartic acid residues and two histidine residues. These amino acids would be affected at lower pH. The protonation of the aspartic acid groups could serve to neutralize an ionic interaction with the CD34 antigen thus promoting dissociation. The inability of the peptides to cause complete dissociation even at low pH suggests that these peptides do not adequately mimic the true sequence/conformation of the natural CD34 epitope recognized by the 561 antibody. The identification of a consensus cyclic peptide and multiple conservative variants indicate that a constrained peptide may be the preferred peptide binding motif. The effect of pH 9 on the release reaction is not understood. The 561 antibody may be undergoing a conformational change that aids peptide release.

The observed pH effect on the ability of the phage display-defined peptides to serve as release reagents is specific for the 561 antibody. Titrations of pH with the 9069N peptide has no effect on release activity for the 9069 antibody bound to KG1a cells. The ability to select, define and optimize a peptide release reagent for any antibody is dependent upon the specific biochemical properties of the given antibody and its specific interaction with its antigen.

TABLE 27

Summary of Peptides Synthesized for Testing on the 561 Antibody

| Peptide | Sequence |
|---|---|
| **Phage Display Selected Hexapeptide Sequences** | |
| 561A | R H R H R H(SEQ ID NO:34) |
| 561B | K R H K R H(SEQ ID NO:35) |
| 561C | R T K T R F(SEQ ID NO:36) |
| 561D | T R V P R R(SEQ ID NO:37) |
| 561E | R H R P R H(SEQ ID NO:38) |
| **Antibody CDR Peptides** | |
| 561CDR1H | D—N Y W M Q—K(SEQ ID NO:39) |
| 561CDR2H | A I Y P G D G D T R Y T Q K F V V(SEQ ID NO:40) |
| 561CDR3H | N D G Y F D A M D Y(SEQ ID NO:41) |
| 561CDR1L | D—S A S S S V T F M H—K(SEQ ID NO:42) |
| 561CDR2L | D T S K L A S(SEQ ID NO:43) |
| 562CDR3L | D—Q Q W N S N P L T—K(SEQ ID NO:44) |
| 561CDR1H.2 | D—N Y W M Q—K D(SEQ ID NO:45) |
| 561CDR1L.2 | K D—S A S S S V T F M H—K D(SEQ ID NO:46) |
| 561CDR3H.2 | A R N D G Y F D A M D(SEQ ID NO:47) |
| 561CDR2L.2 | H D T S K L A S Q V—D(SEQ ID NO:48) |
| **Phage Display Selected Hexapeptides Using 561-Beads, Lot CEL-R21** | |
| 561L | T C T N C H—K D(SEQ ID NO:49) |
| 561M | A C K W C R(SEQ ID NO:50) |
| **Phage Display Selected Cyclic Peptides Using 561** | |
| 561N | Q C I D E F L R C I—K D(SEQ ID NO:98) |
| 561R | D—Q C I D E F L R C I—K D(SEQ ID NO:99) |

TABLE 27-continued

Summary of Peptides Synthesized for Testing on the 561 Antibody

| Peptide | Sequence |
|---|---|
| 561S | D—Q C I D E F L R C I—D(SEQ ID NO:100) |
| **Phage Display Selected Hexapeptides Using 561-Beads, Lot CEL-R73** | |
| 561M | A C K W C R(SEQ ID NO:50) |
| 561P | Q K T D A Y—K D(SEQ ID NO:51) |
| 561Q | K D—P A N V S L—K D(SEQ ID NO:52) |
| **CD34 Peptide Homologous to 561Q Peptide** | |
| 34L | K D—P A N V S T—K D—C(SEQ ID NO:53) |

Summary of modification of 561 release in FACS assay:

The ability of chemical reagents to enhance peptide-dependant release of captured CD34+ cells from the 561 antibody was examined. The purpose of these experiments was to determine if mild conditions (greater than pH4) could be established in which phage displayed selected peptides could trigger release of bound antibody. Previous studies indicated a requirement for low pH (about pH4) for effective cell release. Since long-term viability of the low pH-released cells was not known, conditions which could alter the pH to a more neutral value (about pH5–7) were desirable.

Reagents which were known to affect electrostatic and hydrogen bonding interactions of proteins were tested in addition to excluded-volume polymers. Included in these studies were sodium chloride, sodium acetate, magnesium chloride, calcium chloride, polyethylene glycol (PEG), ficoll, sodium succinate, sodium citrate, protamine sulphate, spermine, and polybrene.

Only sodium acetate showed significant activity as an enhancement reagent for peptide mediated release of CD34+ selected cells. The presence of multiple (6) aspartic acid residues in the CDR, complementarity determining regions of the 561 antibody variable regions suggests a highly charged interaction at the surface of the antigen/antibody binding cleft. The ability of acetate to mimic the aspartic acid side chains may explain the ability of sodium acetate and not sodium chloride to enhance release. Less dramatic results were obtained with magnesium chlordie and PEG. All other compounds tested did not show significant enhancement of peptide-mediated cell release.

EXAMPLE 16

Glutamate-Rich Peptide as a Competitor of Antibody/Epitope Interaction

A glutamate-rich peptide was tested for its ability to serve as a competitor of a specific anti-glutamate rich epitope antibody (anti-glu-glu) bound to its antigen. This study was initiated to establish the feasibility of constructing a recombinant anti-CD34 molecule containing a glutamate-rich sequence which could then be captured with the specific anti-glu-glu antibody. A competitive peptide release reagent was established as a feasible, cost effective reagent. This study also supports the plan to identify and characterize specific peptides for use as release reagents against cell-capture antibodies.

A glutamate-rich peptide was tested for its ability to serve as a competitor of a specific anti-glutamic acid-rich epitope (anti-glu-glu) antibody bound to its antigen. This assay was performed in a competitive ELISA format. This study was initiated to establish the feasibility of constructing a recombinant anti-CD34 antibody containing a glutamate-rich sequence which could be used to capture human stem cells. A competitive peptide release reagent was established as a potential feasible, cost effective reagent for release of captured stem cells.

The source of glu-glu antigen was a single chain antibody containing this glu-glu antigenic sequence (TAI) containing glu-glu tag sequence (=SCA-EE) in the form of bacterial lysate (Dade Diagnostics, Miami, Fla.). The anti-glu-glu monclonal antibody was also obtained from that group. The test reagents included a glu-glu peptide (AEEEEYMPMEG, American Peptide Company, Sunnyvale, Calif.), glutamic acid, diglutamic acid, poly-glutamic acid and poly-aspartic acid (all from Sigma).

Horse radish peroxidase conjugated goat anti-mouse IgG (H+L), TMB substrate, and hydrogen peroxide were purchased from KPL (Gaithersburg, Md.).

SCA-EE (15 and 30 ug/ml) was used to coat microtiter dishes.

Anti-glu-glu antibody (anti-EE) was added from 0 to 2187 ng/ml to establish a titration of the antibody. HRP goat anti-mouse IgG (H+L) and TMB reagent were used to detect bound antibody. Absorbance readings were measured at 450 nm.

SCA-EE was used to coat microtiter dishes, followed by addition of 50–300 ng/ml anti-EE. Plates were washed and then competitors were added:

| | |
|---|---|
| 100 nM–100 μM | peptide (A—EEEEEYMPME—G)(SEQ ID NO:213) |
| 500 nM–500 μM | glutamic acid (E) |
| 250 nM–250 μM | diglutamic acid (EE) |
| 1 nM–1 μM | poly glutamic acid (EEEEEEEEEEEE) (SEQ ID NO:214) |
| 1 nM–1 μM | poly aspartic acid (DDDDDDDDDDD) (SEQ ID NO:215) |

Amount of remaining anti-EE monoclonal antibody was detected by the HRP-conjugated goat anti-mouse IgG (H & L) and TMB reagent. Absorbance readings were measured at 450 nm. Anti-glu-glu antibody was titrated with SCA-EE.

Among the five different reagents analyzed, only the glu-glu peptide could displace bound anti-EE antibody.

These experiments verified the ability of a specific short peptide to displace a prebound antibody from its antigen. Other reagents tested were not effective at competing off the antibody. This observation supports the specific nature of the peptide antibody interaction.

The incorporation of the peptide epitope sequence into a recombinant protein will allow capture of that protein with the anti-glu-glu antibody and subsequent competitive release with peptide. Recombinant forms of the anti-CD34 antibody, 9069, can be constructed to include a glu-glu sequence. The anti-glu-glu antibody could be attached to a magnetic bead. Release of captured CD34+ cells would then be accomplished with addition of the glu-glu peptide. Released cells would still have the anti-CD34 antibody attached.

EXAMPLE 17

Anti-BrCa antibody releasing peptides.

Biopanning as described in Example 1 above was performed to identify peptides that could release the 9187 anti-breast-cancer monoclonal antibody from cells carrying this breast cancer antigen. The hybridoma which produces the 9187 monoclonal antibody (Baxter Hyland, Hayward, Calif.) was deposited with the American Type Culture Collection, Rockville, Md., under the provisions of the Budapest Treaty on the international recognition of the deposit of microorganisms for the purposes of patent procedure. The 9187 hybridoma was assigned deposit number ATCC HB-11884, effective May 9, 1995.

TABLE 28

The following is a list of potential 9187-releasing peptides which were identified by biopanning:

| Hexapeptide Sequence | # of clones |
|---|---|
| R W R W R H(SEQ ID NO:124) | 27 |
| A R F P R R(SEQ ID NO:125) | 3 |
| R H H L Y R(SEQ ID NO:126) | 3 |
| W Y R S H R(SEQ ID NO:127) | 2 |
| T R V P R R(SEQ ID NO:128) | 4 |
| T P R N P R(SEQ ID NO:129) | 1 |
| L R R T F W(SEQ ID NO:130) | 1 |
| L V R I Q F(SEQ ID NO:131) | 1 |
| L V R V W F(SEQ ID NO:132) | 1 |
| L T R T V F(SEQ ID NO:133) | 1 |
| R T K T R F(SEQ ID NO:134) | 1 |

EXAMPLE 18

Selection of CD34+ Cell from Normal Mobilized Human Peripheral Blood Using Peptide Release Process Validation of the peptide release process for the selection of CD34+ cells from human peripheral blood was performed on the Isolex® 300SA cell separator (Baxter Immunotherapy Division, Irvine, Calif.). Ten CD34+ cell selections using 9069N peptide as the releasing agent were performed using G-CSF mobilized peripheral blood from normal volunteer donors. A full apheresis unit was processed in each selection.

The starting peripheral blood mononuclear cell product contained $2.4\times10^{10}$ to $4.48\times10^{10}$ mononuclear cells with starting CD34+ cell content of 0.45% to 1.75%. The 9069N peptide used to release the captured cells was in a lyophilized form (N=6 experiments) or a liquid form (N=4 experiments). FACS analysis and colony assays were performed on all selection products.

The G-CSF mobilized peripheral blood products were obtained from normal volunteer donors.

The 9069N Peptide (Ac-Gln-Gln-Gly-Trp-Phe-Pro-Lys-Asp) used as a lyophilized product was obtained from American Peptide.

The 9069N Peptide, Bachem, C/N.

The 9069N Peptide used as a liquid product was obtained from Baxter (Immunotherapy?), The 9C5 mAb (also described above as 9069 mAB, ATCC# HB-11646)was obtained from Baxter Immunotherapy Div.

Immune Globulin Intravenous (Gammagard®), Baxter, Hyland Div.

25% HSA, Baxter, Hyland Div.

4% Sodium Citrate, Baxter, Code 4B7867

Dulbecco's Phosphate Buffered Saline ($Ca^{2+}$, $Mg^{2}$+ free), BioWhittaker,

Sterile Water, Baxter, Hyland Div., Code 3475 & 3476

Sheep Anti-Mouse IgG Coated Paramagnetic Beads, Dynal, P/N Isolex® 300SA Disposable Sets, Baxter, Immunotherapy Div.

Millex-6V 0.22 μm Sterile Filter Unit, Millipore 600 mL Transfer Pack, Baxter, Code 4R2023

1,000 mL Transfer Pack, Baxter, Code 4R2032

2,000 mL Transfer Pack, Baxter, Code 4R2041

Sample Site Coupler, Baxter, Code 4C2405

X-Vivo 10, Bio-Whittaker, C/N 04-6950

Plasma Transfer Sets, Baxter, Code 4C2243

Sterile Syringe, Baxter

12×75 mm P/P w/cap Tubes, Baxter, C/N T1340-102

12×75 mm Culture Tubes, Baxter, C/N T1225-3

16 G 1 ½ Precision Glide Needle, Becton Dickinson

Simultest Control (Mouse $IgG_1$ & $IgG_{2a}$), Becton Dickinson

Simultest Leucogate Control, Becton Dickinson

CD45-FITC, Becton Dickinson

CD34-PE, Becton Dickinson

Calcein, Molecular Probes, Inc.

Mouse IgG, Calbiochem

Isolex® 300SA Cell Separator

Glas-Col® Lab Rotator

Beckman GS-6R Centrifuge

Sysmex F-500 Automated Particle Counter

Terumo SCD 312, Sterile Connecting Device

Dynal® MPC-1 Magnetic Cell Separator

To prepare calcein (viability stain) 5 μL of 4 mM calcein was added to 5 mL of DPBS to form a stock solution, which was stored in the dark at 4° C. for no longer than 5 days.

The working solution of calcein was prepared at a 1:8 dilution of 4 μM calcein in DPBS which was stored in the dark at 4° C. for no longer than 10 hours.

The each peripheral blood mononuclear cell (PBMC) product was transferred into a 600 mL transfer pack, then weighed to determine the blood product volume (1 g=1 mL). A 0.5 mL aliquot was removed for total cell count and for viability determination using the acridine orange/propidium iodide (AO/PI) viability assay. The PBMC was washed once in the 600 mL transfer pack with 500 mL of $Ca^{2a}$+ and $Mg^{2a}$+ free DPBS containing 1% HSA and 0.2% sodium citrate (processing buffer), and centrifuged at room temperature for 10 min. at 1,000 rpm (200×g) with no brake. Most of the supernatant was aspirated, and the cells were thoroughly resuspended in the remaining supernatant (usually <85 mL). The cell volume was determined by weight, and 0.5 mL of resuspended cells was sterilely removed using a syringe for total cell and viability counts.

A 5% Gammagard® solution was prepared according to the manufacturer's instructions. Ten percent (v/v) of a 5% Gammagard® solution was added sterilely using a syringe into the bag of resuspended PBMC for a 0.5% Gammagard® blocking concentration. The Gammagard®/cell mixture was incubated for 15 min. at room temperature.

After blocking with Gammagard®, the cells were sensitized with 2.5 mg anti-CD34 monoclonal antibody, 9C5, regardless of the total cell number being processed. The sensitization volume with antibody was set at 100 mL, and the appropriate amount of processing buffer was sterilely added using a syringe to the Gammagard® blocked cell suspension followed by 2.5 mL of a 1 mg/mL 9C5 mAb (1 vial). The antibody-cell mixture was incubated "end-over-end" for 15 min. at room temperature on a rotator set at 4 rpm.

The antibody sensitized PBMC were washed two times in 500 mL of processing buffer per wash to remove the unbound antibodies. The cells were centrifuged at room temperature for 7.5 min. at 1,500 rpm (400×g) on low brake. If the supernatant was still reddish after centrifugation, the PBMC were centrifuged again with no brake before decanting the supernatant. Occasionaly this incomplete pelleting of cells was observed when processing $>3\times10^{10}$ PBMC. After the last wash, most of the supernatant was aspirated, and the pelleted cells were resuspended in the remaining buffer and weighed to determine the cell volume (usually ≦80 mL). A 0.5 mL aliquot of the cell suspension was sterilely removed using a syringe for total cell and viability counts.

One vial of sheep anti-mouse IgG coated paramagnetic beads ($4\times10^9$ beads/vial) was used per selection procedure regardless of the cell number being processed. The beads were washed 3 times in 20 mL of processing buffer/wash using Dynal's MPC 1 magnet. After the last wash, the beads were resuspended in 10 mL of processing buffer and kept at room temperature until needed.

The sensitized cells were slowly injected into the Isolex® 300 primary chamber. Ten milliliters of washed sheep anti-mouse IgG coated paramagnetic beads was then injected into the chamber followed by 10 mL of Gammagard® to obtain a 1:10 v/v of Gammagard® to total rosetting volume. The rosetting was conducted at a volume of 100 mL. Capture of CD34+ cells from PBMC was performed according to the pre-set program in the Isolex® 300SA, as described below.

The cell/bead rosettes were washed three times in processing buffer according to the pre-set program in the Isolex® 300SA. The cell supernatant and wash supernatants were collected and pooled. The final supernatant volume was determined, and 0.5 mL was removed using a syringe for total cell count.

Release of CD34+ cells bound to the paramagnetic beads was performed in 100 mL of a 1 mG/mL 9069N peptide solution. For lyophilized 9069N peptide synthesized by American Peptide, ~105 mg of peptide was dissolved in ~10.5 mL of processing buffer to obtain a 10 mg/mL stock solution. The stock solution was sterile filtered through a 0.22 μm sterile filter. For the lyophilized peptide synthesized by Bachem, ~110 mg of 9069N was added to 9.5 mL of Dulbecco's phosphate buffered saline (DPBS). The peptide was dissolved by adjusting the pH of the peptide to ~7 by dropwise addition of 1 N sodium hydroxide. Human serum albumin and sodium citrate were added to obtain 1% and 0.2% solutions, respectively. The final volume was adjusted to ~11 mL with DPBS, then sterile filtered as above. For the liquid peptide manufactured by Bachem, four vials, each containing 5 mL 9069N at a concentration of 5 mg/mL, were used.

After the last negative fraction wash, the prepared 9069N peptide stock solution was injected into the chamber containing ~60 mL of processing buffer. The final volume was adjusted to 100 mL with processing buffer to obtain a 1.0 mg/mL peptide concentration. The release of captured cells was performed according to the pre-set program in the Isolex® 300, except, the release volume was set at 100 mL and the incubation time was for 30 min. The released cells were collected in a 600 mL transfer pack, then sterilely transferred to 250 mL conical centrifuge tubes. The volume of the cell suspension was determined, and 0.5 mL was removed for total cell count.

The positive cell fraction was centrifuged at room temperature for 5 min. at 1,500 rpm (400×g) with brakes on low. Most of the supernatant was slowly aspirated, and the pelleted cells were resuspended in the remaining supernatant. The positive cell fraction was transferred into a 50 mL centrifuge tube and washed once in 50 mL of processing buffer at room temperature for 5 min. at 1,500 rpm (400×g) with brakes on low . After washing, the positive cell fraction was resuspended in 1% HSA/X-Vivo 10. A 0.5 mL aliquot was removed for total cell and viability counts.

The % capture was calculated based on the equation below:

$$\% \text{ Capture} = 1\frac{(\#\text{ of } MNC \text{ in negative fraction} \times \%\, CD34+\text{ cells in neg. fract})}{(\#\text{ of } MNC \text{ in post-platelet wash} \times \%CD34+\text{ cells in post-platelet})} \times 100$$

The % yield was calculated based on the equation below:

$$\% \text{ Yield} = \frac{(\#\text{ of cells in positve fraction} \times \%\, CD34+\text{ cells in positive fraction})}{(\#\text{ of } MNC \text{ in post-platelet wash} \times \%\, CD34+\text{ cells in post-platelet})} \times 100$$

The % purity was equal to the % CD34+ cells in the positive fraction.

Viability was equal to (Live MNC divided by Tot. MNC)× 100%.

Statistical analysis of the capture, purity, yield, and cloning efficiency of selected CD34+ cells was performed by a two tailed unpaired student's t-test. The confidence interval was set at 95%.

Cloning Efficiency was equal to (Total colonies counted÷# of cells plated)×100%.

Results

The peptide-mediated release process for selecting CD34+cells from G-CSF/GM-CSF mobilized human peripheral blood was a four-hour procedure performed at room temperature. The process included one platelet wash and two antibody washes at 7.5 min./wash. Sensitization with 9C5 mAb (anti-CD34) and resetting with sheep anti-mouse IgG coated paramagnetic beads were performed in 100 mL total volume for 15 min. and 30 min., respectively. The cell-bead rosettes were incubated with 9069N peptide for 30 min. to release the cells from the beads. The process utilized one vial of 9C5 anti-CD34 monoclonal antibody (2.5 mG/vial), one vial of sheep anti-mouse IgG coated paramagnetic beads ($4\times10^9$ beads/vial), and 100 mL of a 1.0 mG/mL 9069N peptide as described in "Methods." The process was performed on full apheresis products.

The total mononuclear cell numbers were acquired before and after each washing procedure to track mononuclear cell loss at different stages of the selection process. A summary of the number of mononuclear cells (MNC) in the starting apheresis product, washed MNC, post-antibody washed MNC, pre-wash positive fraction, and post wash positive fraction is reported in below. On the average, the number of mononuclear cells at the beginning of the process to the end of the platelet wash remained the same. Average cell losses of 20.68% and 19.49% were observed in the post antibody washed MNC and post-wash positive fraction, respectively. These data suggest that ~20% of MNC are lost during the antibody washes, and another 20% MNC are lost in the positive fraction wash. No MNC were lost in the platelet wash. Both antibody and positive fraction washes were centrifuged at 1,500 rpm with low brake. Hence, centrifugation of these washes at higher rpm may minimize cell loss.

A total of ten selection procedures were performed on G-CSF mobilized human peripheral blood products. In six of the 10 procedures, the releasing agent was prepared from a lyophilized 9069N peptide. The remaining four procedures were performed using a liquid filled 9069N peptide as the releasing agent. A summary of the number of mononuclear cells and % CD34+ cells after the platelet wash and the CD34+ cell captures, purities, and yields from the ten selection procedures is shown below. The peripheral blood products after the platelet wash contained $2.43\times10^{10}$ to $4.48\times10^{10}$ mononuclear cells with an average of $3.48\pm0.80\times10^{10}$. The CD34+ cells in the post-platelet washed MNC ranged from 0.3% to 1.75% with an average of 0.86±0.51%. The capture of CD34+ cells ranged from 0 to 90.19% with an average of 63.91±27.42%. The yield of CD34+ cells ranged from 24.99% to 66.32% with an average of 47.63±13.85%. These values were acquired from combining results obtained from using lyophilized peptide preparation (N=6) and results obtained from liquid peptide preparation (N=4) as releasing agents. A comparison of the yield and purity of selected CD34+ cells released by the two formulations of 9069N indicated that an apparent difference in CD34+ cell yield was due to the washing process, and not to the actual release step.

The purities ranged from 68.41% to 96.08% with an average purity of 85.70±10.04%. According to this data, the three washing steps conducted in the Isolex® 300SA were sufficient in removing most non-target cells from the cell/bead mixture.

Colony assays were performed on the CD34+ cell final products. The colonies were counted after day 14 of culture. The colony counts were based on the average colonies counted from triplicate petri dishes containing 2,000 cells plated per petri dish. The types of colonies counted were CFU-GM, Mixed, BFU-E, and Clusters. The average numbers of colonies counted from the 10 CD34+ cell final products were 207±138 CFU-GMs, 8±4 Mixed, 118±56 BFU-Es, and 52±36 Clusters. The average total colonies formed was 386±202, and the cloning efficiency was calculated to be 19.28±10.12%. There was no significant difference between the cloning efficiency of CD34+ cells released with the lyophilized peptide and the liquid filled peptide (p=0.44). According to this data, the CD34+ cell final products obtained had an average colony-forming potential of approximately 20%.

The mononuclear cell populations in the starting product, platelet wash, negative fraction, and positive fraction were analyzed using a lymphocyte gate (low foward and side scatter), monocyte gate, and granulocyte gate based on side scatter vs. FL2 on the leucogate stained fractions using the FACScan. An average of ~60% MNC in the starting, platelet washed, and negative fraction MNC products was observed in the lymphocyte gate, while an average of 92.44±4.56% MNC in the positive fraction was detected in the lymphocyte gate. According to this data, the apheresis products processed in the peptide-release validation had approximately 60% of the starting MNC product in the lymphocyte gate, and ~92% of the MNC in the positive fraction was detected in the lymphocyte gate.

The average MNC found in the monocyte gate was 29.56±6.90%, and after the platelet wash, the average MNC gated was 27.90±6.80%. The average MNC in the monocyte gate of the negative fraction was 26.11±7.56%, while the positive fraction had an average of 5.13±3.40% MNC in the monocyte gate. Thus, the majority of MNC found in the monocyte gate were removed during the washing stage of the cell/bead rosettes. The average starting and post platelet MNC in the granulocyte gate were 9.13±3.38% and 9.61±5.74%, respectively. The negative fraction had an average of 10.44±6.45% MNC in the granulocyte gate, while the positive fraction had an average of 2.26±2.24% MNC gated. This data suggests that the platelet wash did not deplete the apheresis product of granulocytes; however, the granulocytes were removed during the washing of cell/bead rosettes.

No correlation was observed between the ratio of lymphocytes, monocytes, and granulocytes in the starting mononuclear cell products and the CD34+ cell purity, yield, and capture.

These results are summarized in tables 29 and 30 below.

TABLE 29

MONONUCLEAR CELL NUMBERS IN THE STARTING PRODUCT, POST-PLATELET WASH, POST-ANTIBODY WASH, CD34+ CELL PRE-WASH, AND CD34+ POST-WASH

| DONOR I.D. | STARTING MNC | WASHED MNC | POST AB - MNC | POS - BEFORE WASH | CD34+ - POST-WASH |
|---|---|---|---|---|---|
| UOM-2402 | $3.70 \times 10^{10}$ | $3.40 \times 10^{10}$ | $2.85 \times 10^{10}$ | ND | $1.48 \times 10^{8}$ |
| PBSC-M-49-2 | $2.76 \times 10^{10}$ | $2.97 \times 10^{10}$ | $1.94 \times 10^{10}$ | ND | $6.93 \times 10^{7}$ |
| UOM-2708 | $2.00 \times 10^{10}$ | $2.40 \times 10^{10}$ | $1.82 \times 10^{10}$ | ND | $5.60 \times 10^{7}$ |
| UOM-2967 | $2.42 \times 10^{10}$ | $2.60 \times 10^{10}$ | $2.05 \times 10^{10}$ | $3.06 \times 10^{8}$ | $2.42 \times 10^{8}$ |
| UOM-3044 | $5.15 \times 10^{10}$ | $4.48 \times 10^{10}$ | $2.90 \times 10^{10}$ | $1.45 \times 10^{8}$ | $9.10 \times 10^{7}$ |
| PBSC-M-52-2 | $4.08 \times 10^{10}$ | $4.4 \times 10^{10}$ | $3.70 \times 10^{10}$ | $2.10 \times 10^{8}$ | $2.80 \times 10^{8}$ |
| UOM-4168 (Liq. Pep) | $2.51 \times 10^{10}$ | $2.56 \times 10^{10}$ | $2.16 \times 10^{10}$ | $2.10 \times 10^{8}$ | $1.33 \times 10^{8}$ |
| PBSC-M-55-1 (Liq. Pep) | $3.60 \times 10^{10}$ | $3.96 \times 10^{10}$ | $2.80 \times 10^{10}$ | $8.18 \times 10^{7}$ | $4.60 \times 10^{7}$ |
| PBSC-M-56-2 (Liq. Pep) | $4.00 \times 10^{10}$ | $4.20 \times 10^{10}$ | $4.00 \times 10^{10}$ | $2.00 \times 10^{8}$ | $1.53 \times 10^{8}$ |
| UOM-4149 (Liq. Pep) | $3.50 \times 10^{10}$ | $3.85 \times 10^{10}$ | $3.40 \times 10^{10}$ | $1.60 \times 10^{8}$ | $1.12 \times 10^{8}$ |
| AVERAGE | $3.37 \times 10^{10}$ | $3.48 \times 10^{10}$ | $2.76 \times 10^{10}$ | $1.88 \times 10^{8}$ | $1.33 \times 10^{8}$ |
| Std. Dev. | $9.51 \times 10^{9}$ | $8.02 \times 10^{9}$ | $7.66 \times 10^{9}$ | $6.95 \times 10^{7}$ | $7.74 \times 10^{7}$ |
| S.E.M. | $3.01 \times 10^{9}$ | $2.54 \times 10^{9}$ | $2.42 \times 10^{9}$ | $2.63 \times 10^{7}$ | $2.45 \times 10^{7}$ |
| Coeff. Var. (%) | 28.20 | 23.03 | 27.73 | 37.04 | 58.16 |

ND = Not Done

TABLE 30

CALCULATIONS OF THE CAPTURE, YIELD, AND PURITY FROM THE TEN OPTIMIZED ALTERNATE RELEASE PROCESS (OARP) PROCEDURES. CALCULATIONS OF CAPTURE AND YIELD WERE BASED ON THE MNC WASH VALUES

| DONOR I.D. | MNC WASH | CD34 PRE (%) | CD34 POST (%) | YIELD (%) | CAPTURE (%) |
|---|---|---|---|---|---|
| UOM-2402 | $3.40 \times 10^{10}$ | 0.63% | 68.41% | 56.39% | 66.62% |
| PBSC-M-49-2 | $2.97 \times 10^{10}$ | 0.46% | 85.40% | 66.32% | 70.24% |
| UOM-2708 | $2.40 \times 10^{10}$ | 0.45% | 96.08% | 65.70% | 87.63% |
| UOM-2967 | $2.60 \times 10^{10}$ | 1.68% | 91.76% | 50.84% | 90.19% |
| UOM-3044 | $4.48 \times 10^{10}$ | 0.30% | 69.48% | 47.04% | 88.26% |
| PBSC-M-52-2 | $4.4 \times 10^{10}$ | 1.75% | 95.78% | 34.83% | 45.71% |
| UOM-4168 (Liq. Pep) | $2.56 \times 10^{10}$ | 0.90% | 89.58% | 51.71% | * - 0.00% |
| PBSC-M-55-1 (Liq. Pep) | $3.96 \times 10^{10}$ | 0.56% | 79.56% | 24.99% | 77.64% |
| PBSC-M-56-2 (Liq. Pep) | $4.20 \times 10^{10}$ | 1.09% | 89.83% | 31.17% | 47.62% |
| UOM-4149 (Liq. Pep) | $3.85 \times 10^{10}$ | 0.73% | 91.11% | 47.33% | 65.21% |
| AVERAGE | | | 85.70% | 47.63% | 63.91% |
| Std. Dev. | | | 10.04% | 13.85% | 27.42% |

* - Adjusted to 0.00 due to an over estimation of CD34+ cells in the negative fraction. The CD34 stained negative fraction tube for FACS in this particular experiment was not washed as thoroughly as the other fractions resulting in high nonspecific binding of the anti-CD34-PE stain.

EXAMPLE 19

Human CD34+ stem cell selection utilizing peptide release incorporating a specific negative purge processing step.

The three parameters evaluated were one step positive selection and either simultaneous or sequential positive/negative CD34+ cell selection. Positive selection incorporated cell sensitization with an anti-CD34 antibody (9C5, Baxter Immunotherapy Division, Irvine, Calif.), resetting with a sheep anti-mouse coated paramagnetic micro sphere (SAMIgGST beads, Dynal, Oslo, Norway) and cells were release from the bead complexes using the peptide (9069N, Baxter Immunotherapy Division, Irvine, Calif.).

Positive CD34+ cell selection alone, has been shown to reduce tumor burden of autologous grafts. An additional purging step could potentially reduce tumor level to undetectable. Positive/negative selections allowed for the additional removal of contaminating cells through the use of monospecific antibodies. Positive/negative could be accomplished two ways:

Simultaneous; i.e. both the CD 34+ antibody and the purging antibody(s) were added together at the start of the procedure, or Sequential; the positive selection was performed first followed by a negative selection.

Non-Hodgkins Lymphoma and other B-cell malignancies are examples of diseases which would benefit from positive/negative selection of hematopoietic cells. B-cell negative selection is expected to be useful for preparation of purged CD34+ cell populations intended for autograft after high-dose chemotherapy or radiation.

Methods:

Human peripheral blood apheresis products were obtained from human growth factor mobilized normal donors (n=3). The mononuclear cell preparations (MNC) were washed once using working buffer consisting of Dulbecco's phosphate buffered saline (Biowhitaker, Walkersville, Md.) with 1% human serum albumin and 5% sodium citrate (Baxter Hyland, Los Angeles, Calif., v/v, 200×g, 10 minutes at room temperature). The MNC were then divided into $6\times10^9$ cell aliquots for the procedure and each was treated as follows:

Positive Selection:

The cells were then blocked with Gammagard® (0.5%, 15 min, RT; Baxter Hyland Division, Los Angeles, Calif.). Anti-CD34 monoclonal antibody (0.5 mg of 9069 antibody [9C5], ATCC # HB 11646) was added to the cell suspension, the volume adjusted to 20 mL with working buffer and incubated for 15 minutes at room temperature with slow end-over-end rotation. The cells were washed twice (5 min, 400×g) and re-suspended in approximately 5 mL working buffer. SAM beads were used to rosette the sensitized target CD34+ cells. Beads ($8\times10^8$ per test) were washed 3 times in working buffer using a 2 minute exposure to the MPC-1 magnet (Dynal, Oslo, Norway) for collection. The sensitized cells, 2 mL of 5% Gammagard®, and the washed beads were added to an Isolex® 50 chamber. The volume was then adjusted to 20 mL with working buffer and incubated for 30 minutes at room temperature with slow end-over-end rotation. The bead/cell rosettes were collected using a 2 minute exposure to the Isolex® 50 magnets. Unbound cells were removed by draining the effluent. The rosettes were washed 3 times with 20 mL of working buffer using the magnet as described above. The effluent and negative washes were pooled for analysis. The release was carried out by incubation of the bead/cell rosettes with 9069N peptide (1 mg/mL; 20 mL working buffer) for 30 minutes at room temperature. The beads were collected using the magnets and the release cells were drained from the chamber. The beads were washed once and the wash was pooled with the released cells. The effluent cells were washed once and analyzed for total cell number and phenotype. CD34+ cells and B-cells are monitored throughout the process in order to evaluate performance (purity and yield) and purging (B-cell reduction).

Positive/Negative Selection—Simultaneous:

This procedure was as described above with the exception that 200 μg each of murine anti-CD10, CD19 and CD20 B-cell monoclonal antibodies (Baxter Immunotherapy, Munich, Germany) were added together with the 9069 [9C5] anti-CD34+ sensitization step. The murine monoclonal antibodies were deposited with the Deutsche Sammlung von Mikroorganismen und Zellkulturen GmbH of Braunschweig, Germany, under the provisions of the Budapest Treaty on the international recognition of the deposit of microorganisms for the purposes of patent procedure. The antibodies were assigned the following deposit numbers on May 23, 1995: anti-CD10 (W8E7E7), DSM ACC2215; anti-CD19 (HD237), DSM ACC2216; anti-CD20 (L27), DSM ACC2217.

Positive/Negative Selection—Sequential:

The process incorporated the positive selection procedure listed above followed by a negative selection step. Once the CD34+ cells had been released and collected as indicated in the positive selection section above, the cells were incubated with 200 μg of each B-Cell purging antibodies (CD10, 19 and 20, same three antibodies as above) in 10 mL for 15 minutes at room temperature. The positive selected fraction was then washed 2 times in working buffer to remove any unbound antibody. SAM beads ($4\times10^8$ ) and the B-cell antibody sensitized cells were incubated in an Isolex® 50 chamber in 10 mL volume at room temperature for 30 minutes. The B-cell rosettes were collected with a magnet and effluent was drained into a test tube. The beads were washed once and pooled with the effluent cells. The final produce was washed and analyzed as listed above.

The results were summarized in the tables below.

TABLE 31

POSITIVE SELECTION - CD34 PROFILE

| DONOR # | *STARTING CELL # | CELL # NEGATIVE FRACTION | CELL # FINAL PRODUCT | % CD34+ STARTING MATERIAL | % NEGATIVE FRACTION | % CD34 FINAL PRODUCT | % YIELD | % CAPTURE |
|---|---|---|---|---|---|---|---|---|
| UOM 4711 | $6\times10^9$ | $5.38\times10^9$ | $1.80\times10^7$ | 0.82 | 0.5 | 82.4 | 30.15 | 45.33 |
| UOM 4603 | $6\times10^9$ | $5.39\times10^9$ | $1.8\times10^7$ | 0.88 | 0.5 | 94.19 | 32.11 | 48.96 |
| UOM 4936 | $6\times10^9$ | $5.44\times10^9$ | $9.9\times10^6$ | 0.28 | 0.07 | 77.91 | 45.91 | 77.33 |

*Post-MNC Wash

TABLE 32

POSITIVE SELECTION - B-CELL PROFILE

| DONOR # | % B-CELL STARTING MATERIAL | % B-CELL NEGATIVE FRACTION | % B-CELL FINAL PRODUCT | % B-CELL CAPTURE | B-CELL LOG DEPLETION |
|---|---|---|---|---|---|
| UOM 4711 | 12.40 | 11.81 | 4.22 | 99.90 | 3.0 |
| UOM 4603 | 6.75 | 6.67 | 1.27 | 99.94 | 3.25 |
| UOM 4936 | 9.79 | 9.10 | 4.55 | 99.92 | 3.12 |

TABLE 33

POSITIVE/NEGATIVE SELECTION - SIMULTANEOUS - CD34 PROFILE

| DONOR # | *STARTING CELL # | CELL # NEGATIVE FRACTION | CELL # FINAL PRODUCT | % CD34+ STARTING MATERIAL | % NEGATIVE FRACTION | % CD34 FINAL PRODUCT | % YIELD | % CAPTURE |
|---|---|---|---|---|---|---|---|---|
| UOM 4711 | $6 \times 10^9$ | $4.78 \times 10^9$ | $2.11 \times 10^7$ | 0.82 | 0.61 | 61.68 | 26.45 | 40.74 |
| UOM 4603 | $6 \times 10^9$ | $5.12 \times 10^9$ | $2.10 \times 10^7$ | 0.88 | 0.59 | 77.42 | 30.79 | 42.79 |
| UOM 4936 | $6 \times 10^9$ | 5.02 | $9.6 \times 10^6$ | 0.28 | 0.19 | 46.27 | 26.44 | 43.23 |

*past-MNC Wash

TABLE 34

POSITIVE/NEGATIVE SELECTION - SIMULTANEOUS - B-CELL PROFILE

| DONOR # | % B-CELL STARTING MATERIAL | % B-CELL NEGATIVE FRACTION | % B-CELL FINAL PRODUCT | % B-CELL CAPTURE | B-CELL LOG DEPLETION |
|---|---|---|---|---|---|
| UOM 4711 | 12.40 | 0.41 | 8.63 | 97.37 | 2.61 |
| UOM 4603 | 6.75 | 0.41 | 15.01 | 94.82 | 2.11 |
| UOM 4936 | 9.79 | 0.42 | 19.11 | 96.41 | 2.51 |

TABLE 35

POSITIVE/NEGATIVE SELECTION - SEQUENTIAL - CD34 PROFILE

| DONOR # | *STARTING CELL # | CELL # NEGATIVE FRACTION | CELL # FINAL PRODUCT | % CD34+ STARTING MATERIAL | % NEGATIVE FRACTION | % CD34 FINAL PRODUCT | % YIELD | % CAPTURE |
|---|---|---|---|---|---|---|---|---|
| UOM 4711 | $6 \times 10^9$ | $5.17 \times 10^9$ | $1.54 \times 10^7$ | 0.82 | 0.41 | 94.5 | 29.58 | 56.92 |
| UOM 4603 | $6 \times 10^9$ | $5.3 \times 10^9$ | $1.62 \times 10^7$ | 0.88 | 0.47 | 96.99 | 29.76 | 52.82 |
| UOM 4936 | $6 \times 10^9$ | 5.48 | $6.3 \times 10^6$ | 0.28 | 0.16 | 88.95 | 33.36 | 47.81 |

*Post-MNC Wash

TABLE 36

POSITIVE/NEGATIVE SELECTION - SEQUENTIAL - B-CELL PROFILE

| DONOR # | % B-CELL STARTING MATERIAL | % B-CELL NEGATIVE FRACTION | % B-CELL FINAL PRODUCT | % B-CELL CAPTURE | B-CELL LOG DEPLETION |
|---|---|---|---|---|---|
| UOM 4711 | 12.40 | 11.41 | 0.1 | 98.29 | 4.7 |
| UOM 4603 | 6.75 | 6.60 | 0.11 | 93.59 | 4.4 |
| UOM 4936 | 9.79 | 8.85 | 0.91 | 86.0 | 4.01 |

What is claimed is:

1. A method for selection of one or more target cells from a heterogeneous cell suspension, comprising;

(a) forming within said cell suspension at least a first complex comprising a cell separation means linked to a first primary antibody bound to a cell surface antigen on said target cells, (b) separating said complex from said cell suspension, and (c) contacting said first primary antibody of said complex with a first peptide which binds to said primary antibody and displaces said primary antibody from said cell surface antigen, thereby releasing the target cell from the complex.

2. The method of claim 1 wherein said cell separation means is linked to said first primary antibody by a protein means for binding to said primary antibody, said protein means being coupled to said cell separation means.

3. The method of claim 1 further including a second complex comprising a second primary antibody linked to said cell separation means and bound to a second cell surface antigen on a target cell, said method further comprising contacting said second primary antibody with a second peptide which binds to said second primary antibody and thereby displaces said second primary antibody from said second cell surface antigen, thereby releasing the target cell from the complex.

4. The method of claim 1 wherein said complex further comprises a second primary antibody bound to a second cell surface antigen on an undesired cell.

5. A method for selection of one or more target cells from a heterogeneous cell suspension and the removal from said selected target cells of at least a first undesired cell, said method comprising;

(a) forming within said cell suspension a first plurality of complexes comprising a cell separation means linked to a first primary antibody bound to a first cell surface antigen present on said target cells, (b) separating said first plurality of complexes from said cell suspension, (c) contacting said first primary antibody of said complexes with a first peptide which binds to said first primary antibody to release said first primary antibody from said first cell surface antigen, thereby releasing the target cells from the complexes to form a first target cell composition including said target cells, (d) forming within said first target cell composition a second plurality of complexes comprising a cell separation means linked to a second primary antibody bound to a second cell surface antigen on said undesired cell, (e) separating said second plurality of complexes from said first cell composition to form a second target cell composition.

6. The method of claim 5 wherein said second target cell composition is substantially free of said undesired cell.

7. The method of claim 2 wherein said protein means for binding to the primary antibody is selected from the group consisting of *Staphylococcus aureus* Protein A, Streptococcus Protein G, and secondary antibodies.

8. The method of claim 7 wherein said primary antibody is a mouse monoclonal antibody, and said protein means for binding to the primary antibody is a secondary antibody comprising anti-mouse immunoglobulin.

9. The method of claim 8 wherein said secondary antibody is raised in an animal selected from the group consisting of rabbit, horse, goat, sheep, pig, and bovine species.

10. The method of claim 8 wherein said secondary antibody is a monoclonal antibody.

11. The method of claim 8 wherein said secondary antibody is a recombinant antibody produced by genetic engineering.

12. The method of claim 1 wherein said cell separation means is a solid support selected from the group consisting of paramagnetic beads, columns, hollow fibers, glass beads, polysaccharide beads, and polystyrene tissue culture flasks.

13. The method of claim 1, wherein said first primary antibody is a monoclonal antibody.

14. The method of claim 4, wherein said second primary antibody is a monoclonal antibody.

15. The method of claim 5, wherein said first primary antibody is a monoclonal antibody.

16. The method of claim 5, wherein said second primary antibody is a monoclonal antibody.

* * * * *

SEQUENCE LISTING (1) GENERAL INFORMATION:

(iii) NUMBER OF SEQUENCES: 215

(2) INFORMATION FOR SEQ ID NO:1:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:1:

```
Gln Gly Xaa Phe
1
```

(2) INFORMATION FOR SEQ ID NO:2:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:2:

```
Xaa Gln Gly Xaa Phe Xaa
1               5
```

(2) INFORMATION FOR SEQ ID NO:3:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:3:

```
Gln Gly Xaa Phe
1
```

(2) INFORMATION FOR SEQ ID NO:4:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:4:

```
Gln Gly Xaa Phe
1
```

(2) INFORMATION FOR SEQ ID NO:5:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:5:

```
Xaa Gln Gly Xaa Phe Xaa
```

1 5

(2) INFORMATION FOR SEQ ID NO:6:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:6:

Xaa Gln Gly Xaa Phe Xaa
1 5

(2) INFORMATION FOR SEQ ID NO:7:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:7:

Gln Gln Gly Trp Phe Pro
1 5

(2) INFORMATION FOR SEQ ID NO:8:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:8:

Thr Gln Gly Ser Phe Trp
1 5

(2) INFORMATION FOR SEQ ID NO:9:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:9:

Gln Gln Gly Trp Phe Pro Lys Asp
1 5

(2) INFORMATION FOR SEQ ID NO:10:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:10:

Gln Gln Gly Trp Phe Pro Asp Lys
1 5

(2) INFORMATION FOR SEQ ID NO:11:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:11:

```
Ala Asp Gly Ala Xaa Gln Gly Xaa Phe Xaa Gly Ala Lys Asp
1               5                   10
```

(2) INFORMATION FOR SEQ ID NO:12:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:12:

```
Ala Asp Gly Ala Gln Gln Gly Trp Phe Pro Gly Ala Lys Asp
1               5                   10
```

(2) INFORMATION FOR SEQ ID NO:13:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:13:

```
Ala Asp Gly Ala Thr Gln Gly Ser Phe Trp Gly Ala Lys Asp
1               5                   10
```

(2) INFORMATION FOR SEQ ID NO:14:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:14:

```
Asn Ser Ser Val Gln Ser
1               5
```

(2) INFORMATION FOR SEQ ID NO:15:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:15:

```
Ala Asp Gly Ala Leu Ile Ser Gln Val Ser Gly Ala Lys Asp
1               5                   10
```

(2) INFORMATION FOR SEQ ID NO:16:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:16:

```
Leu Ile Ser Gln Val Ser
1               5
```

(2) INFORMATION FOR SEQ ID NO:17:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:17:

```
Asn Ser Ser Val Xaa Xaa
1               5
```

(2) INFORMATION FOR SEQ ID NO:18:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:18:

```
Asn Ser Ser Val Gly Leu
1               5
```

(2) INFORMATION FOR SEQ ID NO:19:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:19:

```
Thr Gly Gln Ala Ser Thr
1               5
```

(2) INFORMATION FOR SEQ ID NO:20:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:20:

```
Ala Asp Gly Ala Pro Phe Trp Gly Gln Gln Gly Ala Lys Asp
1               5                   10
```

(2) INFORMATION FOR SEQ ID NO:21:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:21:

```
Ala Asp Gly Ala Thr Gln Gly Thr Phe Ser Gly Ala Lys Asp
```

```
1               5                   10


(2) INFORMATION FOR SEQ ID NO:22:

     (i) SEQUENCE CHARACTERISTICS:
          (A) LENGTH: 15 amino acids
          (B) TYPE: amino acid
          (D) TOPOLOGY: linear

    (ii) MOLECULE TYPE: peptide

    (xi) SEQUENCE DESCRIPTION: SEQ ID NO:22:

Pro Glu Leu Pro Thr Gln Gly Thr Phe Ser Asn Val Ser Lys Glu
1               5                   10                  15


(2) INFORMATION FOR SEQ ID NO:23:

     (i) SEQUENCE CHARACTERISTICS:
          (A) LENGTH: 14 amino acids
          (B) TYPE: amino acid
          (D) TOPOLOGY: linear

    (ii) MOLECULE TYPE: peptide

    (xi) SEQUENCE DESCRIPTION: SEQ ID NO:23:

Ala Asp Gly Ala Thr Gln Gly Ile Cys Leu Gly Ala Lys Asp
1               5                   10


(2) INFORMATION FOR SEQ ID NO:24:

     (i) SEQUENCE CHARACTERISTICS:
          (A) LENGTH: 15 amino acids
          (B) TYPE: amino acid
          (D) TOPOLOGY: linear

    (ii) MOLECULE TYPE: peptide

    (xi) SEQUENCE DESCRIPTION: SEQ ID NO:24:

Glu Val Lys Leu Thr Gln Gly Ile Cys Leu Glu Gln Asn Lys Thr
1               5                   10                  15


(2) INFORMATION FOR SEQ ID NO:25:

     (i) SEQUENCE CHARACTERISTICS:
          (A) LENGTH: 14 amino acids
          (B) TYPE: amino acid
          (D) TOPOLOGY: linear

    (ii) MOLECULE TYPE: peptide

    (xi) SEQUENCE DESCRIPTION: SEQ ID NO:25:

Ala Asp Gly Ala Asn Gln Gly Tyr Phe Pro Gly Ala Lys Asp
1               5                   10


(2) INFORMATION FOR SEQ ID NO:26:

     (i) SEQUENCE CHARACTERISTICS:
          (A) LENGTH: 8 amino acids
          (B) TYPE: amino acid
          (D) TOPOLOGY: linear

    (ii) MOLECULE TYPE: peptide

    (xi) SEQUENCE DESCRIPTION: SEQ ID NO:26:

Pro Gly Ser Pro Leu Gly Lys Asp
1               5


(2) INFORMATION FOR SEQ ID NO:27:
```

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:27:

```
Tyr Ser Arg Leu Gly Phe Lys Asp
1               5
```

(2) INFORMATION FOR SEQ ID NO:28:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:28:

```
Gln Tyr Thr Gln Pro Lys Asp
1               5
```

(2) INFORMATION FOR SEQ ID NO:29:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:29:

```
Asn Leu Gln Gly Glu Phe Lys Asp
1               5
```

(2) INFORMATION FOR SEQ ID NO:30:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:30:

```
Arg Ser Phe Tyr Tyr Arg Asp
1               5
```

(2) INFORMATION FOR SEQ ID NO:31:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:31:

```
Ile Gln Glu Phe Gly Val Lys Asp
1               5
```

(2) INFORMATION FOR SEQ ID NO:32:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:32:

Ser Phe Arg Val Gly Tyr Lys Asp
1               5

(2) INFORMATION FOR SEQ ID NO:33:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO:33:

Lys Asp Val Tyr Ser Leu Trp Pro Lys Asp
1               5                   10

(2) INFORMATION FOR SEQ ID NO:34:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:34:

Arg His Arg His Arg His
1               5

(2) INFORMATION FOR SEQ ID NO:35:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:35:

Lys Arg His Lys Arg His
1               5

(2) INFORMATION FOR SEQ ID NO:36:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:36:

Arg Thr Lys Thr Arg Phe
1               5

(2) INFORMATION FOR SEQ ID NO:37:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:37:

Thr Arg Val Pro Arg Arg

```
1               5


(2) INFORMATION FOR SEQ ID NO:38:

     (i) SEQUENCE CHARACTERISTICS:
          (A) LENGTH: 6 amino acids
          (B) TYPE: amino acid
          (D) TOPOLOGY: linear

    (ii) MOLECULE TYPE: peptide

    (xi) SEQUENCE DESCRIPTION: SEQ ID NO:38:

Arg His Arg Pro Arg His
1               5


(2) INFORMATION FOR SEQ ID NO:39:

     (i) SEQUENCE CHARACTERISTICS:
          (A) LENGTH: 7 amino acids
          (B) TYPE: amino acid
          (D) TOPOLOGY: linear

    (ii) MOLECULE TYPE: peptide

    (xi) SEQUENCE DESCRIPTION: SEQ ID NO:39:

Asp Asn Tyr Trp Met Gln Lys
1               5


(2) INFORMATION FOR SEQ ID NO:40:

     (i) SEQUENCE CHARACTERISTICS:
          (A) LENGTH: 17 amino acids
          (B) TYPE: amino acid
          (D) TOPOLOGY: linear

    (ii) MOLECULE TYPE: peptide

    (xi) SEQUENCE DESCRIPTION: SEQ ID NO:40:

Ala Ile Tyr Pro Gly Asp Gly Asp Thr Arg Tyr Thr Gln Lys Phe Lys
1               5                   10                  15

Val


(2) INFORMATION FOR SEQ ID NO:41:

     (i) SEQUENCE CHARACTERISTICS:
          (A) LENGTH: 10 amino acids
          (B) TYPE: amino acid
          (D) TOPOLOGY: linear

    (ii) MOLECULE TYPE: peptide

    (xi) SEQUENCE DESCRIPTION: SEQ ID NO:41:

Asn Asp Gly Tyr Phe Asp Ala Met Asp Tyr
1               5                   10


(2) INFORMATION FOR SEQ ID NO:42:

     (i) SEQUENCE CHARACTERISTICS:
          (A) LENGTH: 12 amino acids
          (B) TYPE: amino acid
          (D) TOPOLOGY: linear

    (ii) MOLECULE TYPE: peptide

    (xi) SEQUENCE DESCRIPTION: SEQ ID NO:42:

Asp Ser Ala Ser Ser Ser Val Thr Phe Met His Lys
1               5                   10
```

(2) INFORMATION FOR SEQ ID NO:43:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:43:

Asp Thr Ser Lys Leu Ala Ser
1 5

(2) INFORMATION FOR SEQ ID NO:44:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:44:

Asp Gln Gln Trp Asn Ser Asn Pro Leu Thr Lys
1 5 10

(2) INFORMATION FOR SEQ ID NO:45:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:45:

Asp Asn Tyr Trp Met Gln Lys Asp
1 5

(2) INFORMATION FOR SEQ ID NO:46:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:46:

Lys Asp Ser Ala Ser Ser Ser Val Thr Phe Met His Lys Asp
1 5 10

(2) INFORMATION FOR SEQ ID NO:47:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:47:

Ala Arg Asn Asp Gly Tyr Phe Asp Ala Met Asp
1 5 10

(2) INFORMATION FOR SEQ ID NO:48:

(i) SEQUENCE CHARACTERISTICS:
(A) LENGTH: 11 amino acids
(B) TYPE: amino acid (D) TOPOLOGY: linear (ii) MOLECULE TYPE: peptide (xi) SEQUENCE DESCRIPTION: SEQ ID NO:48:

```
His Asp Thr Ser Lys Leu Ala Ser Gln Val Asp
1               5                   10
```

(2) INFORMATION FOR SEQ ID NO:49:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:49:

```
Thr Cys Thr Asn Cys His Lys Asp
1               5
```

(2) INFORMATION FOR SEQ ID NO:50:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:50:

```
Ala Cys Lys Trp Cys Arg
1               5
```

(2) INFORMATION FOR SEQ ID NO:51:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:51:

```
Gln Lys Thr Asp Ala Tyr Lys Asp
1               5
```

(2) INFORMATION FOR SEQ ID NO:52:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO:52:

```
Lys Asp Pro Ala Asn Val Ser Leu Lys Asp
1               5                   10
```

(2) INFORMATION FOR SEQ ID NO:53:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:53:

Lys Asp Pro Ala Asn Val Ser Thr Lys Asp Cys
1 5 10

(2) INFORMATION FOR SEQ ID NO:54:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:54:

Thr Cys Lys Trp Cys Arg
1 5

(2) INFORMATION FOR SEQ ID NO:55:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:55:

Arg Val Ser Trp Cys Arg
1 5

(2) INFORMATION FOR SEQ ID NO:56:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:56:

Thr Cys Thr Asn Cys His
1 5

(2) INFORMATION FOR SEQ ID NO:57:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:57:

Thr Cys Thr Lys Val His
1 5

(2) INFORMATION FOR SEQ ID NO:58:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:58:

Phe Phe Arg Asp Val Tyr
1 5

(2) INFORMATION FOR SEQ ID NO:59:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:59:

Phe Leu His Glu Cys Tyr
1 5

(2) INFORMATION FOR SEQ ID NO:60:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:60:

Tyr Ile Lys Gly Leu Phe
1 5

(2) INFORMATION FOR SEQ ID NO:61:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:61:

Tyr Ile Gly Thr Asp His
1 5

(2) INFORMATION FOR SEQ ID NO:62:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:62:

Val Ile Met Glu Glu Ala
1 5

(2) INFORMATION FOR SEQ ID NO:63:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:63:

Lys Leu Ile Ala Thr Ala
1 5

(2) INFORMATION FOR SEQ ID NO:64:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:64:

Thr Ala Ala His Thr Trp
1 5

(2) INFORMATION FOR SEQ ID NO:65:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:65:

Cys Ser Leu His His Tyr
1 5

(2) INFORMATION FOR SEQ ID NO:66:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:66:

Val Leu Leu Ser Asp Asn
1 5

(2) INFORMATION FOR SEQ ID NO:67:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:67:

Met Val Trp Val Asn Asn
1 5

(2) INFORMATION FOR SEQ ID NO:68:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:68:

Ser Trp Asn Tyr Thr His
1 5

(2) INFORMATION FOR SEQ ID NO:69:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:69:

Arg Val Ser Gly Val Gly
1 5

(2) INFORMATION FOR SEQ ID NO:70:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:70:

Arg Val Ser Gly Cys Arg
1 5

(2) INFORMATION FOR SEQ ID NO:71:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:71:

Arg Tyr Gly Gly Ser Phe
1 5

(2) INFORMATION FOR SEQ ID NO:72:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:72:

Leu Arg Lys Val Asn Gly
1 5

(2) INFORMATION FOR SEQ ID NO:73:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:73:

Trp Ser Val Gln Arg Asp
1 5

(2) INFORMATION FOR SEQ ID NO:74:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:74:

Phe Ser Ile Gly Ala Gly
1 5

(2) INFORMATION FOR SEQ ID NO:75:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:75:

Ser Pro Phe Val Thr Met
1 5

(2) INFORMATION FOR SEQ ID NO:76:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:76:

Ser Trp Asn Tyr Thr His
1 5

(2) INFORMATION FOR SEQ ID NO:77:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:77:

Arg Val Ser Gly Val Gly
1 5

(2) INFORMATION FOR SEQ ID NO:78:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:78:

Arg Val Ser Gly Cys Arg
1 5

(2) INFORMATION FOR SEQ ID NO:79:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:79:

Arg Tyr Gly Gly Ser Phe
1 5

(2) INFORMATION FOR SEQ ID NO:80:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:80:

Leu Arg Lys Val Asn Gly
1 5

(2) INFORMATION FOR SEQ ID NO:81:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:81:

Trp Ser Val Gln Arg Asp
1 5

(2) INFORMATION FOR SEQ ID NO:82:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:82:

Phe Ser Ile Gly Ala Gly
1 5

(2) INFORMATION FOR SEQ ID NO:83:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:83:

Ser Pro Phe Val Thr Met
1 5

(2) INFORMATION FOR SEQ ID NO:84:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:84:

Ala Cys Glu Trp Cys Arg
1 5

(2) INFORMATION FOR SEQ ID NO:85:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:85:

Ala Trp Trp Ser Asn Thr
1 5

(2) INFORMATION FOR SEQ ID NO:86:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:86:

Trp Cys Arg Arg Ile Thr
1 5

(2) INFORMATION FOR SEQ ID NO:87:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:87:

Gln Lys Thr Asp Ala Tyr
1 5

(2) INFORMATION FOR SEQ ID NO:88:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:88:

Gln Lys Ala Glu Ala Tyr
1 5

(2) INFORMATION FOR SEQ ID NO:89:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:89:

Gln Lys Ala Asp Ala Tyr
1 5

(2) INFORMATION FOR SEQ ID NO:90:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:90:

Gln Glu Thr Asp Ala Tyr
1 5

(2) INFORMATION FOR SEQ ID NO:91:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:91:

Gln Glu Ala Asp Ala Tyr
1 5

(2) INFORMATION FOR SEQ ID NO:92:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:92:

Gln Gln Ala Asp Ala Tyr
1 5

(2) INFORMATION FOR SEQ ID NO:93:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:93:

Gln Gln Thr Asp Ala Tyr
1 5

(2) INFORMATION FOR SEQ ID NO:94:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:94:

Pro Ala Asn Val Ser Leu
1 5

(2) INFORMATION FOR SEQ ID NO:95:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:95:

Pro Ala Asp Val Ser Leu
1 5

(2) INFORMATION FOR SEQ ID NO:96:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:96:

Pro Pro Asn Val Ser Leu
1 5

(2) INFORMATION FOR SEQ ID NO:97:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:97:

Thr Pro Asn Val Ser Leu
1 5

(2) INFORMATION FOR SEQ ID NO:98:

(i) SEQUENCE CHARACTERISTICS:
(A) LENGTH: 12 amino acids
(B) TYPE: amino acid
(D) TOPOLOGY: circular (ii) MOLECULE TYPE: peptide (xi) SEQUENCE DESCRIPTION: SEQ ID NO:98:

Gln Cys Ile Asp Glu Phe Leu Arg Cys Ile Lys Asp
1 5 10

(2) INFORMATION FOR SEQ ID NO:99:

(i) SEQUENCE CHARACTERISTICS:
(A) LENGTH: 13 amino acids
(B) TYPE: amino acid
(D) TOPOLOGY: circular (ii) MOLECULE TYPE: peptide (xi) SEQUENCE DESCRIPTION: SEQ ID NO:99:

Asp Gln Cys Ile Asp Glu Phe Leu Arg Cys Ile Lys Asp
1 5 10

(2) INFORMATION FOR SEQ ID NO:100:

(i) SEQUENCE CHARACTERISTICS:
(A) LENGTH: 12 amino acids
(B) TYPE: amino acid
(D) TOPOLOGY: circular (ii) MOLECULE TYPE: peptide (xi) SEQUENCE DESCRIPTION: SEQ ID NO:100:

Asp Gln Cys Ile Asp Glu Phe Leu Arg Cys Ile Asp
1 5 10

(2) INFORMATION FOR SEQ ID NO:101:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:101:

Gln Cys Ile Asp Glu Phe Leu Arg Cys Ile
1 5 10

(2) INFORMATION FOR SEQ ID NO:102:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:102:

Asp Cys Ile Asp Thr Phe Leu Arg Cys Val
1 5 10

(2) INFORMATION FOR SEQ ID NO:103:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:103:

Ser Cys Ile Asp Asp Phe Leu Arg Cys Ala
1 5 10

(2) INFORMATION FOR SEQ ID NO:104:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:104:

Gln Cys Ile Asp Ala Phe Arg Arg Cys Ile
1 5 10

(2) INFORMATION FOR SEQ ID NO:105:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:105:

Asn Cys Ile Asp Thr Phe Val Ala Cys Ala
1 5 10

(2) INFORMATION FOR SEQ ID NO:106:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:106:

Asn Cys Ile Asp Lys Phe Leu Ala Cys Val
1 5 10

(2) INFORMATION FOR SEQ ID NO:107:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:107:

```
Gln Cys Ile Asp Glu Leu Leu Arg Cys Ile
1               5                   10
```

(2) INFORMATION FOR SEQ ID NO:108:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:108:

```
Asn Cys Ile Asp Val Phe Leu Thr Cys Val
1               5                   10
```

(2) INFORMATION FOR SEQ ID NO:109:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:109:

```
Asp Cys Ile Glu Arg Phe Leu Thr Cys Val
1               5                   10
```

(2) INFORMATION FOR SEQ ID NO:110:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:110:

```
Asn Cys Ile Glu Ile Phe Ile Ser Cys Val
1               5                   10
```

(2) INFORMATION FOR SEQ ID NO:111:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:111:

```
Ser Cys Ile Glu Thr Phe Leu Gly Cys Val
1               5                   10
```

(2) INFORMATION FOR SEQ ID NO:112:

(i) SEQUENCE CHARACTERISTICS:
(A) LENGTH: 10 amino acids
(B) TYPE: amino acid (D) TOPOLOGY: circular (ii) MOLECULE TYPE: peptide (xi) SEQUENCE DESCRIPTION: SEQ ID NO:112:

```
Gly Cys Ile Glu Arg Phe Phe Gln Cys Val
1               5                   10
```

(2) INFORMATION FOR SEQ ID NO:113:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:113:

```
Asn Cys Ile Glu Ser Phe Leu Arg Cys Val
1               5                   10
```

(2) INFORMATION FOR SEQ ID NO:114:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:114:

```
Ser Cys Ile Asn Arg Phe Leu Thr Cys Val
1               5                   10
```

(2) INFORMATION FOR SEQ ID NO:115:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:115:

```
Ser Cys Thr Asn Arg Phe Leu Thr Cys Val
1               5                   10
```

(2) INFORMATION FOR SEQ ID NO:116:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:116:

```
Ser Cys Pro Val Ala Ile Ala Ser Cys Thr
1               5                   10
```

(2) INFORMATION FOR SEQ ID NO:117:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:117:

Asn Cys Val Asp Gln Phe Ile His Cys Val
1 5 10

(2) INFORMATION FOR SEQ ID NO:118:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:118:

Asn Cys Val Glu Ala Phe Leu Ile Cys Ala
1 5 10

(2) INFORMATION FOR SEQ ID NO:119:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:119:

Asn Cys Val Asp Lys Phe Leu Ala Cys Ala
1 5 10

(2) INFORMATION FOR SEQ ID NO:120:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:120:

Gln Cys Ile Ala Glu Phe Leu Arg Cys Ile
1 5 10

(2) INFORMATION FOR SEQ ID NO:121:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:121:

Asp Cys Val Glu Gln Phe Leu Thr Cys Val
1 5 10

(2) INFORMATION FOR SEQ ID NO:122:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:122:

Leu Cys Arg Leu Leu Lys Gln Leu Cys Asn
1 5 10

(2) INFORMATION FOR SEQ ID NO:123:

(i) SEQUENCE CHARACTERISTICS:
(A) LENGTH: 10 amino acids
(B) TYPE: amino acid
(D) TOPOLOGY: circular (ii) MOLECULE TYPE: peptide (xi) SEQUENCE DESCRIPTION: SEQ ID NO:123:

```
Ile Cys Thr Asp Arg Tyr Pro Pro Cys Thr
1               5                   10
```

(2) INFORMATION FOR SEQ ID NO:124:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:124:

```
Arg Trp Arg Trp Arg His
1               5
```

(2) INFORMATION FOR SEQ ID NO:125:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:125:

```
Ala Arg Phe Pro Arg Arg
1               5
```

(2) INFORMATION FOR SEQ ID NO:126:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:126:

```
Arg His His Leu Tyr Arg
1               5
```

(2) INFORMATION FOR SEQ ID NO:127:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:127:

```
Trp Tyr Arg Ser His Arg
1               5
```

(2) INFORMATION FOR SEQ ID NO:128:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:128:

Thr Arg Val Pro Arg Arg
1 5

(2) INFORMATION FOR SEQ ID NO:129:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:129:

Thr Pro Arg Asn Pro Arg
1 5

(2) INFORMATION FOR SEQ ID NO:130:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:130:

Leu Arg Arg Thr Phe Trp
1 5

(2) INFORMATION FOR SEQ ID NO:131:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:131:

Leu Val Arg Ile Gln Phe
1 5

(2) INFORMATION FOR SEQ ID NO:132:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:132:

Leu Val Arg Val Trp Phe
1 5

(2) INFORMATION FOR SEQ ID NO:133:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:133:

Leu Thr Arg Thr Val Phe
1 5

(2) INFORMATION FOR SEQ ID NO:134:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:134:

Arg Thr Lys Thr Arg Phe
1 5

(2) INFORMATION FOR SEQ ID NO:135:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:135:

Ala Asp Gly Ala Glu Gln Gly Phe Phe Pro Gly Ala Lys Asp
1 5 10

(2) INFORMATION FOR SEQ ID NO:136:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:136:

Thr Gln Gly Thr Phe Ser
1 5

(2) INFORMATION FOR SEQ ID NO:137:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:137:

Gln Gln Gly Phe Phe Pro Lys Asp
1 5

(2) INFORMATION FOR SEQ ID NO:138:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:138:

Thr Gln Gly Thr Phe Ser
1 5

(2) INFORMATION FOR SEQ ID NO:139:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:139:

Glu Gln Gly Phe Phe Pro
1               5

(2) INFORMATION FOR SEQ ID NO:140:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:140:

Asn Gln Gly Tyr Phe Pro
1               5

(2) INFORMATION FOR SEQ ID NO:141:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:141:

Arg Ile Gly Ala Phe Arg
1               5

(2) INFORMATION FOR SEQ ID NO:142:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:142:

Ser Phe Arg Val Gly Tyr
1               5

(2) INFORMATION FOR SEQ ID NO:143:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:143:

Asp Gly Leu Pro Ala Arg
1               5

(2) INFORMATION FOR SEQ ID NO:144:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:144:

Trp Ser Ser Asn Arg Phe
1 5

(2) INFORMATION FOR SEQ ID NO:145:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:145:

Arg Glu Arg Thr Ser Ser
1 5

(2) INFORMATION FOR SEQ ID NO:146:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:146:

Ser Trp Arg His Val Gln
1 5

(2) INFORMATION FOR SEQ ID NO:147:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:147:

Gly Leu Pro Arg Ser Trp
1 5

(2) INFORMATION FOR SEQ ID NO:148:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:148:

Asn Gln Arg Trp Leu Leu
1 5

(2) INFORMATION FOR SEQ ID NO:149:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:149:

Ile Phe Gln Arg Asn Met
1 5

(2) INFORMATION FOR SEQ ID NO:150:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:150:

Arg Met Asp Gly Thr Phe
1 5

(2) INFORMATION FOR SEQ ID NO:151:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:151:

Leu Pro Tyr Leu Met Arg
1 5

(2) INFORMATION FOR SEQ ID NO:152:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:152:

Met Asn Tyr Val Ser Leu
1 5

(2) INFORMATION FOR SEQ ID NO:153:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:153:

Thr Met Thr Phe His Gly
1 5

(2) INFORMATION FOR SEQ ID NO:154:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:154:

Met Thr Tyr Ser Ser Gly
1 5

(2) INFORMATION FOR SEQ ID NO:155:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:155:

His Thr Pro Met Val Thr
1 5

(2) INFORMATION FOR SEQ ID NO:156:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:156:

Gly His His Ala Thr Gly
1 5

(2) INFORMATION FOR SEQ ID NO:157:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:157:

His Asp Gly Leu Tyr Ile
1 5

(2) INFORMATION FOR SEQ ID NO:158:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:158:

Gln His Pro Phe Thr Val
1 5

(2) INFORMATION FOR SEQ ID NO:159:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:159:

Gln Val Gly Glu Gln His
1 5

(2) INFORMATION FOR SEQ ID NO:160:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:160:

Gln Thr Ser Leu Leu His
1 5

(2) INFORMATION FOR SEQ ID NO:161:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:161:

Ser Leu Leu Tyr Val Asp
1 5

(2) INFORMATION FOR SEQ ID NO:162:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:162:

Leu Gly Gly Trp Leu Ala
1 5

(2) INFORMATION FOR SEQ ID NO:163:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:163:

Pro Val Phe Leu Gly Val
1 5

(2) INFORMATION FOR SEQ ID NO:164:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:164:

Trp Asn Leu Ser Asp Lys
1 5

(2) INFORMATION FOR SEQ ID NO:165:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:165:

Ile Gln Glu Phe Gly Val
1 5

(2) INFORMATION FOR SEQ ID NO:166:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:166:

Thr Thr Asp Gln Phe Ser
1 5

(2) INFORMATION FOR SEQ ID NO:167:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:167:

Xaa Ser Xaa Val Phe Arg
1 5

(2) INFORMATION FOR SEQ ID NO:168:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:168:

Arg Ala Ala Gly Leu Xaa
1 5

(2) INFORMATION FOR SEQ ID NO:169:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:169:

Met Leu Pro Xaa Xaa Gly
1 5

(2) INFORMATION FOR SEQ ID NO:170:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:170:

Arg Ser Phe Tyr Tyr Arg
1 5

(2) INFORMATION FOR SEQ ID NO:171:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:171:

Tyr Val Ala Xaa Thr His
1               5

(2) INFORMATION FOR SEQ ID NO:172:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:172:

Ala Tyr Glu Ala Gln Ala
1               5

(2) INFORMATION FOR SEQ ID NO:173:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:173:

Gln Arg Phe Ala Ser Val
1               5

(2) INFORMATION FOR SEQ ID NO:174:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:174:

Asn Leu Gln Gly Glu Leu
1               5

(2) INFORMATION FOR SEQ ID NO:175:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:175:

Ser Phe Asn His Pro Val
1               5

(2) INFORMATION FOR SEQ ID NO:176:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:176:

Asn Leu Gln Gly Glu Phe
1 5

(2) INFORMATION FOR SEQ ID NO:177:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:177:

Pro Gly Ser Pro Leu Gly
1 5

(2) INFORMATION FOR SEQ ID NO:178:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:178:

Tyr Ser Arg Leu Gly Phe
1 5

(2) INFORMATION FOR SEQ ID NO:179:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:179:

Gln Val Leu Arg Glu Ser
1 5

(2) INFORMATION FOR SEQ ID NO:180:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:180:

Ser Asp Leu Thr Leu Arg
1 5

(2) INFORMATION FOR SEQ ID NO:181:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:181:

Met Arg Tyr Pro Thr Arg
1 5

(2) INFORMATION FOR SEQ ID NO:182:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:182:

His Ile Gly Ile Ser Leu
1 5

(2) INFORMATION FOR SEQ ID NO:183:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:183:

Arg Xaa Ser Glu Phe Xaa
1 5

(2) INFORMATION FOR SEQ ID NO:184:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:184:

Val Val Arg Ser Leu Tyr
1 5

(2) INFORMATION FOR SEQ ID NO:185:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:185:

Gly Tyr Thr Gln Pro Lys
1 5

(2) INFORMATION FOR SEQ ID NO:186:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:186:

Tyr Met Trp Val Thr Glu
1 5

(2) INFORMATION FOR SEQ ID NO:187:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:187:

Gly Tyr Thr Gln Pro Ile
1 5

(2) INFORMATION FOR SEQ ID NO:188:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:188:

Ile Arg Ala Arg Gly Asn
1 5

(2) INFORMATION FOR SEQ ID NO:189:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:189:

Val Tyr Ser Leu Trp Pro
1 5

(2) INFORMATION FOR SEQ ID NO:190:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:190:

Pro Ala Asn Val Ser Thr
1 5

(2) INFORMATION FOR SEQ ID NO:191:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:191:

Asn Val Ser Thr
1

(2) INFORMATION FOR SEQ ID NO:192:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:192:

Thr Gln Gly Thr Phe Ser
1 5

(2) INFORMATION FOR SEQ ID NO:193:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:193:

Leu Pro Thr Gln Gly Thr
1 5

(2) INFORMATION FOR SEQ ID NO:194:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:194:

Gln His Gly Asn Glu Ala Thr
1 5

(2) INFORMATION FOR SEQ ID NO:195:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:195:

Gly Asn Thr Asn Ser
1 5

(2) INFORMATION FOR SEQ ID NO:196:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:196:

Asn Val Ser Thr
1

(2) INFORMATION FOR SEQ ID NO:197:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:197:

Leu Ser Pro Gly
1

(2) INFORMATION FOR SEQ ID NO:198:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:198:

Lys Pro Ser Leu Ser Pro Gly Lys Asp
1 5

(2) INFORMATION FOR SEQ ID NO:199:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:199:

Thr Lys Pro Tyr Thr Ser Ser Ser
1 5

(2) INFORMATION FOR SEQ ID NO:200:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:200:

Asp Thr Lys Pro Tyr Thr Ser Ser Ser Lys Asp
1 5 10

(2) INFORMATION FOR SEQ ID NO:201:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:201:

Gln Asn Lys Thr Ser Ser
1 5

(2) INFORMATION FOR SEQ ID NO:202:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO:202:

Leu Glu Gln Asn Lys Thr Ser Ser Lys Asp
1 5 10

(2) INFORMATION FOR SEQ ID NO:203:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:203:

Phe Lys Lys Asp Arg Gly
1 5

(2) INFORMATION FOR SEQ ID NO:204:

(i) SEQUENCE CHARACTERISTICS:
(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO:204:

Glu Phe Lys Lys Asp Arg Gly Glu Gly Leu Ala Arg
1 5 10

(2) INFORMATION FOR SEQ ID NO:205:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:205:

Cys Ile Asp Glu Phe Leu Arg Cys Ile
1 5

(2) INFORMATION FOR SEQ ID NO:206:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:206:

Ser Glu Val Arg
1

(2) INFORMATION FOR SEQ ID NO:207:

(i) SEQUENCE CHARACTERISTICS:
(A) LENGTH: 12 amino acids
(B) TYPE: amino acid
(D) TOPOLOGY: linear (ii) MOLECULE TYPE: peptide (xi) SEQUENCE DESCRIPTION: SEQ ID NO:207:

Asp Leu Ala Gln Ser Glu Val Arg Pro Gln Lys Asp
1 5 10

(2) INFORMATION FOR SEQ ID NO:208:

(i) SEQUENCE CHARACTERISTICS:
(A) LENGTH: 6 amino acids
(B) TYPE: amino acid (D) TOPOLOGY: linear (ii) MOLECULE TYPE: peptide (xi) SEQUENCE DESCRIPTION: SEQ ID NO:208:

```
Gln Ser Tyr Ser Gln Lys
1               5
```

(2) INFORMATION FOR SEQ ID NO:209:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO:209:

```
Lys Asp His Gln Ser Tyr Ser Gln Lys Thr
1               5                   10
```

(2) INFORMATION FOR SEQ ID NO:210:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:210:

```
CAATTAAAGG CTCCTTTTGG AGCC                                          24
```

(2) INFORMATION FOR SEQ ID NO:211:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:211:

```
GCCCTCATAG TTAGCGTAAC GATC                                          24
```

(2) INFORMATION FOR SEQ ID NO:212:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO:212:

```
Cys Ala Glu Phe Lys Lys Asp Arg Gly Glu Gly Leu Ala Arg Val Leu
1               5                   10                  15

Cys
```

(2) INFORMATION FOR SEQ ID NO:213:

(i) SEQUENCE CHARACTERISTICS:
(A) LENGTH: 10 amino acids
(B) TYPE: amino acid
(D) TOPOLOGY: linear (ii) MOLECULE TYPE: peptide

```
    (xi) SEQUENCE DESCRIPTION: SEQ ID NO:213:

Glu Glu Glu Glu Tyr Met Pro Met Glu Gly
1               5                   10


(2) INFORMATION FOR SEQ ID NO:214:

     (i) SEQUENCE CHARACTERISTICS:
          (A) LENGTH: 12 amino acids
          (B) TYPE: amino acid
          (D) TOPOLOGY: linear

    (ii) MOLECULE TYPE: peptide

    (xi) SEQUENCE DESCRIPTION: SEQ ID NO:214:

Glu Glu Glu Glu Glu Glu Glu Glu Glu Glu Glu Glu
1               5                   10


(2) INFORMATION FOR SEQ ID NO:215:

     (i) SEQUENCE CHARACTERISTICS:
          (A) LENGTH: 11 amino acids
          (B) TYPE: amino acid
          (D) TOPOLOGY: linear

    (ii) MOLECULE TYPE: peptide

    (xi) SEQUENCE DESCRIPTION: SEQ ID NO:215:

Asp Asp Asp Asp Asp Asp Asp Asp Asp Asp Asp
1               5                   10
```